United States Patent
Katuin et al.

(10) Patent No.: US 11,951,285 B2
(45) Date of Patent: Apr. 9, 2024

(54) CONNECTED INJECTION DEVICES WITH STATUS SENSING SYSTEMS

(71) Applicant: Eli Lilly and Company, Indianapolis, IN (US)

(72) Inventors: Joseph Edward Katuin, Cicero, IN (US); Adam Nathaniel Wiesler, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 266 days.

(21) Appl. No.: 17/320,554

(22) Filed: May 14, 2021

(65) Prior Publication Data
US 2021/0268188 A1 Sep. 2, 2021

Related U.S. Application Data

(63) Continuation of application No. 16/764,294, filed as application No. PCT/US2019/053438 on Sep. 27, 2019, now Pat. No. 11,123,488.
(Continued)

(51) Int. Cl.
*A61M 5/20* (2006.01)
*A61M 5/31* (2006.01)
*A61M 5/315* (2006.01)

(52) U.S. Cl.
CPC ............ *A61M 5/20* (2013.01); *A61M 5/3137* (2013.01); *A61M 5/31576* (2013.01);
(Continued)

(58) Field of Classification Search
CPC ........ A61M 2005/206; A61M 2205/33; A61M 2205/50; A61M 2205/52;
(Continued)

(56) References Cited

U.S. PATENT DOCUMENTS

| | | |
|---|---|---|
| 5,782,814 A | 7/1998 | Brown et al. |
| 6,171,276 B1 | 1/2001 | Lippe et al. |

(Continued)

FOREIGN PATENT DOCUMENTS

| | | |
|---|---|---|
| EP | 2777731 A1 | 9/2014 |
| EP | 2777731 | 1/2017 |

(Continued)

OTHER PUBLICATIONS

Solutions for Medical Devices brochure, 3M, 2006, http://multimedia.3m.com/mws/media/376788O/3mtm-solutions-for-medical-devices-brochure.pdf.
(Continued)

*Primary Examiner* — Ariana Zimbouski
*Assistant Examiner* — Anna E Goldberg-Richmeier
(74) *Attorney, Agent, or Firm* — Arthur Shum

(57) ABSTRACT

An injection device assembly including a housing, a syringe, a drive mechanism and one or more sensing systems are described. The drive mechanism advances the syringe from a storage position to an injection position, and a plunger advances the syringe piston from an initial position to a final position. The status sensing system may include one or more main PCB(s) disposed in an end portion of the injection device assembly's housing. The system may determine various parameters related to an operational status of the injection device, including the location of the device's components, an amount of medication remaining in the device, a temperature of the medication, and whether or not the device is properly contacting the user's skin before injection. The system may communicate such determined parameters to an external device via a wireless communication link.

42 Claims, 33 Drawing Sheets

Related U.S. Application Data

(60) Provisional application No. 62/818,308, filed on Mar. 14, 2019, provisional application No. 62/740,539, filed on Oct. 3, 2018.

(52) U.S. Cl.
CPC .............. *A61M 2005/206* (2013.01); *A61M 2205/3317* (2013.01); *A61M 2205/3368* (2013.01); *A61M 2205/3553* (2013.01); *A61M 2205/50* (2013.01); *A61M 2205/8287* (2013.01)

(58) Field of Classification Search
CPC .............. A61M 2205/332; A61M 5/20; A61M 2205/3317; A61M 5/2033
See application file for complete search history.

(56) References Cited

U.S. PATENT DOCUMENTS

| | | |
|---|---|---|
| 6,491,657 B2 | 12/2002 | Rowe et al. |
| 6,547,755 B1 | 4/2003 | Lippe et al. |
| 6,793,633 B2 | 9/2004 | Douglas et al. |
| 7,628,780 B2 | 12/2009 | Bonner et al. |
| 7,731,686 B2 | 6/2010 | Edwards et al. |
| 7,927,288 B2 | 4/2011 | Gianchandani et al. |
| 8,088,096 B2 | 1/2012 | Lauchard et al. |
| 8,172,082 B2 | 5/2012 | Edwards et al. |
| 8,464,707 B2 | 6/2013 | Jongejan et al. |
| 8,556,866 B2 | 10/2013 | Krulevitch et al. |
| 8,807,131 B1 | 8/2014 | Tunnell et al. |
| 8,882,704 B2 | 11/2014 | Fago et al. |
| 8,920,374 B2 | 12/2014 | Bokelman et al. |
| 9,101,723 B2 | 8/2015 | Larsen |
| 9,220,837 B2 | 12/2015 | Pesach et al. |
| 9,327,077 B2 | 5/2016 | Edwards et al. |
| 9,555,191 B2 | 1/2017 | Edwards et al. |
| 9,707,156 B2 | 7/2017 | Wengreen et al. |
| 9,775,957 B2 | 10/2017 | Despa et al. |
| 9,789,260 B1 | 10/2017 | Binier |
| 9,849,252 B2 | 12/2017 | Armes |
| 9,861,756 B1 | 1/2018 | Krasnow et al. |
| 9,867,941 B2 | 1/2018 | McLoughlin et al. |
| 9,872,633 B2 | 1/2018 | Limaye et al. |
| 9,901,674 B2 | 2/2018 | McLoughlin et al. |
| 9,911,308 B2 | 3/2018 | Edwards et al. |
| 9,919,112 B2 | 3/2018 | Hyde et al. |
| 2008/0269692 A1 | 10/2008 | Benton et al. |
| 2009/0030285 A1 | 1/2009 | Andersen |
| 2012/0293321 A1 | 11/2012 | Monroe |
| 2012/0323177 A1 | 12/2012 | Adams et al. |
| 2013/0184649 A1* | 7/2013 | Edwards .............. A61M 5/326 604/195 |
| 2015/0190575 A1 | 7/2015 | Lauchard et al. |
| 2015/0250413 A1 | 9/2015 | Redwood et al. |
| 2015/0290396 A1 | 10/2015 | Nagar et al. |
| 2015/0302173 A1 | 10/2015 | Forster |
| 2015/0189700 A1 | 12/2015 | Fisher et al. |
| 2015/0352281 A1 | 12/2015 | Pfrang |
| 2015/0374930 A1 | 12/2015 | Hyde et al. |
| 2016/0067739 A1 | 3/2016 | Jones |
| 2016/0129182 A1 | 5/2016 | Schuster et al. |
| 2016/0235911 A1* | 8/2016 | Cupicha ............ A61M 5/14248 |
| 2016/0263327 A1 | 9/2016 | Radmer et al. |
| 2016/0296699 A1* | 10/2016 | Cabiri ................. A61M 5/20 |
| 2016/0378951 A1 | 12/2016 | Gofman et al. |
| 2017/0119969 A1* | 5/2017 | McCullough ..... A61M 5/31568 |
| 2017/0162033 A1 | 6/2017 | Fisher et al. |
| 2017/0189625 A1 | 7/2017 | Cirillo et al. |
| 2017/0245943 A1 | 8/2017 | Foster et al. |
| 2017/0274149 A1 | 9/2017 | Aeschlimann |
| 2017/0286638 A1 | 10/2017 | Searle et al. |
| 2018/0014787 A1 | 1/2018 | Ganton et al. |
| 2018/0064784 A9 | 3/2018 | Sizer et al. |
| 2018/0093041 A1 | 4/2018 | McLoughlin et al. |
| 2018/0200452 A1 | 7/2018 | Marcoz et al. |
| 2018/0204636 A1 | 7/2018 | Edwards et al. |
| 2018/0211562 A1 | 7/2018 | Rios et al. |
| 2018/0214343 A1 | 8/2018 | Cantor |
| 2018/0280607 A1 | 10/2018 | Richards et al. |
| 2020/0155768 A1 | 5/2020 | Carpenter |
| 2021/0085880 A1* | 3/2021 | Steck ..................... G01P 15/18 |

FOREIGN PATENT DOCUMENTS

| | | |
|---|---|---|
| EP | 3381493 | 10/2018 |
| JP | 2009-511177 | 3/2009 |
| JP | 2013-521051 | 6/2013 |
| JP | 2017520298 B2 | 12/2015 |
| RU | 2618159 C2 | 5/2017 |
| WO | 2006116997 | 11/2006 |
| WO | 2007047200 | 4/2007 |
| WO | 07088444 | 8/2007 |
| WO | 2010019456 | 2/2010 |
| WO | 2011109205 | 9/2011 |
| WO | 2012155035 A1 | 11/2012 |
| WO | 2013034716 | 3/2013 |
| WO | 2013050535 | 4/2013 |
| WO | 2014143815 | 9/2014 |
| WO | 2015187797 | 12/2015 |
| WO | 2015187797 A1 | 12/2015 |
| WO | 2015187802 | 12/2015 |
| WO | 2016019375 | 2/2016 |
| WO | 2016033507 | 3/2016 |
| WO | 2016064916 | 4/2016 |
| WO | 2016115372 | 7/2016 |
| WO | 2016140853 | 9/2016 |
| WO | 2017071927 | 5/2017 |
| WO | 2017114908 | 7/2017 |
| WO | 2017215887 | 12/2017 |
| WO | 2018085952 | 5/2018 |
| WO | 2018178888 | 10/2018 |

OTHER PUBLICATIONS

"A Novel Actuator for Simulation of Epidural Anesthesia and Other Needle Insertion Procedures," Magill, John C., et al., *Simul Healthc*, Jun. 2010; 5(3); pp. 179-184.

Patent Cooperation Treaty International Search Report pertaining to International Application No. PCT/US2019/053438; International Filing Date: Sep. 27, 2019; dated Feb. 28, 2020.

Patent Cooperation Treaty Written Opinion of the International Searching Authority pertaining to International Application No. PCT/US2019/053438; International Filing Date: Sep. 27, 2019; dated Feb. 28, 2020.

"A Syringe Injection Rate Detector Employing a Dual Hall-Effect Sensor Configuration," Mukherjee, B., et al., Annual International Conference of the IEEE Engineering in Medicine and Biology Society. IEEE Engineering in Medicine and Biology Society. Conference Jul. 2013.

Tarun Agarwal, RF Transceiver Module With Block Diagram Explanation, Edgefx Tech Official Blog, https://www.edgefxkits.com/blog/rf-transceiver-module-with-block-diagram-explanation/ (Year: 2017).

* cited by examiner

CONNECTED INJECTION DEVICES WITH STATUS SENSING SYSTEMS

CROSS REFERENCE TO RELATED APPLICATIONS

This application is a continuation of, and claims priority under 35 U.S.C. 120 to, U.S. Non-Provisional application Ser. No. 16/764,294, filed May 14, 2020, which is a national Stage of International Application No. PCT/US2019/053438 filed Sep. 27, 2019, which claims priority to U.S. Provisional Application No. 62/740,539 filed Oct. 3, 2018 and U.S. Provisional Application No. 62/818,308 filed Mar. 14, 2019, the entire disclosures of which are hereby expressly incorporated by reference herein.

BACKGROUND

The present disclosure relates to medication delivery devices, and in particular, to status sensing systems used in connected medication delivery devices.

Injection devices in the form of a syringe or which include a syringe are widely employed by medical professionals and patients who self-medicate. Patients suffering from a number of different diseases frequently must inject themselves with medication and a variety of devices have been developed to facilitate such self-medication. In one example, the use of an automatic injection device which includes mechanisms to perform some of the steps of the injection process renders it more convenient for a patient to self-medicate particularly by patients with limited manual dexterity. Automatic injection devices are typically a single use device that is disposed after use.

SUMMARY

In one exemplary embodiment, an injection device assembly may include a device housing, a syringe assembly, a drive mechanism, and one or more main printed circuit boards (PCBs). The device housing may have a proximal end and a distal end, and may define an interior volume extending along a longitudinal axis between the proximal end and the distal end, and a proximal opening at the proximal end of the housing in communication with the interior volume. The device housing may comprise a user-graspable portion configured to be grasped by a hand of a user, the user-graspable portion extending a first radial distance outward from the longitudinal axis, and an outwardly flared end portion at the proximal end of the housing adjacent to the proximal opening. The outwardly flared end portion extends a second radial distance outward from the longitudinal axis that is greater than the first radial distance.

The syringe assembly may be at least partially disposed within the interior volume, and may include (i) a barrel configured to hold a medication, (ii) a piston configured to slide along the longitudinal axis within the barrel, and (iii) an injection needle extending from the barrel. The syringe assembly may be moveable relative to the housing along the longitudinal axis between a storage position where the injection needle extending from the barrel is concealed within the housing and an injection position where the injection needle projects proximally beyond the proximal opening.

The drive mechanism may be configured to move the syringe assembly from the storage position to the injection position, and to drive the piston proximally within the barrel so as to dispense the medication from the barrel in a dispensing event.

The one or more main PCB(s) may be disposed perpendicular to the longitudinal axis within the outwardly flared end portion of the device housing. The one or more main PCBs may define an opening through which at least a portion of the syringe assembly may be configured to pass during the dispensing event. The one or more main PCBs may extend a radial distance away from the longitudinal axis that is greater than the first radial distance. The one or more main PCBs may comprise at least one wireless radio frequency (RF) antenna and a processing circuit configured to transmit data wirelessly to an external device via the at least one wireless RF antenna.

In another exemplary embodiment, non-transitory computer-readable media may store instructions that, when executed by at least one processor of a mobile device, causes the at least one processor to perform the operations described herein. These operations may include receiving a wireless radio frequency (RF) transmission from an injection device assembly. The injection device assembly may comprise a device housing and one or more sensors. The device housing may have a proximal end, a distal end, and a longitudinal axis between the proximal end and the distal end, wherein the housing comprises a user-graspable portion configured to be grasped by a hand of a user, the user-graspable portion extending a first radial distance outward from the longitudinal axis, and the proximal end defines a proximal opening through which an injection needle is configured to pass. The one or more sensors may be positioned adjacent to the proximal opening, each sensor being configured to detect contact with skin tissue based on measured electrical resistance or capacitance. If there are a plurality of sensors, the plurality of sensors may surround the proximal opening. Each sensor may be located a radial distance outward from the longitudinal axis that is greater than the first radial distance.

If there are a plurality of skin contact sensors, the RF transmission from the injection device assembly (and received by the at least one processor of the mobile device) may comprise data showing which individual sensors of the plurality of sensors detect contact with skin tissue, and which individual sensors of the plurality of sensors do not detect contact with skin tissue. The operations may further comprise displaying on a display of the mobile device a schematic of the plurality of sensors and an indication showing which individual sensors of the displayed plurality of sensors detect contact with skin tissue, and which individual sensors of the displayed plurality of sensors do not detect contact with skin tissue.

In another exemplary embodiment, a method may indicate to a user how to properly position an injection device assembly. The method may comprise receiving, at a mobile device, a wireless radio frequency (RF) transmission from the injection device assembly. The injection device assembly may comprise a device housing and one or more sensors. The device housing may have a proximal end, a distal end, and a longitudinal axis between the proximal end and the distal end, wherein the housing comprises a user-graspable portion configured to be grasped by a hand of a user, the user-graspable portion extending a first radial distance outward from the longitudinal axis, and the proximal end defines a proximal opening through which an injection needle is configured to pass. The one or more sensors may be positioned adjacent to the proximal opening, each sensor being configured to detect contact with skin tissue based on measured electrical resistance or capacitance. If there are a plurality of sensors, the plurality of sensors may surround the proximal opening. Each sensor may be located a radial distance outward from the longitudinal axis that is greater than the first radial distance.

If there are a plurality of skin contact sensors, the RF transmission from the injection device assembly (and received by the at least one processor of the mobile device) may comprise data showing which individual sensors of the plurality of sensors detect contact with skin tissue, and which individual sensors of the plurality of sensors do not detect contact with skin tissue. The method may further comprise displaying on a display of the mobile device a schematic of the plurality of sensors and an indication showing which individual sensors of the displayed plurality of sensors detect contact with skin tissue, and which individual sensors of the displayed plurality of sensors do not detect contact with skin tissue.

In another exemplary embodiment, an injection device assembly may include a housing, a syringe assembly at least partially disposed within the housing, a drive mechanism configured to drive the syringe assembly from a storage position to an injection position, one or more skin-contact sensors, each sensor being configured to detect contact with skin tissue, and an accelerometer disposed within the housing and configured to output a signal representative of sensed acceleration. The device assembly may further include a processing circuit configured to analyze the signal output by the accelerometer to detect acceleration spikes, and determine that a first acceleration spike detected in the signal output by the accelerometer is caused by initiation of a dispensing event in which the syringe assembly is driven by the drive mechanism from the storage position to the injection position only when at least one of the one or more skin-contact sensors detect contact with skin tissue at the time the first acceleration spike was detected. The device assembly may also include a retraction mechanism configured to drive the syringe assembly from the injection position to a retracted position, wherein the processing circuit is further configured to determine that a second acceleration spike detected by the accelerometer subsequent to the first acceleration spike is caused by a retraction movement upon completion of the dispensing event in which the syringe assembly is driven by the retraction mechanism from the injection position to the retracted position only when at least one of the one or more skin-contact sensors detect contact with skin tissue at the time the second acceleration spike was detected.

In another exemplary embodiment, a method for determining initiation of a dispensing event may comprise: providing an injection device assembly, the assembly comprising: a housing, a syringe assembly at least partially disposed within the housing, a drive mechanism configured to drive the syringe assembly from a storage position to an injection position, one or more skin-contact sensors, each sensor being configured to detect contact with skin tissue, and an accelerometer disposed within the device assembly, and configured to output a signal representative of sensed acceleration. The method may further comprise determining, by at least one processing circuit, whether at least one of the one or more skin-contact sensors detect contact with skin tissue; analyzing, by the at least one processing circuit, the signal output by the accelerometer to detect a first acceleration spike; determining, by the at least one processing circuit, that the first acceleration spike is caused by initiation of a dispensing event in which the syringe assembly is driven by the drive mechanism from the storage position to the injection position only when at least one of the one or more skin-contact sensors detect contact with skin tissue at the time the first acceleration spike was detected. The injection device assembly may further comprise a retraction mechanism configured to drive the syringe assembly from the injection position to a retracted position. The method may also further comprise analyzing, by the at least one processing circuit, the signal output by the accelerometer to detect a second acceleration spike subsequent to the first acceleration spike; and determining, by the at least one processing circuit, that the second acceleration spike is caused by a retraction movement upon completion of the dispensing event in which the syringe assembly is driven by the retraction mechanism from the injection position to the retracted position only when at least one of the one or more skin-contact sensors detect contact with skin tissue at the time the second acceleration spike was detected.

In another embodiment, an injection device assembly may comprise a housing, a syringe assembly at least partially disposed within the housing, a drive mechanism configured to drive the syringe assembly from a storage position to an injection position to dispense medication, one or more skin-contact sensors, each sensor being configured to detect contact with skin tissue, and an accelerometer disposed within the device assembly and configured to output a signal representative of sensed acceleration. The injection device assembly may further comprise a processing circuit operably coupled with one or more skin-contact sensors and the accelerometer configured to analyze the signal output by the accelerometer to detect a first acceleration spike and a second acceleration spike subsequent to the first acceleration spike. The processing circuit may also be configured to determine that a dispensing event has been completed when a set of one or more conditions are satisfied, wherein the set of conditions comprises the following condition: at least one of the one or more skin-contact sensors detect contact with skin tissue at least once during a time period beginning with the first acceleration spike and ending with the second acceleration spike. The processing circuit may also be configured to determine that the dispensing event has not been completed when at least one condition in the set of conditions is not satisfied. The injection device assembly may further comprise a retraction mechanism configured to retract the syringe assembly from the injection position to a retracted position at the end of the dispensing event. In some embodiments, the retraction mechanism be the same mechanism as, or share components with, the drive mechanism.

In another embodiment, a method for determining completion of a dispensing event may comprise providing an injection device assembly, the assembly comprising: a housing, a syringe assembly at least partially disposed within the housing, a drive mechanism configured to drive the syringe assembly from a storage position to an injection position to dispense medication, one or more skin-contact sensors, each sensor being configured to detect contact with skin tissue, and an accelerometer disposed within the device assembly and configured to output a signal representative of sensed acceleration. The method may further comprise analyzing the signal output by the accelerometer to detect a first acceleration spike and a second acceleration spike subsequent to the first acceleration spike, and determining whether a dispensing event has been completed. This determination may comprise determining that the dispensing event has been completed when a set of one or more conditions are satisfied, wherein the set of conditions comprise the following condition: at least one of the one or more skin-contact sensors detect contact with skin tissue at least once during a time period beginning with the first acceleration spike and ending with the second acceleration spike, and determining that the dispensing event has not been completed when at least one condition in the set of conditions is not satisfied. The injection device assembly may further comprise a retraction mechanism configured to retract the syringe assembly from the injection position to a retracted position at the end of the dispensing event. In some embodiments, the retraction mechanism may be the same mechanism as, or share common components with, the drive mechanism.

In another embodiment, an injection device assembly may comprise a housing; a syringe assembly at least partially disposed within the housing, the syringe assembly including a barrel configured to hold a medication; a drive mechanism configured to dispense the medication from the barrel when activated; a thermal ballast; a temperature sensor configured to measure a temperature of the thermal ballast; and at least one processing circuit configured to estimate the temperature of the medication in the barrel based on the temperature of the thermal ballast.

In yet another embodiment, a method for estimating a temperature of a medication in an injection device assembly may comprise: providing the injection device assembly, the assembly having: a housing, a syringe assembly at least partially disposed within the housing, the syringe assembly including a barrel configured to hold a medication, a drive mechanism configured to dispense the medication from the barrel when activated, a thermal ballast, and a temperature sensor configured to measure a temperature of the thermal ballast. The method may further comprise receiving, at one or more processing circuits, the measured temperature of the thermal ballast; and estimating the temperature of the medication in the barrel based on the measured temperature of the thermal ballast.

BRIEF DESCRIPTION OF THE DRAWINGS

The above mentioned and other features of this present disclosure, and the manner of attaining them, will become more apparent and the invention itself will be better understood by reference to the following description of embodiments of the present disclosure taken in conjunction with the accompanying drawings, wherein.

Figure 1:
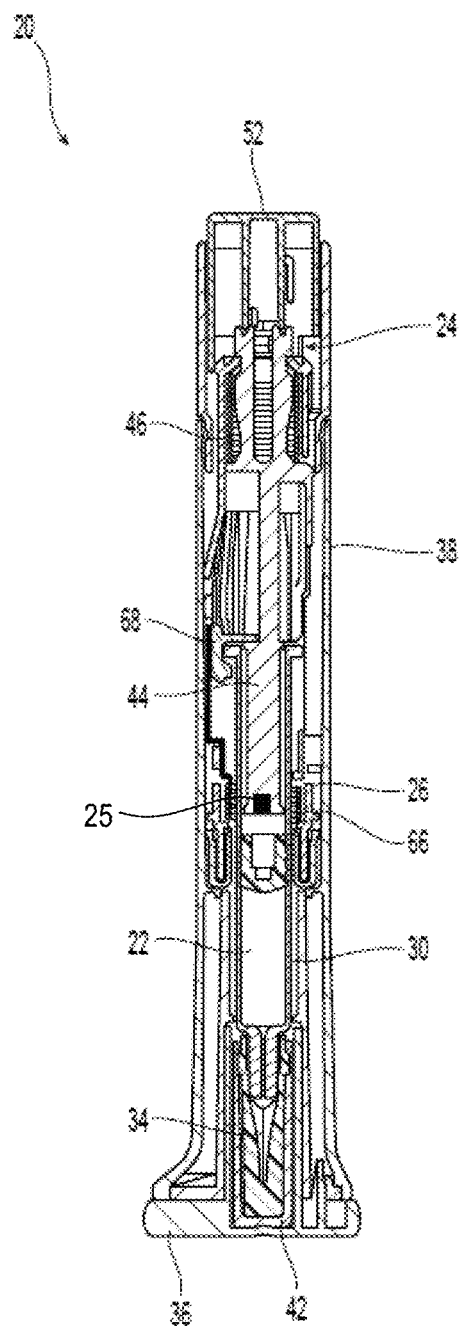
FIG. 1 is a cross sectional view of an injection device prior to use.

Corresponding reference characters indicate corresponding parts throughout the several views. Although the exemplification set out herein illustrates embodiments of the present disclosure, in several forms, the embodiments disclosed below are not intended to be exhaustive or to be construed as limiting the scope of the invention to the precise forms disclosed.

DETAILED DESCRIPTION

The present disclosure relates to sensing systems for medication delivery devices. Sensing systems may be integrated within the delivery device, or be incorporated into a removable module that attaches to the delivery device. Such sensing systems may be configured to determine the current operational status of the device by sensing various parameters or signals representative of the device's operational status.

In some embodiments, sensing systems may sense the location or movement of device components relative to other device components. For example, such sensing systems may track the location and/or movement of a plunger used to expel medication from the medication delivery device. By tracking the location or movement of the plunger, the medication delivery device may determine how much medication has been expelled, the rate at which medication is being expelled, and/or when the medication within the delivery device has been completely delivered. Such sensing systems may utilize various types of sensors, such as a visual sensor that tracks movement of said device components, an optical or radiation sensor that detects when a device component enters or exits a detection zone targeted by the sensing system, a magnetic field sensor that detects changes in sensed magnetic field caused by movement of device components, or one or more accelerometers that detect movement of device components.

In some embodiments, sensing systems may determine the orientation of the device. The determined orientation may be used to determine whether the medication delivery device is properly oriented to deliver the medication—for example, the delivery device may warn its user or prevent delivery of medication when the device is oriented upside down, or in any orientation that makes safe and reliable delivery of medication difficult or impossible. Such sensing systems may utilize one or more accelerometers, disposed at one or more locations on the device, which are configured to determine the direction of gravitational pull. The sensing systems may also comprise a processor circuit configured to determine the orientation of the device around one, two, or three orientation axes based on readings from the accelerometers.

In some embodiments, sensing systems may measure a temperature of a medication stored within the medication delivery device. Certain medications may need to be stored at a first (e.g., lower) temperature range to avoid spoliation, but be brought to a second (e.g., higher) temperature range prior to delivery into a patient's body. Temperature sensing systems may be used to monitor the temperature of the medication within the delivery device when it is being stored, and ensure that it has not been exposed to unsafe temperatures that may have rendered the medication unfit for consumption. Temperature sensing systems may also be used to warn users when the temperature of the medication is approaching unsafe levels. When the device is being prepared for use, sensing systems may be used to determine when the temperature of the medication has been brought within the second temperature range. The medication delivery device may then inform a user that the medication is ready to be delivered, e.g., by using a visual indicator (e.g., by lighting and/or extinguishing one or more LEDs), an auditory indicator (e.g., an announcement or tone output from a speaker), or a wireless signal transmitted to an external mobile device, which in turn informs the user. Such temperature sensing systems may utilize any of a plurality of types of sensors to measure temperature of the medication, such as an infrared sensor or a thermistor.

In some embodiments, sensing systems may include one or more sensors configured to determine when and/or which portions of the medication delivery device are in contact with a patient's skin. The medication delivery device may use such sensing systems to determine when the device is properly positioned to inject the medication into the patient's body. Such sensing systems may include one or more sensors configured to measure electrical resistance or capacitance, and processing circuitry configured to determine, based on the measured resistance or capacitance, when an individual sensor is in contact with human tissue such as skin. In cases where the sensing systems includes a plurality of sensors, the systems may be configured to determine which individual sensors of the plurality of sensors are in contact with human tissue. Such sensing systems may also include temperature sensors, similar to those discussed above, that are configured to determine when the sensor is in contact with human tissue.

Sensing systems may determine the current operational status of the device. This current status may be communicated to a user, for example, via visual, auditory, or haptic indicators integrated with or physically attached to the delivery device, such as one or more displays, LEDs, speakers, or vibration motors. This current status may also be communicated to a user by sending data regarding the current status to an external device via a wired or wireless communication link—the external device, in turn, may communicate the current status to the user. For example, in some embodiments, the medication delivery device may comprise a short-range, wireless communication interface, such as a Near Field Communication (NFC), Bluetooth, and/or Bluetooth Low Energy (BLE) communication circuit, that transmits data regarding the delivery device's current operational status to an external device. This external device may be an electronic computing device configured to execute software and/or firmware to receive and process the data, and communicate the delivery device's operational status to a user. Exemplary external devices include a mobile handheld device (e.g., a smartphone, a mobile phone, a pager, a personal digital assistant (PDA), a tablet, and the like), a wearable device (e.g., a smart watch, or an augmented- or virtual-reality device), a portable general-purpose computer (e.g., a laptop), or a desktop general-purpose computer. When the user is informed of the operational status of the device, the user is less likely to take an action which might compromise the effective use of the device, such as removing the device from the injection site before completion of the drug delivery, or delivering the drug before it has warmed to the appropriate delivery temperature. By way of illustration, the medication delivery device is described in the form of an auto-injector device. However, the medication delivery device may be any device which is used to deliver a dose of a medication, such as pen injectors, infusion pumps and syringes. The medication may be any of a type that may be delivered by such a medication delivery device.

It may be advantageous to provide a single sensing system positioned along the device to capture at least one of a needle guard present state, an injection ready state, a needle insertion state, a drug delivered state, and a needle retraction state, or any combination thereof. It may be beneficial to determine whether the dose was delivered and/or the operational states during the injection process with a module without having to change the mechanical architecture of the drive mechanism of the delivery device.

Figure 2:
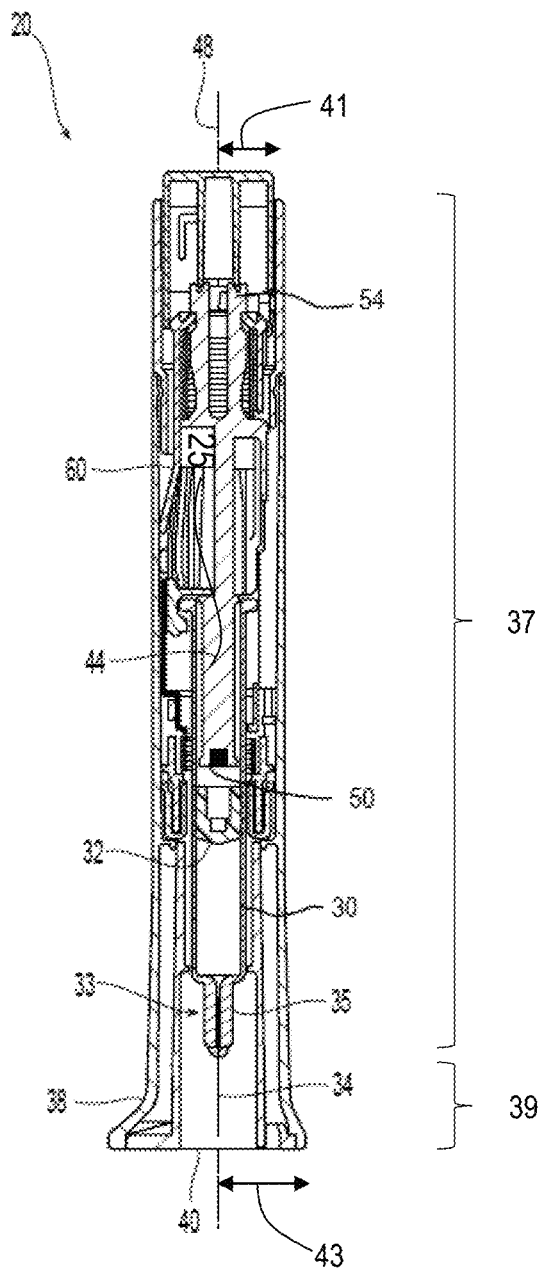
FIG. 2 is a cross sectional view of the injection device with the syringe assembly in a storage position and ready for an injection event.
Figure 3:
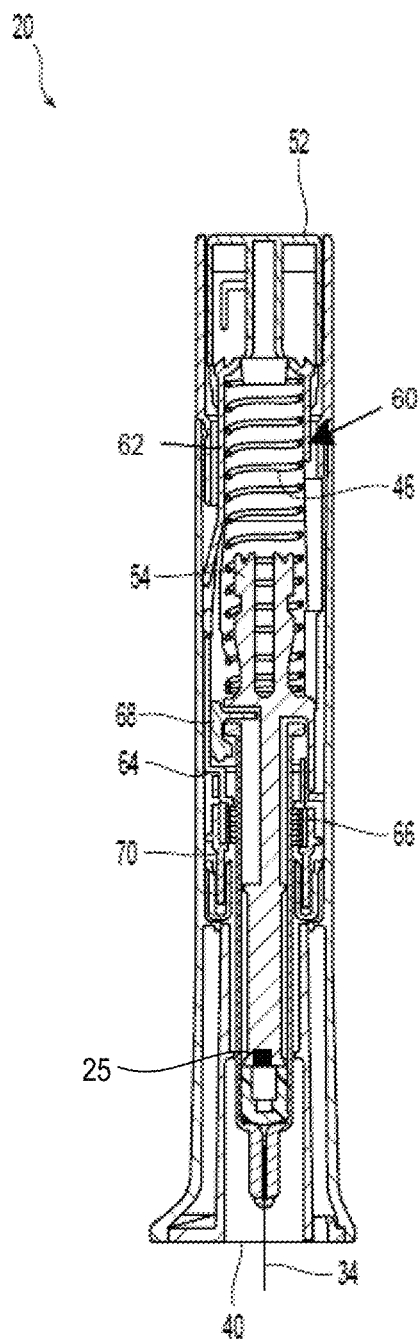
FIG. 3 is a cross sectional view of the injection device with the syringe assembly in an injection position.

In FIGS. 1-3, a medication injection device 20 is depicted in various operational states. One example of such a device and its operation is described in U.S. Pat. No. 8,734,394 B2 issued May 27, 2014 to Adams et al., the entire disclosure of which is hereby incorporated herein by reference. Device 20 includes a syringe assembly 22, a drive mechanism 24, and a retraction mechanism 26, and may include one or more main printed circuit boards (PCBs) 82 and/or one or more secondary PCBs 84 shown later, for example, in FIGS. 8, 9A, 9B, 10A and 10B. Syringe assembly 22 includes a barrel 30 forming a container body for holding a medication, and a piston 32 disposed within the barrel 30 for driving the medication outside the barrel. Syringe assembly 22 also includes a needle assembly 33 having a hollow injection needle 34 and a needle hub 35 which mounts needle 34 to syringe barrel 30. Advancing piston 32 within barrel 30 toward needle 34 dispenses medication through needle 34.

Devices described herein, such as device 20, may further comprise a medication, such as for example, within the syringe barrel 30. In another embodiment, a system may comprise one or more devices including device 20 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies including but not limited to IL-23 antibody analogs or derivatives, such as mirikizumab, IL-17 antibody analogs or derivatives, such as ixekizumab, therapeutic agents for pain-related treatments, such as galcanzeumab or lasmiditan, and any therapeutic agent that is capable of delivery by the devices described herein. The medication as used in the device may be formulated with one or more excipients. The device is operated in a manner generally as described above by a patient, caregiver or healthcare professional to deliver medication to a person.

Figure 8:
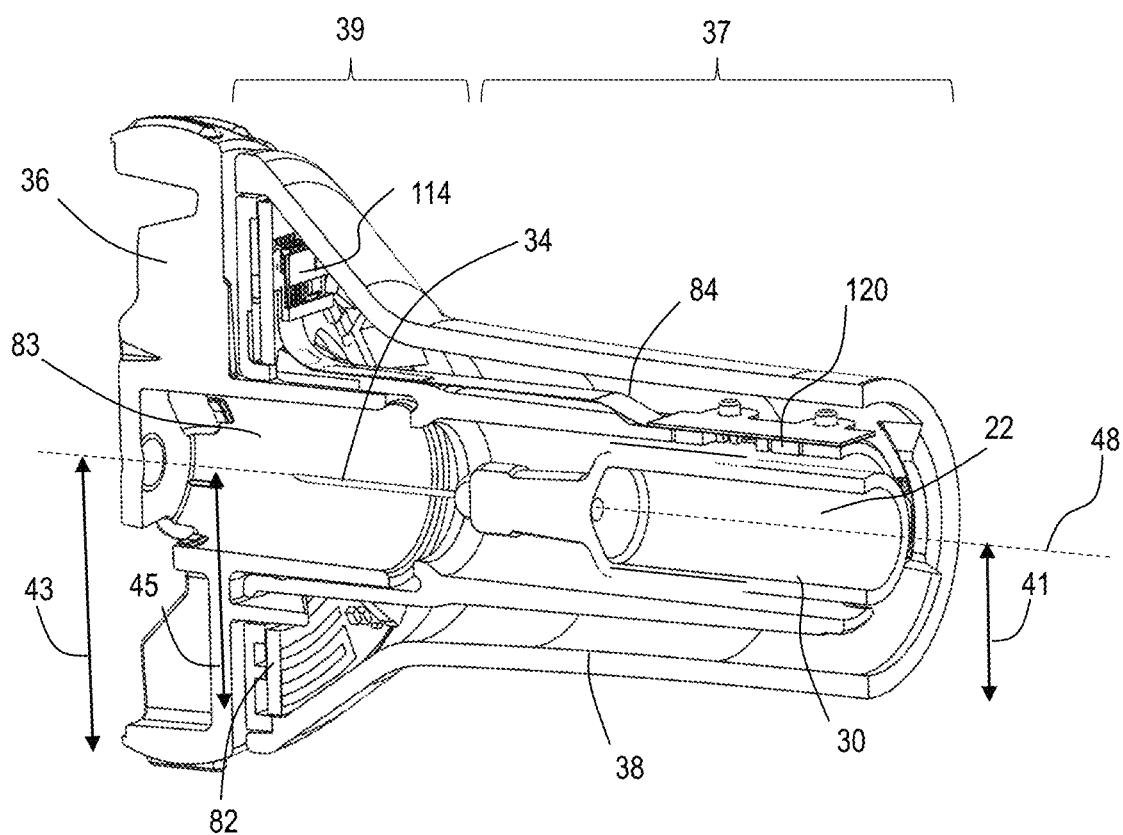
FIG. 8 is a cross sectional view of the injection device illustrating a placement of one or more main PCBs within an end portion of the injection device's housing, according to a first set of embodiments.
Figure 16A:
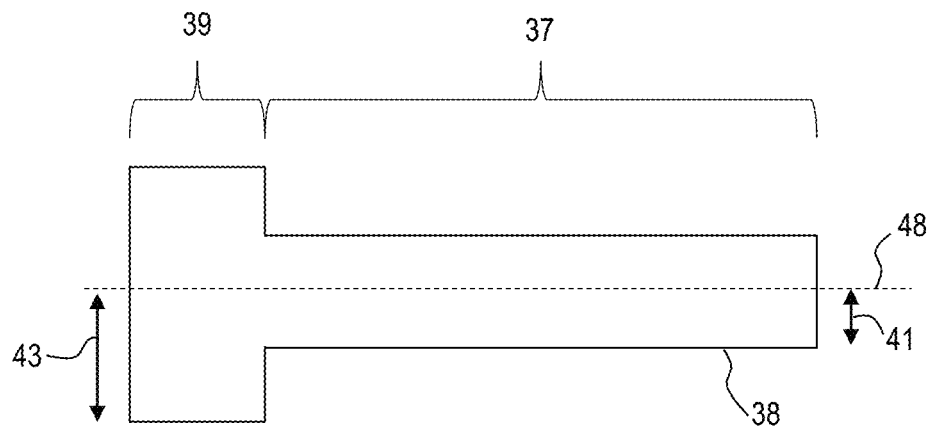
FIGS. 16A, 16B, and 16C are views of alternative shapes for an outwardly flared end portion of an injection device housing, according to any of the first, the second, and the third set of embodiments.
Figure 16B:
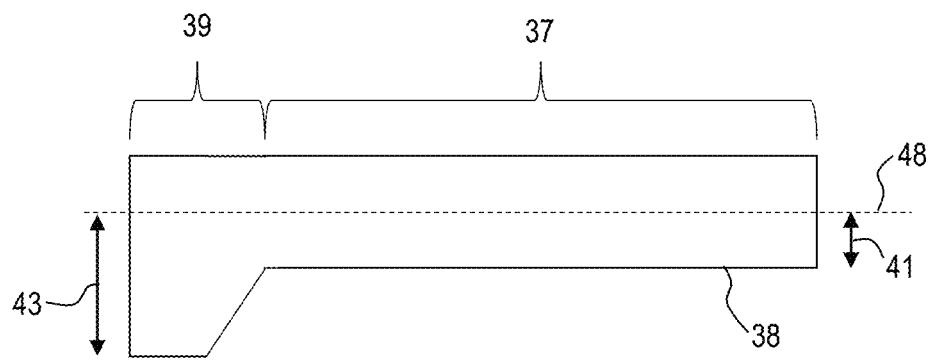
Figure 16C:
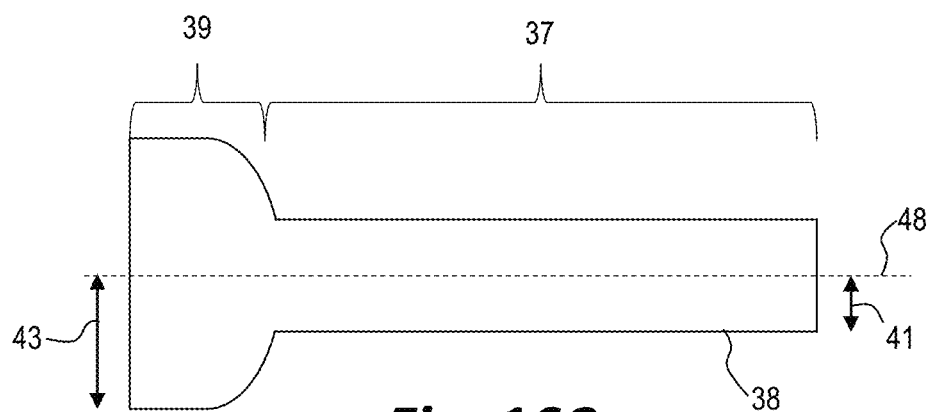

FIG. 1 illustrates device 20 in its initial, pre-use configuration. Here, an end cap 36 is secured to an injection device housing 38 and covers a proximal end opening 40 in housing 38. As used herein, distal and proximal refer to axial locations relative to an injection site when the apparatus is oriented for use at such site, whereby, for example, proximal end of the housing refers to the housing end that is closest to such injection site, and distal end of the housing refers to the housing end that is farthest from such injection site. Housing 38 may be formed from a plastic material and is shown extending generally longitudinally between a distal end in close proximity to an actuating button 52 and a proximal end in close proximity to the proximal end opening 40 along a longitudinal axis 48. As shown in FIGS. 2 and 8, housing 38 may comprise a user-graspable portion 37 configured to be grasped by a hand of a user, the user-graspable portion 37 extending a radial distance 41 outward from longitudinal axis 48. In some embodiments, the radial distance 41 may be between 5-10 mm in length (e.g., in some embodiments, 5-8 mm may be a suitable length). Also as shown in FIGS. 2 and 8, housing 38 may also comprise an outwardly-flared end portion 39 at a proximal end of the housing adjacent the proximal opening 40. The end portion extends a radial distance 43 outward from longitudinal axis 48 that is greater than the radial distance 41. In some embodiments, the radial distance 43 may be greater than 10 mm in length. For example, in some embodiments, the radial distance 43 may be between 10-20 mm in length (e.g., in some embodiments, 15-20 mm may be a suitable length). End portion 39 may slope smoothly radially outward from the user-graspable portion 37, as shown in FIGS. 1-3. In other embodiments, end portion 39 may take the form of other shapes. FIGS. 16A-C show several exemplary alternative shapes for end portion 39, but end portion 39 may take on any shape that extends a radial distance 43 away from longitudinal axis 48 that is greater than the radial distance 41 of the user-graspable portion.

A needle guard 42 is mounted on syringe assembly 22 and covers and surrounds needle 34. End cap 36 and needle guard 42 protect the user from accidental needle pricks and also protect needle 34 from damage. When using device 20 to dispense medication, for example, injecting the medication into a patient, end cap 36 and needle guard 42 are first removed. FIG. 2 illustrates device 20 after removal of end cap 36 and needle guard 42 from syringe assembly 22, wherein the syringe assembly is in a storage position and device 20 is ready for a dispensing event.

Syringe assembly 22 is moveable relative to the injection device 20 between a storage position and an injection position. FIG. 3 illustrates device 20 after the syringe assembly 22 has been moved relative to device 20 to an injection position from its storage position that is shown in FIG. 2. In the storage position (FIGS. 1 and 2), needle 34 is retracted to a position such that needle 34 is disposed within housing 38 of device 20. In the injection position (FIG. 3), needle 34 projects outwardly from housing 38 beyond proximal opening 40 in the proximal direction parallel to longitudinal axis 48 whereby needle 34 may be inserted into a patient.

Drive mechanism 24 includes a plunger 44 which engages piston 32. Drive mechanism 24 includes a spring 46 that drives plunger 44 in a translational movement. In the illustrated embodiment, spring 46 advances plunger 44 along a linear path defined by the longitudinal axis 48 of device 20. As plunger 44 is advanced, foot 50 of plunger 44 contacts piston 32. As the plunger 44 is further advanced, syringe assembly 22 is advanced along axis 48 from its storage position to its injection position. After advancement of syringe assembly 22 to its injection position, the continued proximal advancement of plunger 44 advances piston 32 proximally within barrel 30 from its initial piston position (shown in FIGS. 1 and 2) to its final piston position (shown FIG. 3) to cause medication to be dispensed from needle 34 in a dispensing event. Prior to any dispensing of medication and when syringe barrel 30 holds the full original volume of medication, piston 32 will be in its initial piston position. After advancing piston 32 the full extent of its travel length toward needle assembly 33, piston 32 will be in its final piston position proximate needle assembly 33 and the medication from within barrel 30 will have been discharged. In a single use, syringe assembly 22 will hold a single dose of medication which will be delivered in a single injection event and piston 32 will be advanced from its initial piston position to its final piston position in that single injection event to thereby deliver the entire single dose contents of syringe assembly 22. While the device is shown as a single use device, multiple-use devices may also benefit from status indication of the device during a single use.

The advancement of plunger 44 will generally not result in the dispensing of medication from syringe assembly 22 until after syringe assembly 22 has been advanced to the injection position. There are factors that may inhibit the medication from being dispensed before the syringe is advanced to the injection position. A factor may be the friction between piston 32 and barrel 30. Typically, piston 32 will be formed out of a rubber material and barrel 30 will be glass. The frictional resistance between these two components may be sufficient to prevent the advancement of piston 32 within barrel 30 until syringe assembly 22 is advanced to its injection position and engagement with a suitable stop member prevents the further advancement of syringe assembly 22. Additionally, the medication within the syringe may be somewhat viscous and thereby somewhat resistant to flowing out of needle 34. If necessary, modification of piston 32 and syringe barrel 30 to alter the frictional resistance of dispensing motion of the engagement member 32 relative to syringe barrel 30 may limit or prevent the premature dispensing of medication before container 22 reaches its injection position.

Plunger 44 may include a magnet 25 adjacent foot 50. As shown in FIGS. 1-3, magnet 25 is configured to maintain a fixed axial distance from piston 32. Magnet 25 emits a magnetic field that is sensed by magnetometers 118 and 112, discussed below in relation to FIGS. 9A, 9B, and 11.

Figure 4:
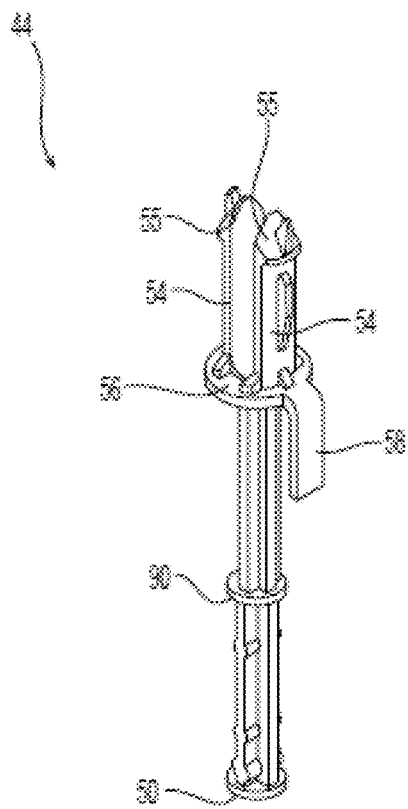
FIG. 4 is a perspective view of a plunger.

To activate drive mechanism 24, a person depresses actuating button 52 at the distal end of device 20. Depressing button 52 disengages one or two elongate prongs 54 on plunger 44 (shown in FIG. 4) from a shuttle assembly 60 thereby allowing spring 46 to axially advance plunger 44. Spring 46 has a helical shape and surrounds prongs 54. The proximal end of spring 46 biasingly engages flange 56 on plunger 44.

Figure 6:
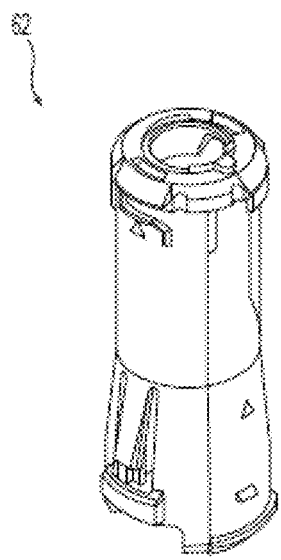
FIG. 6 is a perspective view of an upper shuttle member.
Figure 7:
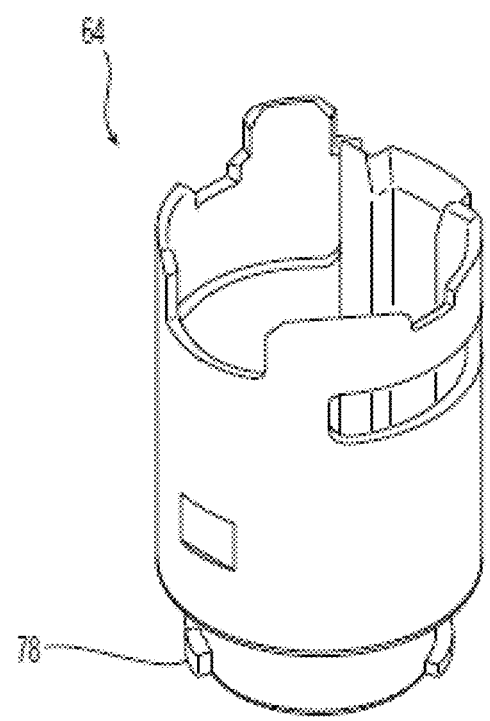
FIG. 7 is a perspective view of a lower shuttle member.

Shuttle assembly 60 may include an upper shuttle member 62 shown in FIG. 6 and a lower shuttle member 64 shown in FIG. 7. Shuttle members 62, 64 are fixed together in the final assembly. In the final assembly, upper shuttle member 62 captures button 52 and spring 46 limiting the axial movement of these parts in the distal direction. Prongs 54 engage surfaces on upper shuttle 62 when the device is in the condition shown in FIGS. 1 and 2. Depressing button 52 causes tabs on button 52 to engage ramps 55 on prongs 54 to bias prongs 54 inwardly to disengage prongs 54 from upper shuttle member 62. After prongs 54 have been disengaged, spring 46 exerts a biasing force on flange 56 to advance plunger 44 from the position shown in FIG. 2 to the position shown in FIG. 3. As plunger 44 is advanced, it moves syringe assembly 22 to the injection position and then advances piston 32 to dispense medication as discussed above.

After the dispensing event is complete, retraction mechanism 26 optionally moves syringe assembly 22 from the injection position shown in FIG. 3 back to a retracted position. More specifically, the retraction mechanism is adapted to move the medication container from the injection position to the retracted position in a retraction movement. The retracted position may be similar to the storage position in that the syringe assembly is drawn back into the housing 38 such that needle 34 no longer projects proximally from proximal opening 40 and is disposed entirely within housing 38. In some embodiments, the retracted position may be the same as the storage position. In other embodiments, however, a syringe assembly 22 in the retracted position may be located slightly proximal or distal to a syringe assembly in the storage position. In the illustrated embodiment, the retraction mechanism includes a spring 66, a syringe carrier 68 shown in FIG. 5 and a rotary member 70 that acts as a follower. In yet other embodiments, the device 20 may include no retraction mechanism 26 such that the syringe assembly remains in its injection position indefinitely after the medication has been dispensed, until the syringe assembly is manually removed or repositioned by a user.

Plunger 44 may include an outrigger 58 which unlocks rotary member 70 as plunger 44 nears the end of its travel in the proximal direction. Rotary member 70 is rotationally secured to lower shuttle member 64 by engagement between a latch and a latching recess in lower shuttle member 64. Outrigger 58 unlocks member 70 by depressing the latch. Spring 66 is torsionally preloaded and has one end engaged with member 70 and an opposite end engaged with shuttle assembly 60. Upon depression of the latch, spring 66 causes member 70 to rotate. With additional reference to FIG. 7, member 70 may include a slot that receives a tab 78 on lower shuttle member 64. At one end of the slot, member 70 defines an axially extending channel. As member 70 is rotated, tab 78 may move within the slot on member 70 until tab 78 reaches the axially extending channel.

Member 70 is rotatable within housing 38 but is not axially moveable relative to housing 38. Other embodiments may include a member 70 that is also axially movable. A radial flange on rotary member 70 may engage a ledge within housing member 38 to limit the proximal movement of member 70. Spring 66 may exert an axial force, torsional force, or both forces on member 70 to bias member 70 proximally to thereby maintain member 70 in an axial position where the radial flange of member 70 engages the interior ledge of housing member 38. Shuttle assembly 60 may include axially extending channels or ribs that engage corresponding features on housing member 38 that allow shuttle assembly 60 to move axially within housing 38 but which prevent the relative rotation of shuttle assembly 60 relative to housing member 38.

Spring 66 is also axially preloaded and exerts a distally directed biasing force on shuttle assembly 60. When tab 78 reaches the axially extending channel, spring 66 moves shuttle assembly 60 distally within housing 38 as tab 78 slides axially through the channel. A damping compound may be arranged adjacent rotary member 70 to slow the rotation of member 70 and allow for the completion of the dispensing event before tab 78 reaches the axially extending channel. For example, rotary member 70 may include a skirt with a plurality of axially extending tabs that are disposed in a grease collar to provide damping.

As shuttle assembly 60 moves distally, it carries syringe assembly 22 distally and moves it back to the storage position shown in FIG. 2. Spring 66 biases the retraction mechanism 26 distally and thereby maintains syringe assembly 22 in its retracted position after an injection event. A locking mechanism such as a detent on the shuttle assembly 60 and a recess on the housing 38 member may additionally provide a locking engagement to secure syringe assembly 22 in the retracted position with needle 34 disposed within housing 38 after an injection event whereby the user may then dispose or otherwise handle device 20 in a safe manner.

Figure 5:
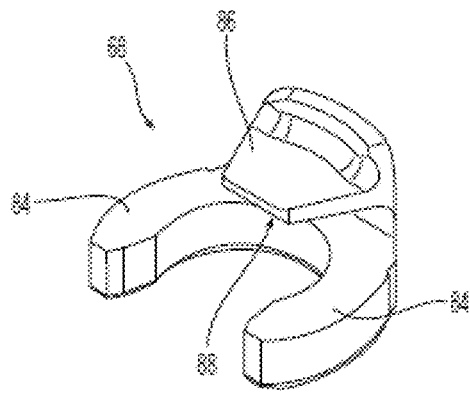
FIG. 5 is a perspective view of a syringe carrier.

Syringe carrier 68 is shown in FIG. 5. Arcuate arms 84 of carrier may grip barrel 30 of syringe assembly 22. Syringe carrier 68 also includes a flange 86. A flange on the syringe barrel 30 is captured between arms 84 and flange 86. A portion of the underside 88 of flange 86 engages small flange 90 on plunger 44 and thereby prevents proximal axial movement of syringe assembly 22 before plunger 44 is advanced. When shuttle 60 is being retracted, lower shuttle member 64 engages arms 84 to carry syringe assembly 22 distally to its retracted position.

Although FIGS. 1-7 depict and describe an exemplary drive mechanism 24 and an exemplary retraction mechanism 26, other mechanisms may also be used to drive syringe assembly 22 from the storage position to the injection position, and/or from the injection position to the retracted position. Such drive and/or retraction mechanisms may (but need not) include one or more springs or deformable parts that store energy when they are held in a pre-triggered state and, when triggered, release said stored energy to drive the syringe assembly from the storage position to the injection position, and/or from the injection position to the retracted position. Such mechanisms may (but need not) include mechanisms that generate motive force using chemical reactions or processes, e.g., by generating gas through the mixture of two or more reagents, or by igniting a small amount of combustible or explosive material. Such chemically-driven mechanisms may comprise one or more storage containers for the chemical reagents, a trigger that punctures or opens said storage containers, allows said reagents to mix, and/or which provides a spark or other ignition source for beginning the chemical reaction, and a movable piston or other component that moves in response to increasing gas pressure generated by the resulting chemical reaction. Such mechanisms may (but need not) include mechanisms that use stored electrical power (e.g., in a battery) to run electric motors that drive and/or retract the syringe assembly, or to trigger other physical or chemical mechanisms. Such mechanisms may (but need not) include hydraulic or pneumatic systems (e.g., tubes), gears, cables, pulleys, or other known components for transferring kinetic energy from one component to another. In some embodiments, rather than having separate mechanisms for driving the syringe assembly and then retracting the syringe assembly, a single mechanism may be configured to both drive and then retract the syringe assembly.

FIG. 8 illustrates an exemplary placement of one or more main PCBs 82 within the end portion 39, according to a first set of embodiments of device 20. The one or more main PCBs may be arranged perpendicular to the longitudinal axis 48, and may be stacked on top of each other, and/or may be arranged next to each other on the same plane perpendicular to the longitudinal axis 48. The main PCB(s) define an opening 83 through which injection needle 34 of syringe assembly 22 is configured to pass, for example, when end cap 36 is removed and the injection needle is driven proximally to inject the patient during a dispensing event. As shown, the main PCB(s) extend a radial distance 45 away from the longitudinal axis 48 that is greater than the radial distance 41 of the user-graspable portion 37. FIG. 8 also shows one or more secondary PCBs 84 that extend substantially perpendicular to the main PCBs and parallel to the longitudinal axis 48—secondary PCB(s) may be communicatively coupled to the main PCB(s) via one or more PCB connectors 114. While secondary PCB(s) 84 may mount additional sensing systems, such secondary PCBs are optional and may be excluded in certain embodiments to decrease manufacturing complexity and costs.

End portion 39 may be an advantageous location and size within device 20 to place the main PCB(s). The increased footprint of end portion 39 is created by the radial extension of the end portion by a radial distance 43 outward from longitudinal axis 48 that is greater than the radial distance 41 of the user-graspable portion. From the increased footprint, there is more space to house the main PCB(s) and its various components than other locations in device 20. To this end, many components can be preassembled to the main PCB that is disposed in the advantageous location of the end portion 39. As a result, incorporating the main PCB(s) in end portion 39 may require little or no alteration to the shape of previously-existing auto-injectors' housing, which decreases disruption to manufacturing processes and reduces manufacturing costs. Furthermore, placing the main PCB(s) in end portion 39 allows skin contact sensors 122, 123, and 124 to be located farther away from longitudinal axis 48, which increases the reliability of skin contact readings received from these sensors.

Figure 9A:
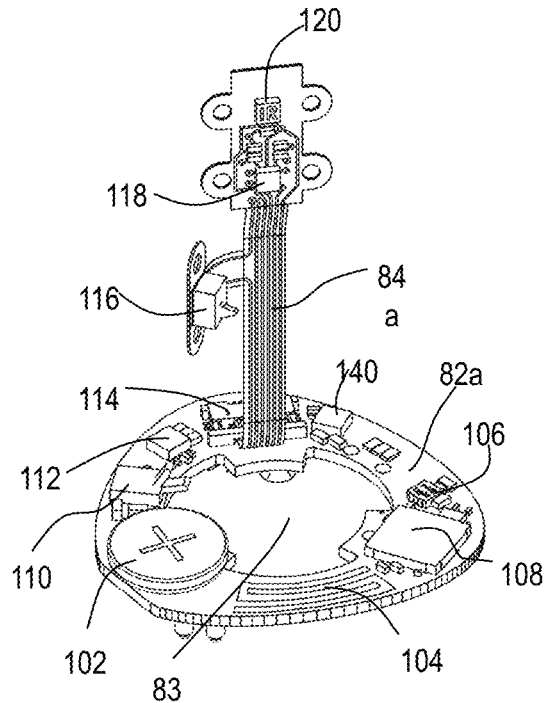
FIG. 9A is a top (i.e., distal) perspective view of a main PCB and a secondary PCB, according to the first set of embodiments.
Figure 9B:
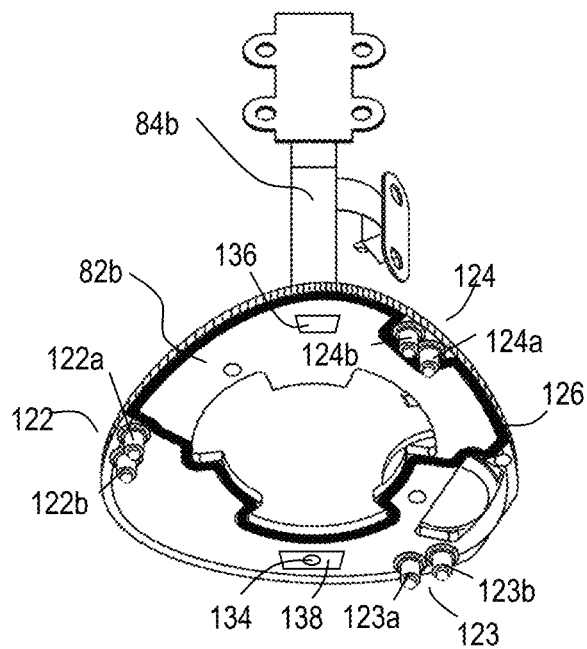
FIG. 9B is a bottom (i.e., proximal) perspective view of the main PCB and the secondary PCB of the first set of embodiments.
Figure 10A:
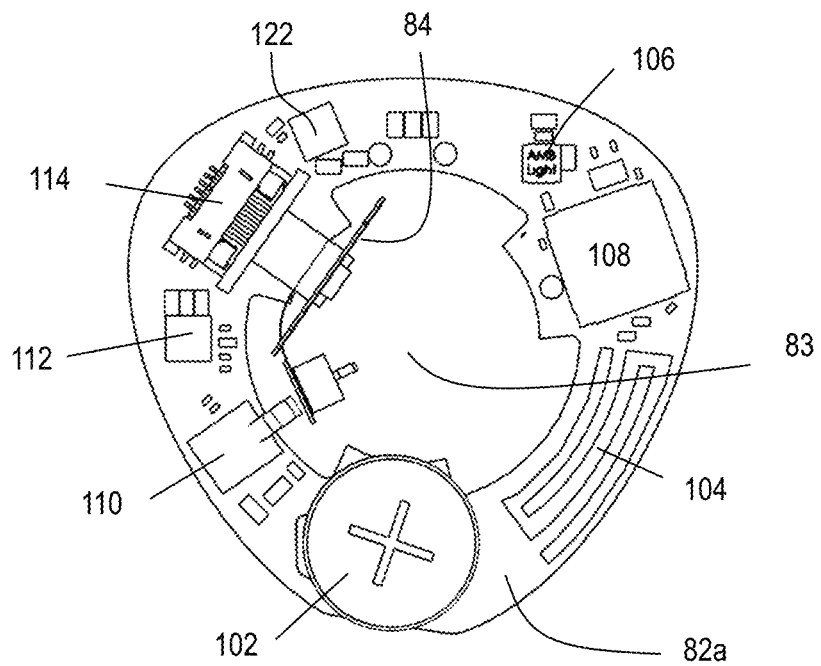
FIG. 10A is a top view of the main PCB and the secondary PCB of the first set of embodiments.
Figure 10B:
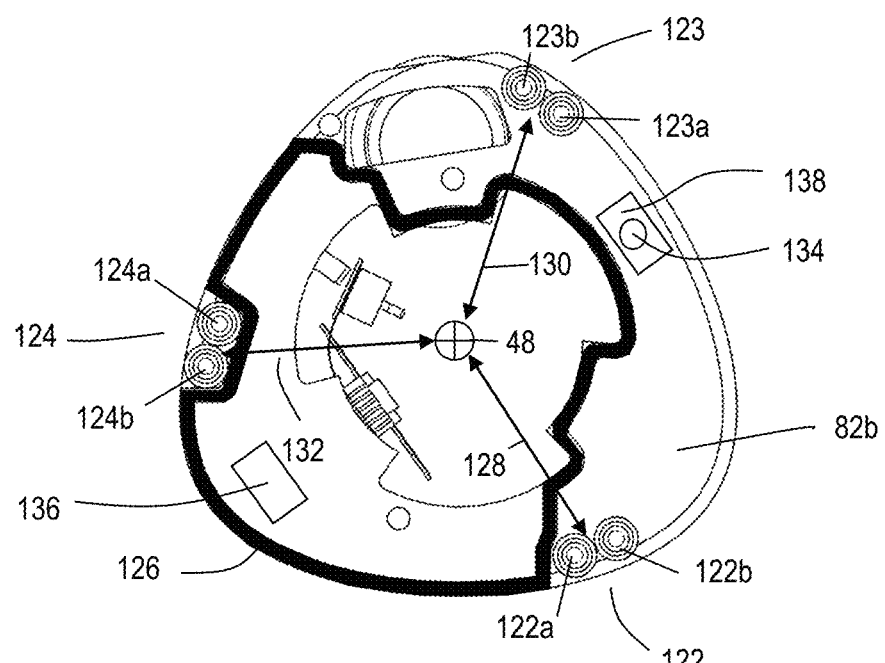
FIG. 10B is a bottom view of the main PCB and the secondary PCB of the first set of embodiments.

FIG. 9A shows a top perspective view of the main PCB(s) and the secondary PCB(s), while FIG. 9B shows a bottom perspective view of the same PCB(s), according to the first set of embodiments of device 20. FIGS. 10A and 10B show a top and bottom view of the same PCBs, respectively. Main PCB(s) 82 (shown in FIG. 8) may have a top surface 82a (shown in FIGS. 9A and 10A—top surface 82a is understood to be part of PCB(s) 82) that includes or supports a power source 102 which, in some embodiments, may comprise a battery such as a coin cell battery. Power source 102 provides electrical power to the electrical components integrated or coupled with injection device 20. The main PCB(s) 82 may also include a processing circuit 108. In some embodiments, processing circuit 108 may take the form of a System on Chip (SOC) integrated circuit that includes a processor, memory, and input/output ports. However, processing circuit 108 may also be implemented using other types of components, such as a microcontroller (MCU), or an Application Specific Integrated Circuit (ASIC). Processing circuit 108 may be configured to execute computer-executable instructions stored on non-transitory storage media. Main PCB(s) may also include a plurality of different types of sensors, such as a micro-switch sensor 110, a magnetometer 112, an accelerometer 140, an ambient light sensor 106, and/or one or more skin contact resistance sensors 122, 123, and 124. In embodiments that include secondary PCB(s), the secondary PCB(s) may include further sensors, such as another micro-switch sensor 116, a magnetometer 118, and an infra-red temperature sensor 120.

Micro-switch sensors 110 and 116 may be communicatively coupled with processing circuit 108. Each micro-switch sensor may include a physical switch coupled to an electrical circuit which outputs electrical signals to processing circuit 108 depending on the physical position or orientation of the physical switch. Micro-switch sensors 110 and 116 may be used to detect the positions of components of injection device 20. For example, micro-switch sensor 110 may be used to detect whether end cap 36 is attached to the proximal end of device housing 38. As discussed in more detail below, depending on the output of micro-switch sensor 110, processing circuit 108 may indicate to a user whether end cap 36 is attached to device 20. Similarly, micro-switch sensor 116 may be used to detect whether syringe assembly 22 is in one of two states, such as (i) the storage position or (ii) the injection position. Micro-switch sensor 116 may also be configured to detect whether syringe assembly 22 is in one of three states, such as (i) the storage position, (ii) the injection position, or (iii) the retracted position. Depending on the output of micro-switch sensor 116, processing circuit 108 may indicate to the user what position syringe assembly 22 is in.

Ambient light sensor 106 may be communicatively coupled with processing circuit 108 and may detect the amount or intensity of ambient light to which injection device 20 is exposed. Over-exposure to ambient light may render medication stored in barrel 30 ineffective or unsafe for injection. In some embodiments, processing circuit 108 may log the intensity and/or duration of ambient light detected by ambient light sensor 106. If the intensity and/or duration of exposure to ambient light exceeds pre-determined thresholds, the user may be informed that the medication should not be used.

Accelerometer 140 may be communicatively coupled with processing circuit 108 and may determine the orientation of injection device 20 (e.g., pointing up, down, or sideways). This may be important for certain types of drugs which may be significantly affected by gravity due to settling of particulates, etc., which would require that the drug be delivered in a particular orientation. The processing circuit 108 may also use the output of accelerometer 140 to warn the user if the device 20 is oriented improperly for injection (e.g., if the device is upside-down). As described in further detail below, accelerometer 140 may also be used to detect vibrations from an external device to aid in wirelessly pairing injection device 20 with the external device.

Many types of medication need to be stored at a first, relatively cool temperature (e.g., between 36 and 46 degrees Fahrenheit, or 2 and 8 degrees Celsius) to prevent spoliation, but then need to be warmed up to a second, warmer temperature (e.g., to room temperature, or between 65 and 75 degrees Fahrenheit, or 18 and 24 degrees Celsius) before being injected into the patient's body. To ensure that the medication within barrel 30 is stored at the appropriate storage temperature, and/or to ensure that the medication is warmed to the appropriate injection temperature, injection device 20 may be equipped with a mechanism for estimating the temperature of the medication. By ensuring that the medication has warmed up to the appropriate temperature, this information can be transmitted to a phone, or the device itself could signal a patient that the device is ready for use. In some embodiments, this temperature-measurement function may be performed by an infra-red (IR) temperature sensor 120 on secondary PCB 84. IR sensor 120 may be communicatively coupled with processing circuit 108. As best seen in FIG. 8, IR sensor 120 may be disposed adjacent to and facing towards barrel 30. IR sensor 120 may detect and measure electromagnetic radiation in the IR spectrum from barrel 30, and output an electrical signal based on the detected IR radiation. By sampling the electrical signal output by IR sensor 120, processing circuit 108 may estimate the temperature of medication within barrel 30.

Main PCB(s) may also be equipped with one or more antennas for sending or receiving wireless communications. For example, FIGS. 9A and 9B depict a Bluetooth Low Energy (BLE) antenna 104 disposed on an upper surface 82*a* of the main PCB(s), and a Near Field Communication (NFC) antenna 126 (shown as a thick black-lined element) disposed on a bottom surface 82*b* of the main PCB(s). Other embodiments in which main PCB(s) are equipped with only one antenna, or only one type of antenna, are also possible. As discussed in further detail below, these antenna(s) may allow injection device 20 to establish a wireless communication link with an external device.

Main PCB(s) may also be communicatively coupled or integrated with a plurality of sensors that detect contact with skin tissue. Skin contact sensors may be used to verify proper contact with the user's skin before the user activates injection device 20. Injection device 20 may also indicate to the user which sensors detect skin contact and which do not; this lets the user know which way he or she should tilt or move the injection device 20 before injection. This functionality decreases the likelihood of failed injections in which the needle 34 fails to penetrate the skin of the user, or penetrates at an improperly shallow angle.

FIGS. 9B and 10B depict an exemplary embodiment that includes three skin contact sensors 122, 123, and 124 disposed on the bottom surface 82*b* of the main PCB(s), and arranged in a symmetrical, tri-lobed shape. In this exemplary embodiment, each skin contact sensor 122, 123, and 124 includes two separate electrical terminals—sensor 122 includes terminals 122*a* and 122*b*, sensor 123 includes terminals 123*a* and 123*b*, and sensor 124 includes terminals 124*a* and 124*b*. Although only two electrical terminals are depicted for each sensor, other embodiments in which each sensor has more than two electrical terminals are also possible. Each skin contact sensor may measure electrical resistance between its electrical terminals, and output an electrical signal based on the measured resistance to processing circuit 108. The electrical resistance of skin tissue is generally lower than that of air, and so processing circuit 108 may determine that a particular skin contact sensor is in contact with skin tissue when the measured resistance is below a predetermined threshold.

Although FIGS. 9B and 10B depict each skin contact sensor 122, 123, and 124 as having two electrical terminals, other embodiments are possible in which each skin contact sensor has only one electrical terminal. In such cases, the electrical terminal of one skin contact sensor (e.g., sensor 122) may serve as a reference electrode that outputs a predetermined voltage. The electrical terminal on each of the other two skin contact sensors (e.g., sensors 123 and 124) may serve as a sensor electrode that measures electrical resistance of a conducting path between itself and the reference electrode. When the measured resistance between the reference electrode and a particular sensor electrode is below a predetermined threshold, processing circuit 108 may determine that both the reference electrode and the particular sensor electrode are in contact with human tissue, such as skin. When both sensor electrodes (e.g., on sensors 123 and 124) report measured resistances below a predetermined threshold, processing circuit 108 may determine that the reference electrode and both sensor electrodes are in contact with human tissue. Exemplary embodiments of device 20 that incorporate capacitance sensors are discussed below in relation to FIGS. 17A, 17B, 18A and 18B and the second set of embodiments of device 20.

As best shown in FIG. 10B, each skin contact sensor 122, 123, and 124 may be located a radial distance 128, 130, and 132 respectively outward from the longitudinal axis 48 (which, in the view shown in FIG. 10B, extends into the page). Sensors 122, 123, and 124 may optionally be arranged to symmetrically surround the opening 83, such that radial distances 128, 130, and 132 are equal to each other, and the angular separation between each sensor is also equal (e.g., in this case, 120°). Radial distances 128, 130, and 132 are greater than radial distance 41 of the user-graspable portion 37 (as shown in FIGS. 2 and 9), and may be greater than 10 mm in length. For example, in some embodiments, radial distances 128, 130, and 132 may each be between 10 mm-20 mm in length—in some cases, a distance of 15 mm to 20 mm may be appropriate. Although three skin sensors are depicted, other embodiments having only one or two skin sensors are also possible. Conversely, embodiments with more than three skin contact sensors are also possible—in such embodiments, the skin sensors may (but need not be) arranged to symmetrically surround opening 83. For example, other embodiments comprising four to twenty skin sensors are also contemplated.

While skin contact sensors 122, 123, and 124 have been described above as measuring electrical resistance, these skin contact sensors may alternatively be configured to detect skin contact by measuring electrical capacitance. Capacitance sensors may be configured to detect proximity of human tissue by detecting such tissue's effect on an electrical field created by the sensor (e.g., by detecting the effect of such tissue on the capacitance of a circuit being monitored or measured by the sensor). Capacitance sensors do not require a metallic, electrical terminal that directly contacts skin tissue, and so may be partially or completely sealed behind a protective, non-conducting cover (e.g., made of plastic). This may increase the durability of the capacitance sensor by decreasing seepage of moisture or foreign substances into sensitive electrical components. Capacitance sensors may also reduce the danger of electrostatic discharge damaging sensitive electrical components within the device, since capacitance sensors do not require exposed metallic contacts. Exemplary embodiments of device 20 that incorporate capacitance sensors are discussed below in relation to FIGS. 21A, 21B, 22A and 22B and the third set of embodiments of device 20.

Injection device 20 may also be equipped with a means for estimating the axial position or movement of piston 32 within barrel 30. This estimated axial position and/or movement may be used by processing circuit 108 to estimate the amount of medication remaining within barrel 30 and/or the amount of medication that has been dispensed, if any. In some embodiments, this may be accomplished by providing a magnet on or close to piston 32 as it slides along longitudinal axis 48, and one or more magnetometers that sense the magnetic field emitted by the magnet as it slides along the longitudinal axis. FIGS. 1-3 and 11 show an exemplary magnet 25 disposed on plunger 44 such that it maintains a fixed axial distance from piston 32 as the piston slides along longitudinal axis 48 within barrel 30. FIGS. 9A, 9B, 10A, and 10B also show exemplary placement of two magnetometers: magnetometer 112 on main PCB(s) 82, and magnetometer 118 on secondary PCB(s) 84. As shown, magnetometer 112 may be disposed radially farther from longitudinal axis 48 compared to magnetometer 118. Furthermore, magnetometer 118 may be disposed at an intermediate point along the length of barrel 30, instead of being positioned proximate to one end of barrel 30.

Figure 11:
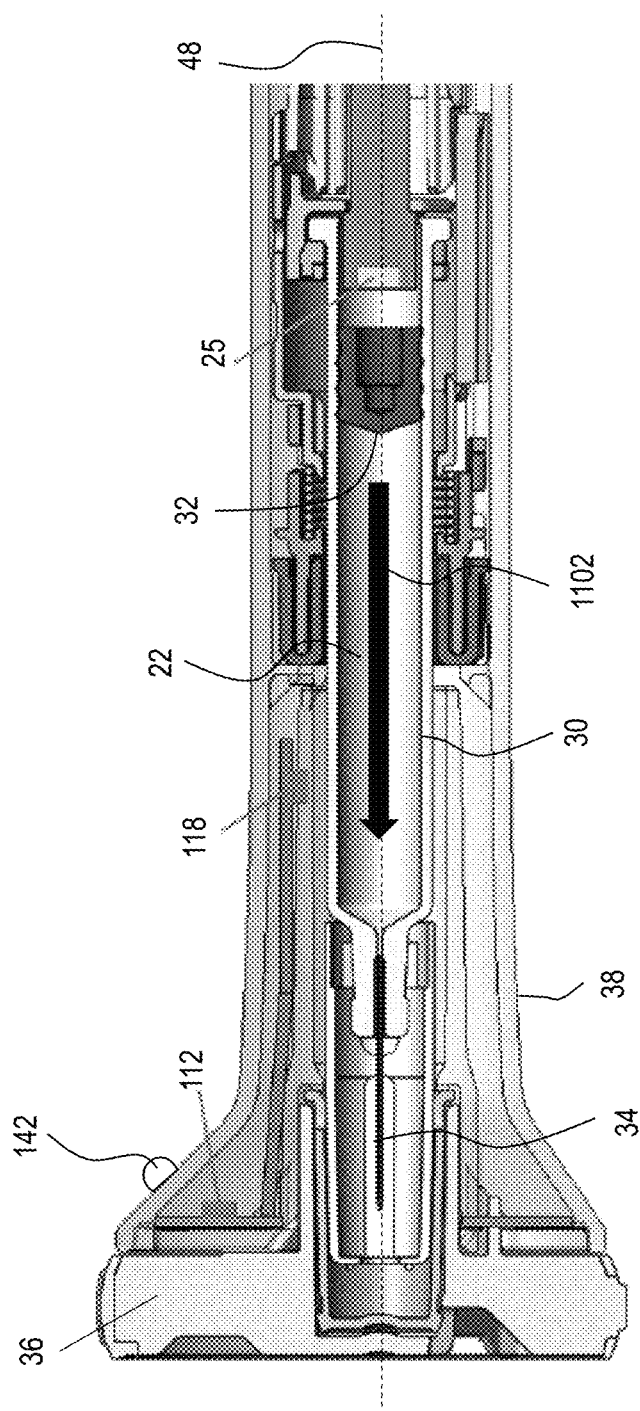
FIG. 11 is a cross sectional side view of an injection device, and shows a spatial relationship between a magnet and two magnetometers, according to the first set of embodiments.

FIG. 11 provides a side view of injection device 20 and shows the spatial relationship between magnet 25 and magnetometers 112 and 118, according to the first set of embodiments of device 20. In FIG. 11, injection device 20 is depicted with the syringe assembly 22 in the storage position, and end cap 36 secured to device housing 38 to cover proximal opening 40. Magnet 25 outputs a magnetic field that may be sensed by magnetometers 112 and 118 when magnet 25 is close enough to said magnetometers. Each magnetometer may output a signal based on the strength of the sensed magnetic field to processing circuit 108. The strength of the magnetic field sensed by magnetometers 112 and 118 changes based on the position of magnet 25 as it slides along longitudinal axis 48 in the direction of arrow 1102. For example, when syringe assembly 22 is in the storage position and piston 32 is in its initial piston position at the distal end of barrel 30 (as depicted in FIG. 11, as well as FIGS. 1 and 2), magnetometers 118 and 112 may detect only a very weak or non-existent magnetic field. When syringe assembly 22 is advanced to the injection position but piston 32 is still in its initial piston position, magnetometer 112 may continue to detect only a weak or no magnetic field, but magnetometer 118 may detect a stronger magnetic field than when syringe assembly is in the storage position. By sampling the strength of the magnetic field measured by magnetometers 112 and 118, processing circuit 108 may, in some embodiments, determine whether syringe assembly 22 is in the storage position or the injection position.

When syringe assembly 22 is in the injection position, and as piston 32 is advanced from its initial position in the direction of arrow 1102 towards its final piston position (shown in FIG. 3), magnetometer 118 detects a rising and then a decreasing magnetic field as magnet 25 approaches, passes, and then moves away from magnetometer 118. At the same time, advancing piston 32 in the direction of arrow 1102 causes magnetometer 112 to detect a rising magnetic field as magnet 25 moves closer to magnetometer 112. By sampling the strength of the magnetic field detected by both magnetometer 118 and 112, processing circuit 108 may estimate the position of magnet 25 along longitudinal axis 48. Based on this position estimate, processing circuit 108 may estimate the position of piston 32, as well as the amount of medication still remaining within barrel 30.

Figure 12:
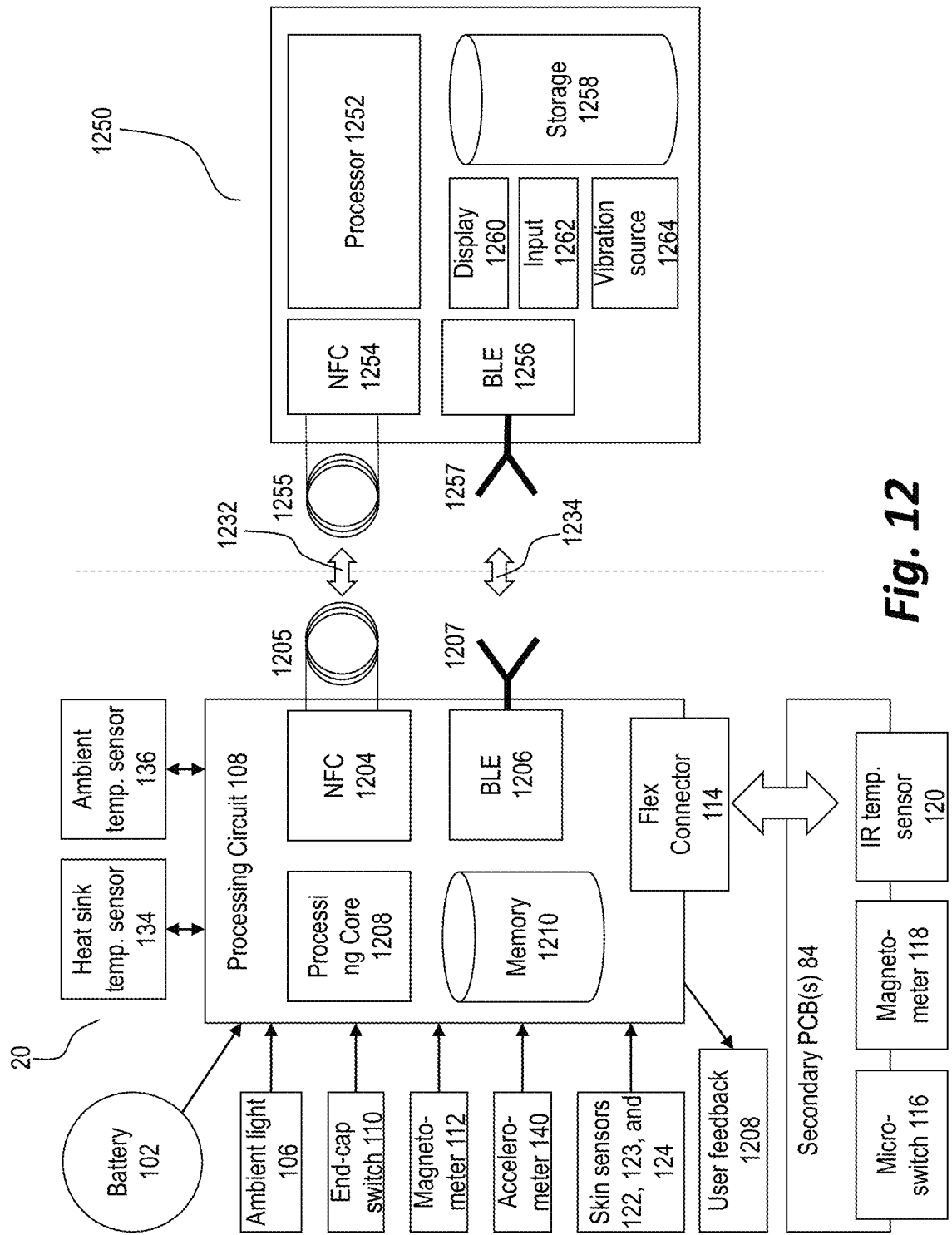
FIG. 12 is a system architecture view of electrical components within an injection device and of an external device, according to the first set of embodiments.

FIG. 12 provides a system architecture view of the electrical components within device 20, as well as a communication link with an exemplary external device 1250, according to the first set of embodiments of device 20. As discussed above, processing circuit 108 may be powered by a battery 102, and may comprise a processing core 1208 and a memory 1210 (e.g., internal flash memory, on-board electrically erasable and programmable read-only memory (EPROM), etc.). Memory 1210 may store instructions that, when executed by the processing core 1208, causes the processing circuit 1208 to perform the operations described herein. Processing circuit 108 may also be communicatively coupled with a plurality of sensors, such as an ambient light sensor 106, end-cap micro-switch 110, magnetometer 112, accelerometer 140, and skin-contact sensors 122, 123, and 124. Processing circuit 108 may also optionally be communicatively coupled to one or more secondary PCB(s) via a flex connector 114. The secondary PCB(s) may further incorporate a micro-switch 116, magnetometer 118, and an IR temperature sensor 120. Processing circuit 108 may also be connected to a means for user feedback 1208 that is integrated with device 20. The means for user feedback may include one or more indicator lights (e.g., implemented using light-emitting diodes (LEDs)), a display, a haptic indicator such as a vibration motor, and/or an auditory indicator such as a speaker). Processing circuit 108 may be communicatively coupled with each of the aforementioned components via one or more physical, electrical channels, such as (but not limited to) a General-Purpose Input/Output (GPIO) pin, an Inter-Integrated Circuit (I2C) bus, a Serial Peripheral Interface (SPI) connection, a Universal Asynchronous Receiver/Transmitter (UART) connection, and/or a Controller Area Network (CAN) bus. In some cases, signals received by the processing circuit 108 from some or all of the sensors may also be converted from an analog to a digital signal using an analog-to-digital converter (ADC).

Processing circuit 108 may also be configured to allow injection device 20 to communicate wirelessly with an external device (such as, for example, a mobile phone, a wearable device, a laptop, and/or server database). To facilitate wireless communication, processing circuit 108 may comprise a Near Field Communication (NFC) circuit 1204 communicatively coupled with a NFC antenna 1205, such as NFC antenna 126 depicted in FIGS. 9B and 10B. NFC circuit 1204 and NFC antenna 1205 allow processing circuit 108 to establish a wireless NFC communication link 1232 with an external device 1250. Alternatively, or in addition, processing circuit 108 may comprise a Bluetooth Low Energy (BLE) circuit 1206 communicatively coupled with a BLE antenna 1207, such as BLE antenna 104 depicted in FIGS. 9A and 10A. BLE circuit 1206 and BLE antenna 1207 allow processing circuit 108 to establish a wireless BLE communication link 1234 with external device 1250.

FIG. 12 also shows an exemplary external device 1250 that is physically separate from injection device 20. In this embodiment, exemplary external device 1250 may take the form of a mobile smartphone having a processor 1252 (e.g., a microprocessor or CPU) and storage 1258. Storage 1258 may comprise non-transitory computer-readable media storing computer-executable instructions that, when executed by processor 1252, causes device 1250 to perform the operations described herein. These computer-executable instructions may comprise a mobile application, such as a medical mobile application. Device 1250 may further comprise a display 1260 and a user input device 1262. User input device 1262 may comprise physical buttons or switches integrated with the smartphone. Although depicted separately in FIG. 12, all or a portion of user input device 1262 may be integrated with display 1260, e.g., in a touch-sensitive screen. Device 1250 may also comprise a vibration source 1264, such as a vibration motor.

Device 1250 may be configured to establish a wireless communication link with injection device 20. For example, external device 1250 may include a NFC circuit 1254 coupled with a NFC antenna 1255, which communicates with processing circuit 108 via communication link 1232. Device 1250 may also comprise a BLE circuit 1256 coupled with a BLE antenna 1207, which communicates with processing circuit 108 via communication link 1234.

Figure 13:
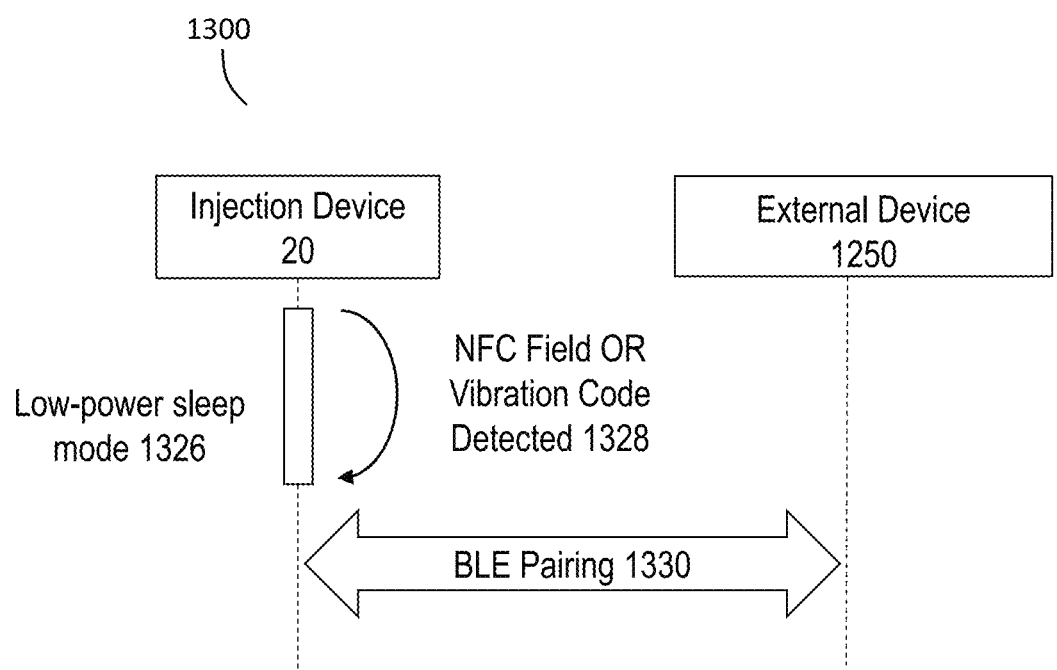
FIG. 13 is a flow diagram showing a process for "pairing" or establishing a communication session between an injection device and an external device, according to any of the first set of embodiments, as well as any of a second, and a third set of embodiments.

FIG. 13 is a flow diagram showing an exemplary process 1300 for "pairing" or establishing a communication session between injection device 20 and external device 1250. Process 1300 may be used by any of the first set of embodiments of device 20, as well as any of the second and the third set of embodiments of device 20 described below. To conserve power, injection device 20 may initially be stored in a low-power sleep mode 1326. While in this sleep mode 1326, some or all of the components coupled to or integrated with processing circuit 108 may be shut down or put in a low-power state to conserve power. For instance, some or all of the sensors coupled with processing circuit 108 may be powered down, the BLE circuit 1206 and BLE antenna 1207 may be powered down, and part or all of the processing core 1208 may be powered down or operated at a slower clock speed. If the device 20 is in a low-power sleep mode 1326, the device may need to be "woken up" before it can be paired with external device 1250.

One way to wake up injection device 20 is to configure external device 1250 to emit a NFC field (e.g., an electromagnetic field) using its NFC circuit 1254 and NFC antenna 1255 (step 1328). When external device 1250 is placed in close proximity with injection device 20 (e.g., within a few centimeters), the emitted NFC field induces an electric current to flow within NFC antenna 1205 coupled with processing circuit 108. Processing circuit 108, in turn, may be configured to wake up injection device 20 from its low-power sleep mode when processing circuit 108 detects this induced electric current. Processing circuit 108 may also be configured to wake up device 20 only when it detects an induced electric current that conforms to an expected code or pattern, so as to prevent spurious background electromagnetic radiation from waking up injection device 20.

Another way to wake up injection device 20 is to configure device 20 to wake up when it detects a specific vibration pattern (also step 1328). For example, to wake up device 20, a user may position device 20 so that it contacts external device 1250—for instance, device 20 may be placed on top of external device 1250. External device 1250 may then be instructed by a user to vibrate according to a specific, pre-determined pattern, using vibration source 1264. The vibrations from external device 1250 may be detected by accelerometer 120 in injection device 20. When the detected vibrations match an expected pattern, processing circuit 108 may be configured to wake up injection device 20 from its low-power sleep mode.

When injection device 20 first wakes from its low-power sleep mode, processing circuit 108 may engage in a BLE pairing process 1330 with external device 1250. BLE pairing process 1330 may be similar or the same as the BLE pairing process defined in the Bluetooth Core Specification v5.0 published by Bluetooth SIG on Dec. 6, 2016, the entire contents of which are incorporated herein by reference. BLE pairing process 1330 may begin with injection device 20 broadcasting one or more BLE advertisement packets using its BLE circuit 1206 and BLE antenna 1207. When external device 1250 receives the broadcasted BLE advertisement packets via BLE circuit 1256 and BLE antenna 1257, it can respond with a wireless BLE transmission that begins a communication flow between injection device 20 and external device 1250. The end result of this communication flow is an established BLE communication session between injection device 20 and external device 1250 through which the two devices may exchange data.

Figure 14A:
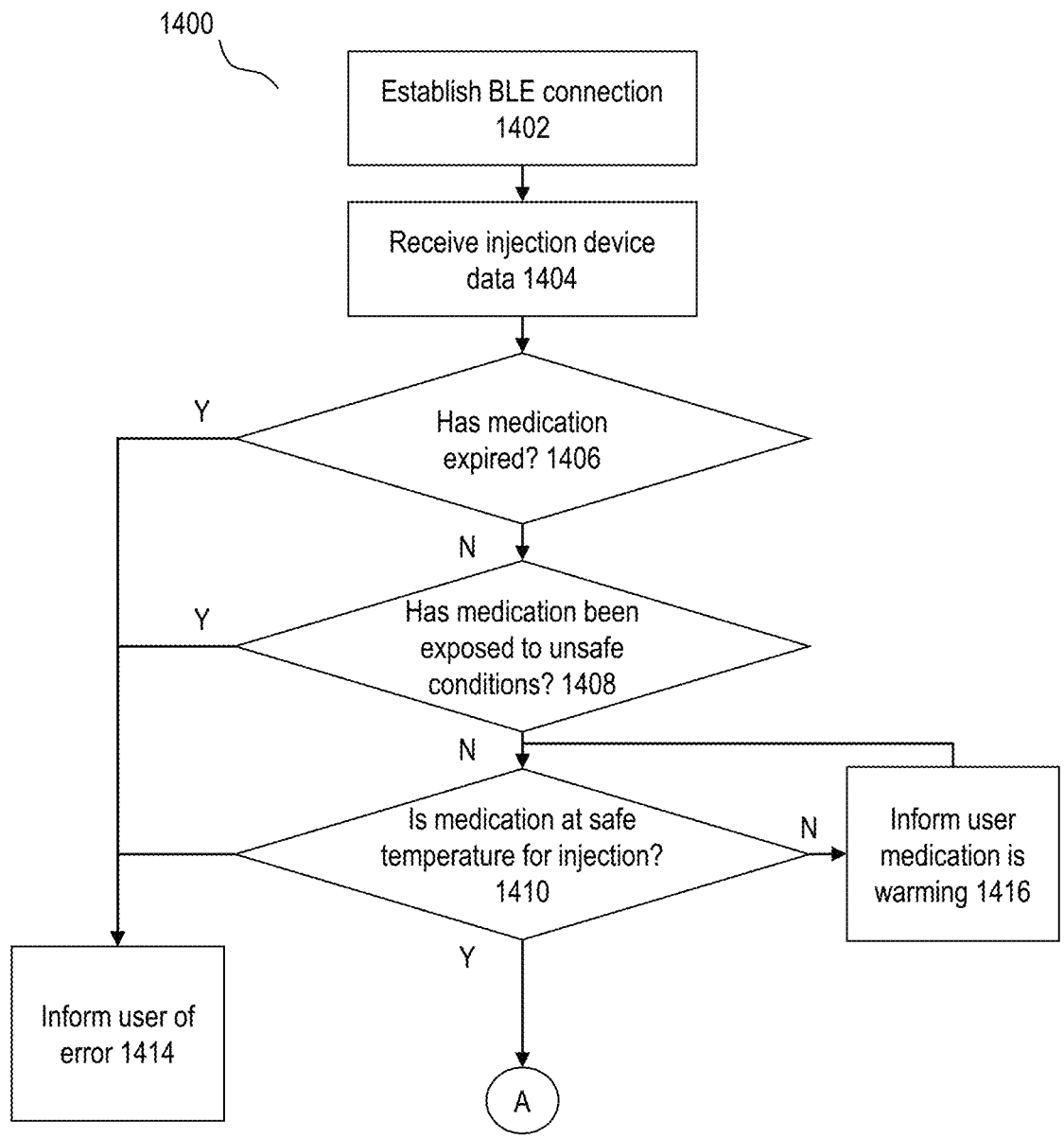
FIGS. 14A and 14B depict a flow-chart showing a process implemented by a mobile medical application running on an external device, according to any of the first, the second, and the third set of embodiments.
Figure 14B:
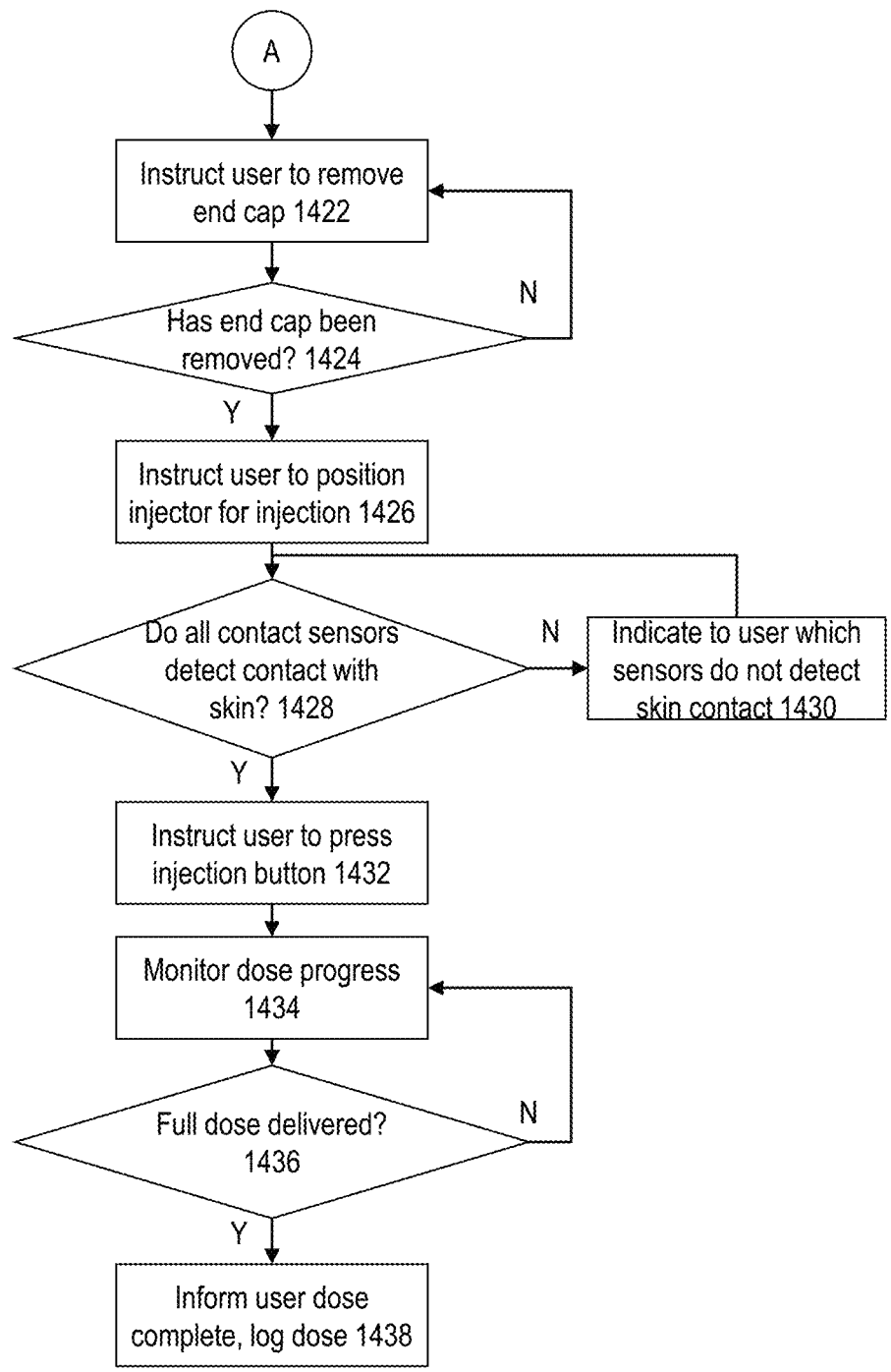

FIGS. 14A and 14B is a flow-chart showing an exemplary process 1400 implemented by a mobile medical application running on external device 1250. Process 1400 may be used in conjunction with any of the first set of embodiments of device 20, as well as with any of the second and third set of embodiments of device 20 described below. Process 1400 begins when a BLE connection is established between injection device 20 and external device 1250 (step 1402). At step 1404, external device 1250 receives data from injection device 20 through the established BLE connection. The data received from injection device 20 may comprise data or measurements from some or all of the above-described sensors in injection device 20, or information derived from or based on such data or measurements. The data received from injection device 20 may also comprise data stored in the memory of device 20, or information derived from such data—such data may include the type of medication stored in injection device 20, the medication's expiration date, the identity of a prescribing physician, the place or date of the medication's manufacture, the model of the injection device, and the like.

At step 1406, process 1400 determines whether the medication has expired. This can be done by comparing the medication's expiration date received in step 1404 against the current date. If the medication has expired, process 1400 branches to step 1414, in which external device 1250 informs the user that the medication has expired, such as through a message on device 1250's display or through an audible message. If the medication has not expired, process 1400 branches to step 1408.

At step 1408, process 1400 determines whether the medication has been exposed to unsafe conditions. This step may comprise checking data saved in or derived from a log of ambient light exposure stored by processing circuit 108. If the intensity and/or duration of exposure to ambient light exceeds pre-determined thresholds, process 1400 may branch to step 1414 and inform the user that the medication should not be used. The logic for comparing data from the log of ambient light exposure to pre-determined limits on intensity and/or duration of exposure may be performed by either processing circuit 108 of injection device 20, by processor 1252 of external device 1250, or a combination of both. Alternatively, or in addition, step 1408 may comprise determining whether the medication has been exposed to unsafe temperatures during storage or transit. This may be accomplished by checking data saved in or derived from a log of the medication's temperature stored by processing circuit 108. If the medication has been exposed to temperatures outside of an ideal storage range (e.g., between 36 and 46 degrees Fahrenheit), or if the medication has been exposed to temperatures outside of the ideal storage range for an impermissibly long length of time, process 1400 may also branch to step 1414 and inform the user that the medication should not be used. The logic for comparing temperature log data with pre-determined limits on temperature may also be performed by processing circuit 108 of injection device 20, by processor 1252 of external device 1250, or a combination of both.

At step 1410, process 1400 determines whether the medication is at a safe temperature for injection. Although the medication in injection device 20 may need to be stored at a cooler temperature (e.g., between 36 and 46 degrees Fahrenheit) to prevent spoliation, the medication may need to be warmed up to a warmer temperature (e.g., approximately room temperature, or between 65 and 75 degrees Fahrenheit) before it is injected. At step 1410, process 1400 determines whether the medication has warmed to the target injection temperature. If not, process 1400 branches to step 1416, at which process 1400 informs the user that the medication is still warming, then branches back to step 1410. If so, process 1400 branches to step 1422 (shown in FIG. 14B).

Referring now to FIG. 14B, at step 1422, process 1400 may instruct the user to remove the end cap 36. At step 1424, process 1400 determines whether the end cap 36 has been removed. As discussed above, processing circuit 108 may determine whether end cap 36 has been removed or not using end-cap micro-switch sensor 110, and may inform external device 1205 via the BLE communication link 1234. If the end cap has not been removed, process 1400 branches back to step 1422. If the end cap has been removed, process 1400 branches to step 1426.

At step 1426, process 1400 may instruct the user to position the injection device 20 for injection. This may comprise instructing the user to place proximal opening 40 of device 20 flush against a portion of the user's body, such as the user's abdomen or one of the user's thighs. At step 1428, process 1400 determines whether all skin contact sensors (e.g., sensors 122, 123, and 124) detect contact with skin tissue. If less than all of the skin contact sensors detect contact with skin tissue, process 1400 branches to step 1430. If all of the skin contact sensors detect contact with skin tissue, process 1400 branches to step 1432.

Figure 15:
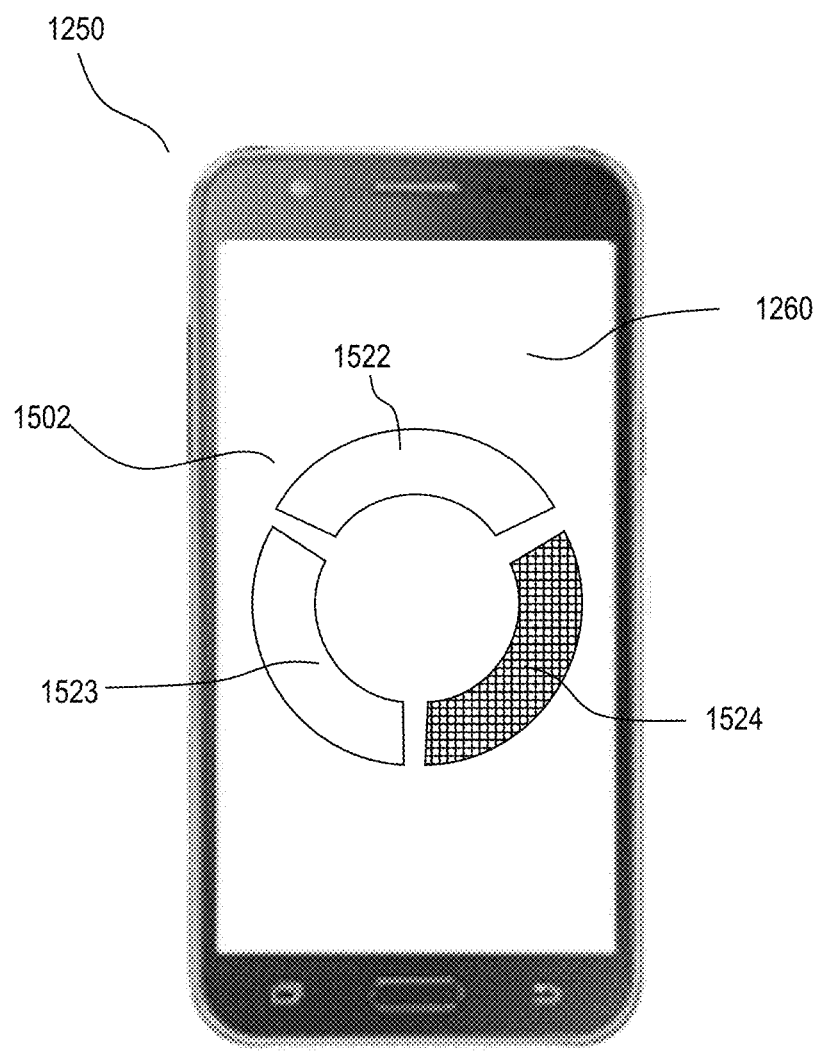
FIG. 15 is a view of a schematic for displaying status of skin contact sensors on a display of an external device.

At step 1430, process 1400 may indicate to the user which individual sensors of the plurality of skin contact sensors (e.g., sensors 122, 123, and 124) detect contact with skin tissue, and which individual sensors do not detect contact with skin tissue. As illustrated in FIG. 15, this may be done by displaying a schematic 1502 on the display 1260 of external device 1250. Schematic 1502 may include three separate indicators 1522, 1523, and 1524, which correspond to skin contact sensors 122, 123, and 124 respectively. As shown, the indicators 1522, 1523, and 1524 may be arranged to mimic the physical arrangement of skin contact sensors 122, 123, and 124, e.g., the indicators may be symmetrically arranged around a central aperture. In embodiments where there are less or more than three skin contact sensors, schematic 1502 may also include a corresponding number of indicators. When a skin contact sensor does not detect contact with skin tissue, the schematic 1502 may alter the appearance of that skin sensor's corresponding indicator. In the example shown in FIG. 15, skin contact sensors 122 and 123 detect skin contact but skin contact sensor 124 does not detect contact with skin tissue. Accordingly, the indicator 1524 corresponding to skin contact sensor 124 has been filled in with a color, texture, or visual pattern that is different than the color, texture, or visual pattern for indicators 1522 and 1523 corresponding to skin contact sensors 122 and 123 (as shown by the cross-hatching for indicator 1524). Other ways of indicating the presence or absence of skin contact are also possible—for instance, the shape of an indicator may change, or an icon or symbol may appear or disappear depending on whether a particular skin contact sensor detects any contact with skin tissue.

Alternatively, or in addition, device 20 may be equipped with visual indicators (e.g., light-emitting diodes (LEDs)) that indicate to the user which skin contact sensors detect skin contact and which do not. For example, device 20 may be provided with a plurality of LEDs on the top surface of main PCB(s) 82a, wherein each LED corresponds to one of the skin contact sensors. The physical arrangement of the LEDs may correspond to the arrangement of the skin contact sensors to make clear to the user which LED corresponds to which skin contact sensor—for example, each LED may be disposed on top of the skin contact sensor to which it corresponds. One such exemplary LED has been depicted as LED 142 in FIG. 11. Depending on whether a sensor detects contact with skin tissue, its corresponding LED may light up, turn off, and/or change color. This provides another intuitive way for the user to quickly determine which skin contact sensors are not detecting contact with skin tissue, and which way the user should tilt or move device 20 to achieve better skin contact.

Figure 17A:
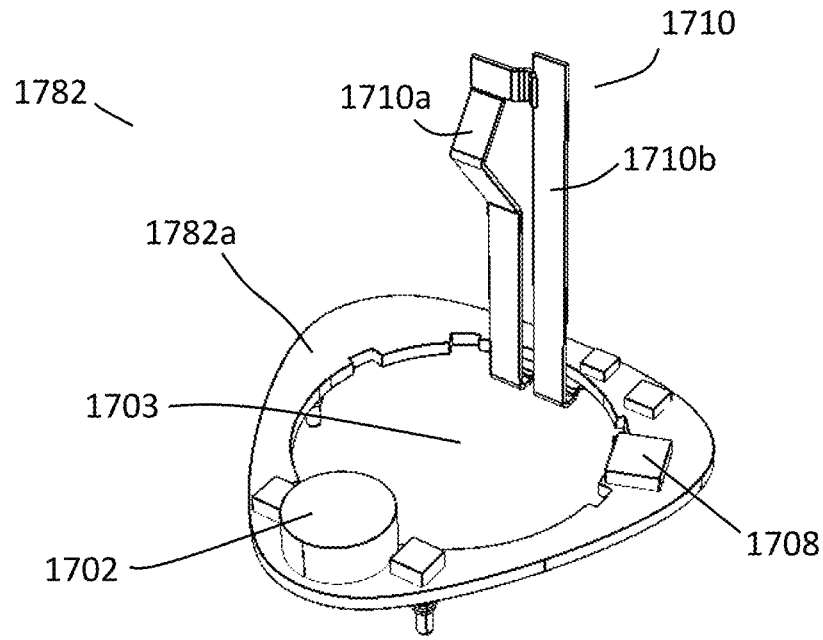
FIG. 17A is a top perspective view of a main PCB and a syringe position detector switch, according to the second set of embodiments.
Figure 17B:
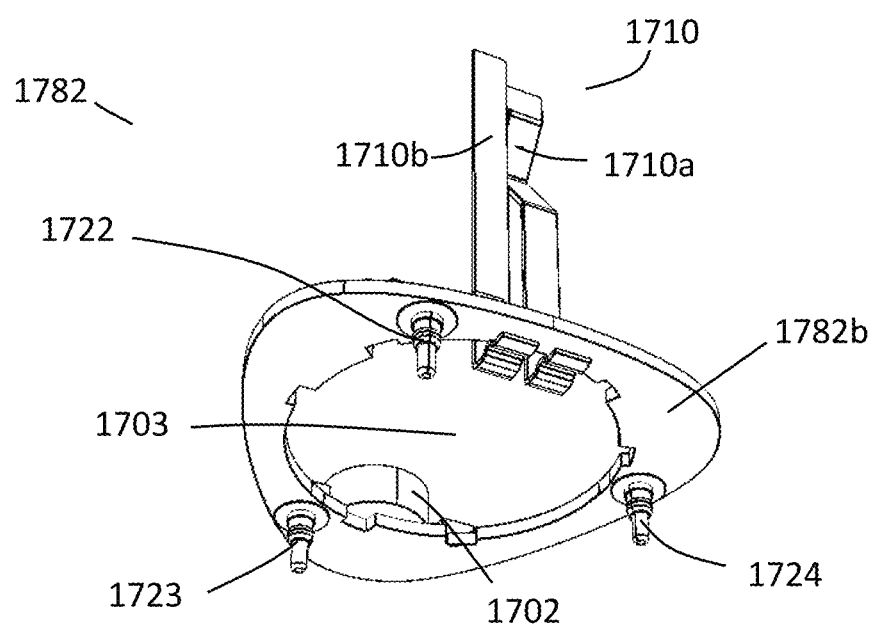
FIG. 17B is a bottom perspective view of the main PCB and the syringe position detector switch, according to the second set of embodiments.
Figure 18A:
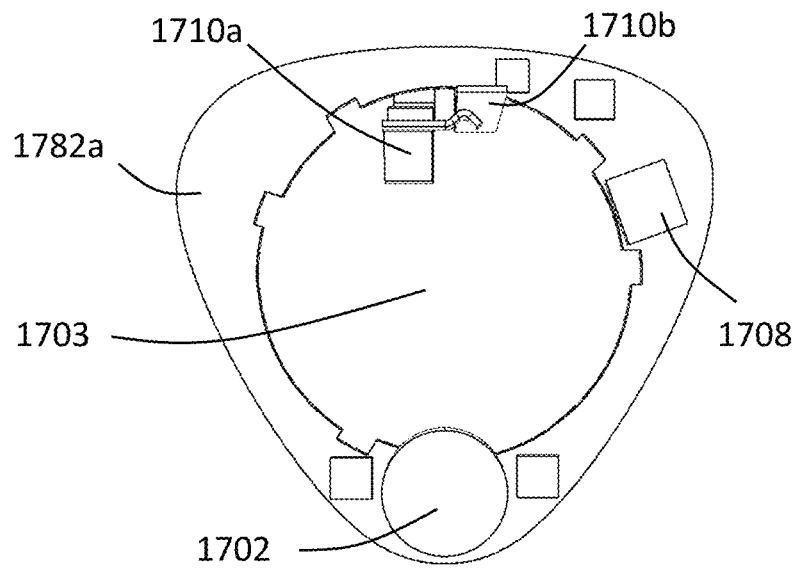
FIG. 18A is a top view of the main PCB and the syringe position detector switch, according to the second set of embodiments.
Figure 18B:
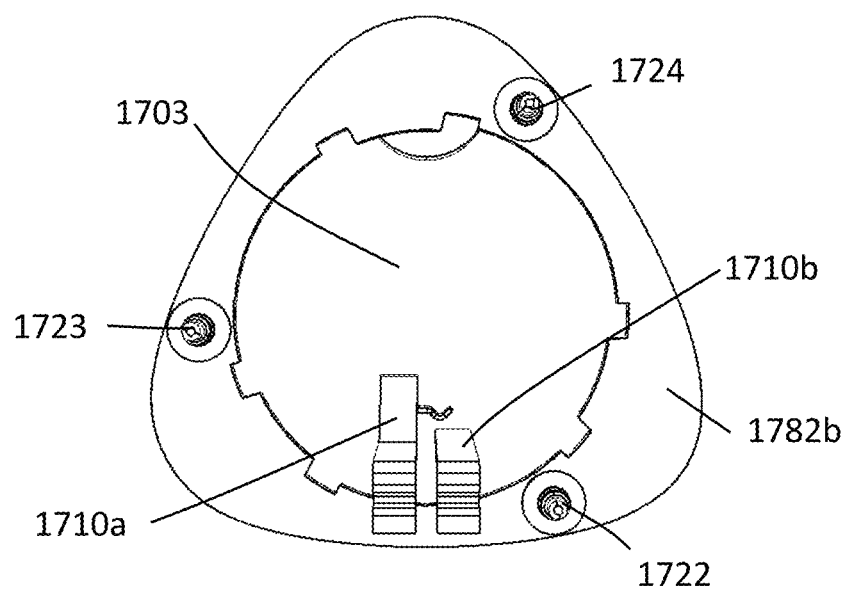
FIG. 18B is a bottom view of the main PCB and the syringe position detector switch, according to the second set of embodiments.

FIG. 17A shows a top perspective view of a main PCB 1782, while FIG. 17B shows a bottom perspective view of the same PCB 1782, according to a second set of embodiments of device 20. FIGS. 18A and 18B show a top and bottom view of the same PCB, respectively. Similar to the previously-described main PCB 82 in the first set of embodiments, main PCB 1782 may also be positioned in the end portion 39 of housing 38 of device 20, as illustrated in FIG. 8. Also similar to the previously-described main PCB 82, main PCB 1782 defines an opening 1703 (analogous to opening 83 in PCB 82) through which injection needle 34 of syringe assembly 22 is configured to pass. Main PCB 1782 comprises a top surface 1782a and a bottom surface 1782b (top surface 1782a and bottom surface 1782b are understood to be part of PCB 1782). Top surface 1782a includes or supports a power source 1702 which, in some embodiments, may comprise a battery such as a coin cell battery. Power source 1702 provides electrical power to the electrical components integrated or coupled with injection device 20. Main PCB 1782 may also include a processing circuit 1708, which may be configured similarly to previously-described processing circuit 108.

Main PCB 1782 in the second set of embodiments may differ from main PCB 82 in the first set of embodiments in several respects. As best seen in a comparison of FIGS. 9A and 17A, instead of a secondary PCB 84, main PCB 1782 mounts a syringe position detector switch 1710 that allows processing circuit 1708 to determine whether the syringe assembly 22 is in the storage position, injection position, or retracted position. Syringe position detector switch 1710 comprises two proximally extending arms 1710a, 1710b. In one example, arm 1710a is an angled arm 1710a and arm 1710b is disposed adjacent to arm 1710a. In one example, each of arm 1710a and arm 1710b includes a distal end coupled to the PCB 1782 (in the illustrative example, the distal end including a foot configuration for mounting to PCB), and arms may extend proximally in a parallel relationship. Angled arm 1710a comprises an angled radial portion that protrudes inwards towards longitudinal axis 48 for contact with the movable syringe barrel to cause deflection of the arm 1710a and a laterally extending portion that overlaps a contact portion of the arm 1710b for selective electrical contact with the arm 1710b. Both arms may be made be made of metal, or any other relatively flexible, conductive material, and may be electrically connected to processing circuit 1708. When contact portion of arm 1710a contacts arm 1710b, the contact completes an electrical circuit between angled arm 1710a and 1710b. When angled arm 1710a is not in contact with straight arm 1710b, the electrical circuit between the two arms is broken. By continuously or periodically monitoring whether the two arms 1710a and 1710b are in contact, processing circuit 1708 can determine whether syringe assembly is in the storage position, the injection position, or the retracted position.

Figure 19:
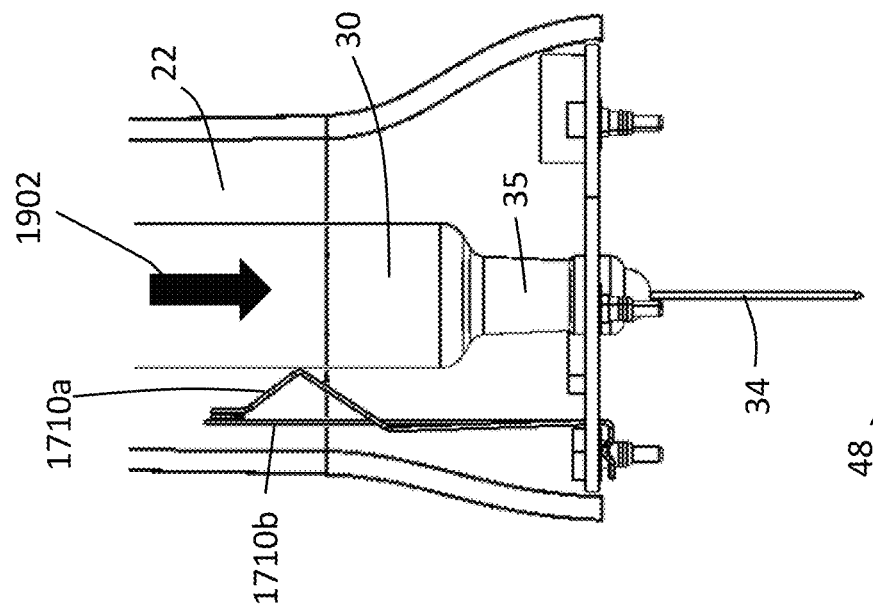
FIG. 19 is a side view of the injection device when the syringe assembly is in the storage position or the retracted position, according to the second set of embodiments.
Figure 20:
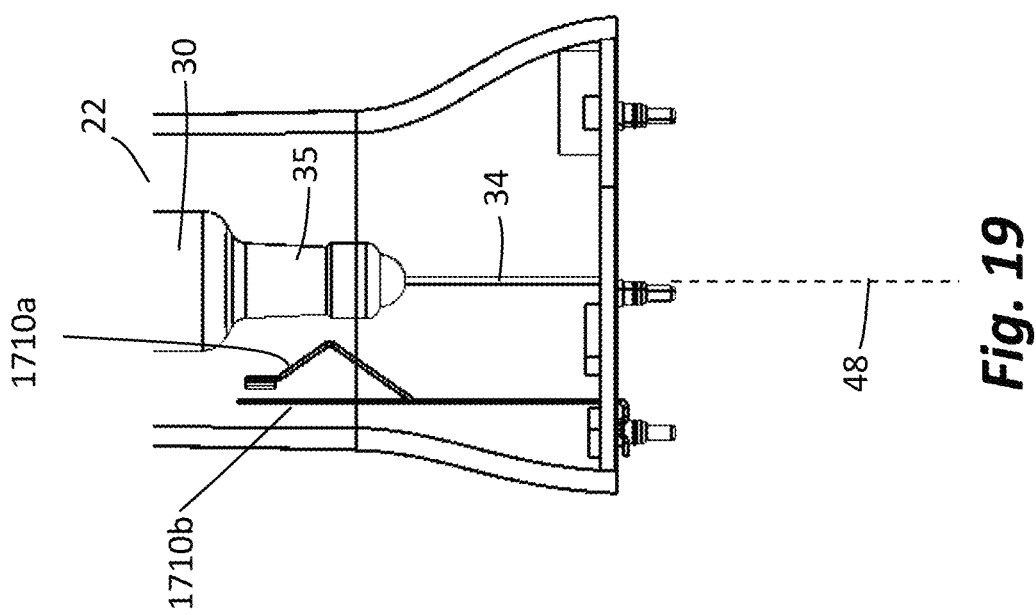
FIG. 20 is a side view of the injection device when the syringe assembly in the injection position, according to the second set of embodiments.

FIG. 19 shows a side-view of device 20 when syringe assembly 22 is in the storage position or the retracted position. As shown, when the syringe assembly 22 is in one or both of these positions, the angled arm 1710a and straight arm 1710b are positioned slightly apart and do not contact each other. FIG. 20 shows a side-view of device 20 when syringe assembly 22 is in the injection position. When the syringe assembly 22 moves into the injection position, the barrel 30 of syringe assembly 22 translates downwards, in the distal direction, as represented by arrow 1902. Since the barrel 30 has a wider diameter than needle 34 or needle hub 35, the downward translation of barrel 30 causes barrel 30 to contact the angled portion of angled arm 1710a, and to push angled arm 1710a radially away from longitudinal axis 48 such that it contacts straight arm 1710b. This completes an electrical circuit between angled arm 1710a and straight arm 1710b. Thus, when the processing circuit 1708 detects an open circuit between arms 1710a and 1710b, it may determine that syringe assembly 22 is in either the storage position or the retracted position. When the processing circuit 1708 detects a closed circuit between arms 1710a and 1710b, it may determine that syringe assembly is in the injection position.

Main PCB 1782 may also differ from main PCB 82 in its configuration of skin contact sensors. As best seen in a comparison of FIGS. 9B and 17B, instead of using three skin contact sensors that each comprise two electrodes (e.g., in the first set of embodiments, sensor 122 comprises electrodes 122a and 122b, sensor 123 comprises electrodes 123a and 123b, and sensor 124 comprises electrodes 124a and 124b), the bottom surface 1782b of main PCB 1782 in the second set of embodiments comprises only three single electrodes 1722, 1723, and 1724 pointing distally from the distal surface of PCB. These electrodes may be disposed radially equally from longitudinal axis 48, and may also be positioned equi-circumferentially from each other. One of these three electrodes, e.g., electrode 1722, may be connected to a voltage supply that provides a reference voltage V. The other two electrodes may each be connected with separate voltage sensors. The output of both voltage sensors may be connected to processing circuit 1708. If the voltage sensor connected to electrode 1723 senses a positive voltage above a reference threshold, the processing circuit 1708 may determine that both electrodes 1722 and 1723 are in contact with skin tissue. If the voltage sensor connected to electrode 1724 senses a positive voltage above the threshold, the processing circuit 1708 may determine that both electrodes 1722 and 1724 are in contact with skin tissue. If the voltage sensors connected to both electrodes 1722 and 1723 detect a voltage above the threshold, processing circuit 1708 may determine that all three electrodes 1722, 1723, and 1724 are in contact with skin tissue. Relative to the main PCB 82 in the first set of embodiments, this arrangement of electrodes 1722, 1723, and 1724 decreases the number of needed electrodes, thus reducing complexity and costs in manufacturing and assembly.

Although the foregoing description of the second set of embodiments of device 20 describes differences between this second set of embodiments and the previously-described first set of embodiments, it should be understood that the second set of embodiments may also include features present in the first set of embodiments, as well as other features. For example, certain embodiments in this second set of embodiments may include the secondary PCB 84 of the first set of embodiments, either in place of or in addition to the proximally extending arms 1710a, 1710b. This secondary PCB 84 in the second set of embodiments may include one, some, or all of the sensors previously-described as being mounted on secondary PCB 84 in the first set of embodiments. The second set of embodiments of device 20 may also use different configurations of skin contact sensors, including configurations identical or similar to the configurations described with respect to the first set of embodiments. As an example, main PCB 1782 in the second set of embodiments may, in some embodiments, comprise pairs of electrodes similar to those described in the first set of embodiments (e.g., electrodes 122a and 122b, 123a and 123b, etc., as shown in FIG. 9B). Main PCB 1782 may comprise one, two, three, or more sets of such pairs of electrodes.

Figure 21A:
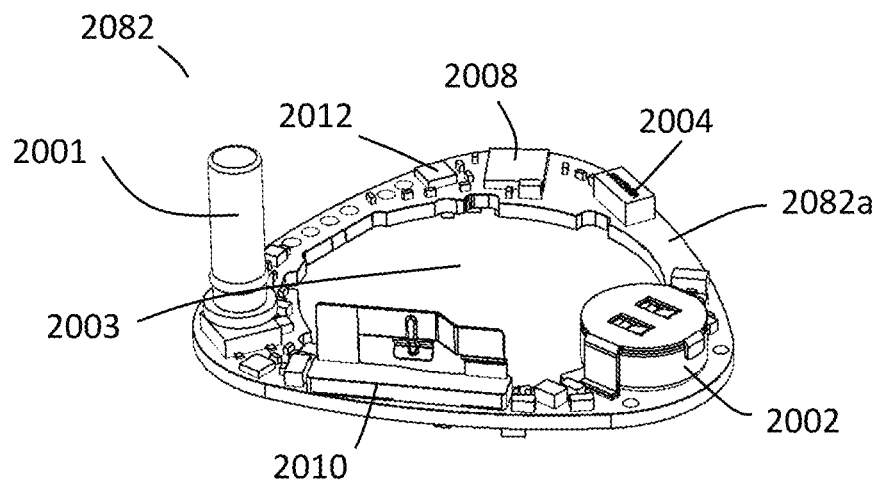
FIG. 21A is a top perspective view of a main PCB, according to the third set of embodiments.
Figure 21B:
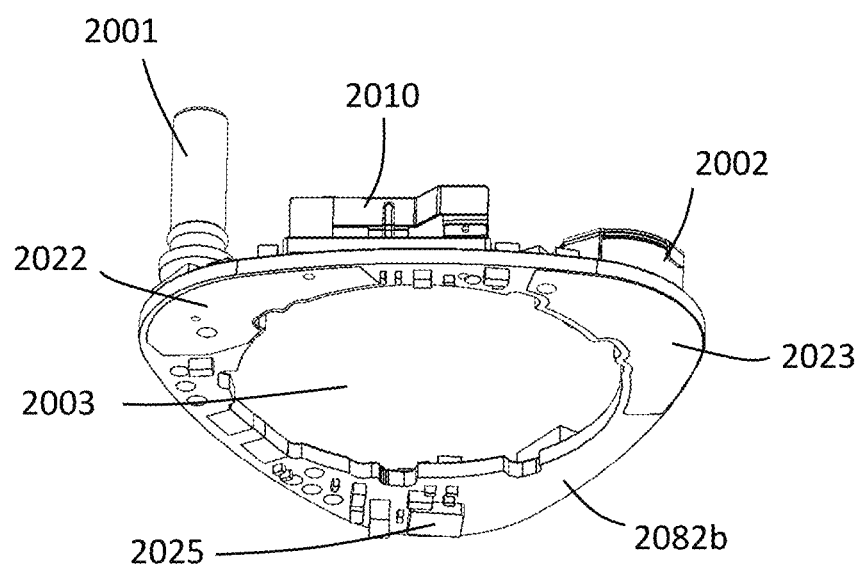
FIG. 21B is a bottom perspective view of the main PCB, according to the third set of embodiments.
Figure 22A:
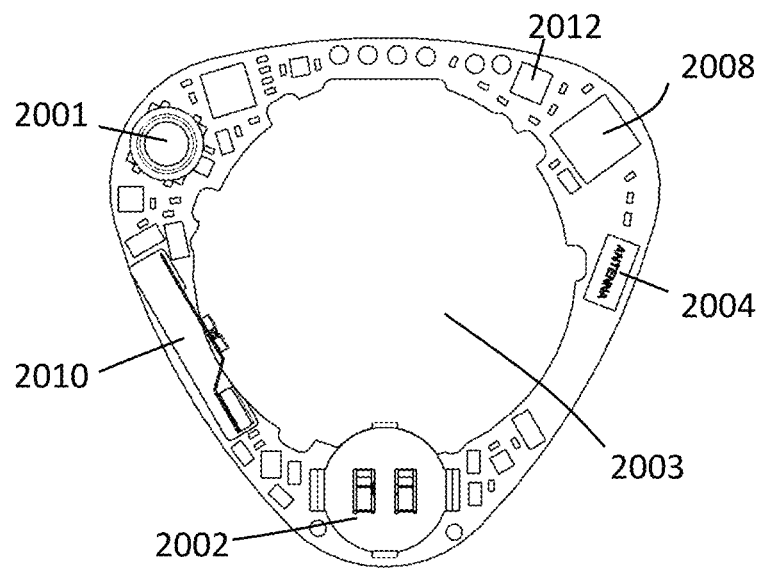
FIG. 22A is a top view of the main PCB, according to the third set of embodiments.
Figure 22B:
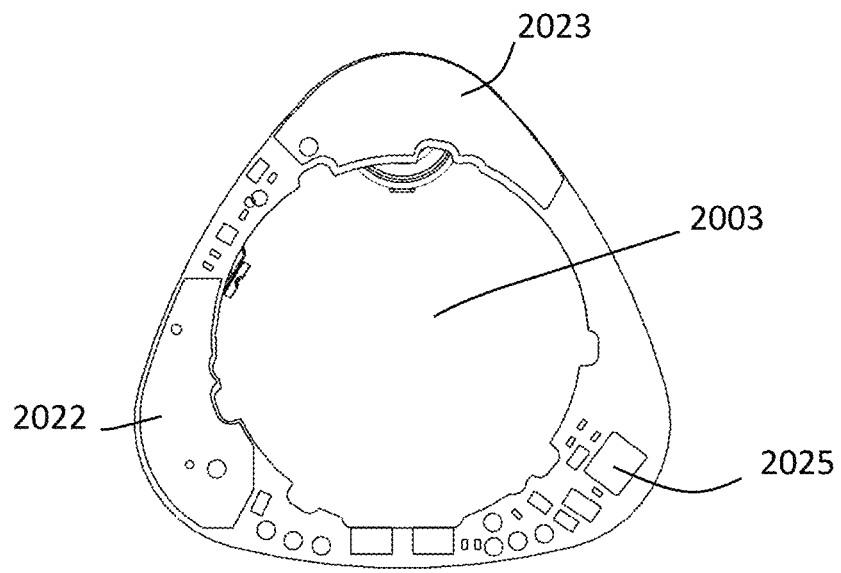
FIG. 22B is a bottom view of the main PCB, according to the third set of embodiments.

FIG. 21A shows a top perspective view of a main PCB 2082, while FIG. 21B shows a bottom perspective view of the same PCB 2082, according to a third set of embodiments. FIGS. 22A and 22B show a top and bottom view of the same PCB, respectively. Similar to the previously-described main PCB 82 in the first set of embodiments, main PCB 2082 may also be positioned in the end portion 39, as illustrated in FIG. 8. Also similar to the previously-described main PCB 82 in the first set of embodiments, main PCB 2082 defines an opening 2003 (analogous to opening 83 in PCB 82) through which injection needle 34 of syringe assembly 22 is configured to pass. Main PCB 2082 comprises a top surface 2082*a* and a bottom surface 2082*b* (top surface 2082*a* and bottom surface 2082*b* are understood to be part of PCB 2082). Top surface 2082 includes or supports a power source 2002 which, in some embodiments, may comprise a battery such as a coin cell battery. Power source 2002 provides electrical power to the electrical components integrated or coupled with injection device 20. A battery door (not shown) in housing 38 may hinge or swing open to allow access to power source 2002. Main PCB 2082 may also include a processing circuit 2008, which may be configured similarly to previously-described processing circuit 108.

Main PCB 2082 may optionally differ from main PCB 82 (in the first set of embodiments) and main PCB 1782 (in the second set of embodiments) in several respects.

First, main PCB 2082 may not include either a secondary PCB 84 or a syringe position detector switch 1710. The position of the syringe assembly 22 may be detected using other methods (e.g., using an accelerometer), rendering secondary PCB 84 and/or syringe position detector switch 1710 unnecessary. Removing secondary PCB 84 and/or syringe position detector switch 1710 may decrease complexity and/or costs in manufacturing and assembly.

Second, main PCB 2082 may mount or support a temperature check button 2001. This temperature check button 2001 may protrude from a port or cutout (not shown) on housing 38 of device 20. As discussed in further detail below, this button 2001 may be a physical button that, when actuated by a user, sends an electrical and/or digital signal that causes processing circuit 2008 to power on, to check the temperature of the device 20, and to indicate to the user whether the device 20 is at the correct temperature for administering the drug.

Third, instead of using NFC or BLE trace antennas arranged on the top and/or bottom surface of the PCB, NFC or BLE connectivity may be provided by one or more chip antennas 2004 mounted on the PCB 2082. Such chip antennas 2004 may receive signals from processing circuit 2008 that cause the antennas to send wireless communications to external devices. Although FIG. 21A depicts only one chip antenna 2004, some embodiments in the third set of embodiments may comprise two or more chip antennas, e.g., one BLE chip antenna and a separate NFC chip antenna. In some embodiments, processing circuit 2008 may itself comprise an integrated BLE antenna, while chip antenna 2004 may comprise a NFC antenna. Some embodiments in the third set of embodiments may also use PCB trace antennas (similar to those discussed above for the first set of embodiments) instead of chip antennas.

Figure 23A:
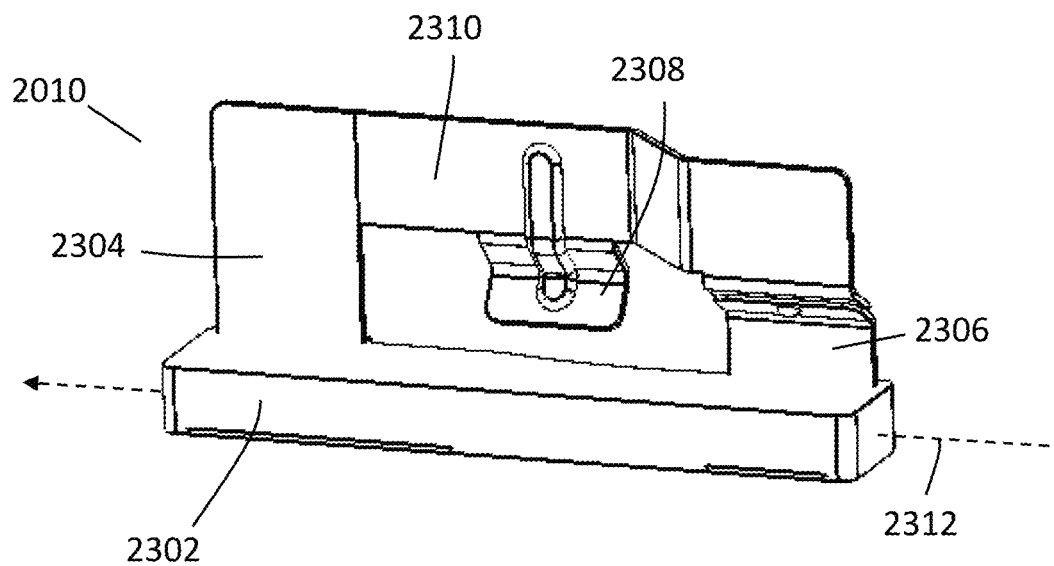
FIGS. 23A and 23B are perspective views of a basecap removal sensor, according to the third set of embodiments.
Figure 23B:
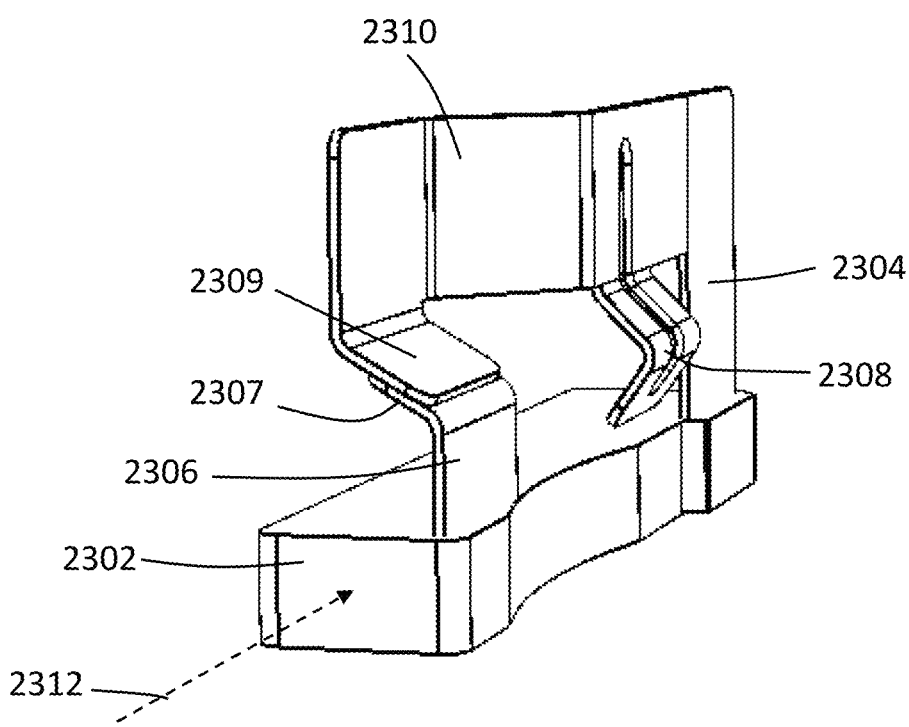

Fourth, main PCB 2082 may include a basecap removal sensor 2010 that allows processing circuit 2008 to detect whether basecap 36 is attached to housing 38, or has been removed by a user. Basecap removal sensor 2010 may be communicatively or electrically coupled with processing circuit 2008. FIGS. 23A and 23B provide a more detailed perspective view of basecap removal sensor 2010. Sensor 2010 comprises a base 2302 that supports a first arm 2304 and a second arm 2306. Base 2302 may be coupled to PCB and may be circumferentially disposed along the proximal surface of PCB. Arms extend proximally away from the base 2302 and may be in a parallel relationship with one another. First arm 2304 is connected to a horizontal lever 2310. In one example, the arm 2304 and lever 2310 forms a L-shape and may be a monolithic unit. Lever 2310 in turn supports an angled tab 2308 and a first contact surface 2309. Surface 2309 may be angled from lever 2307, extending distally and/or radially inward. Tab 2308 is shown suspended from the lever 2310 and disposed between arms 2304 and 2306. Tab 2308 may include an angled portion that extends radially inward towards longitudinal axis 48. Lever 2310 is shown having multi-planar structure where a first portion contiguous with the arm 2304 is along a first radial plane, and a second portion contiguous with the contact surface 2309 is along a second radial plane farther out from longitudinal axis 48 than the first radial plan. The second arm 2306 is connected to a second contact surface 2307. Contact surface 2307 may be angled from the body of the arm 2306, and in some angles, extending proximally and/or radially outward. Contact surfaces 2307, 2309 are shaped and configured to be in a contacting relationship in one configuration, such as when basecap is detached, and in a separated configuration in another configuration, such as, for example, when basecap is attached, or vice versa. First arm 2304, second arm 2306, and the tabs and contact surfaces mounted on both arms may be formed out of metal, or any other suitable flexible and conductive material.

Figure 24A:
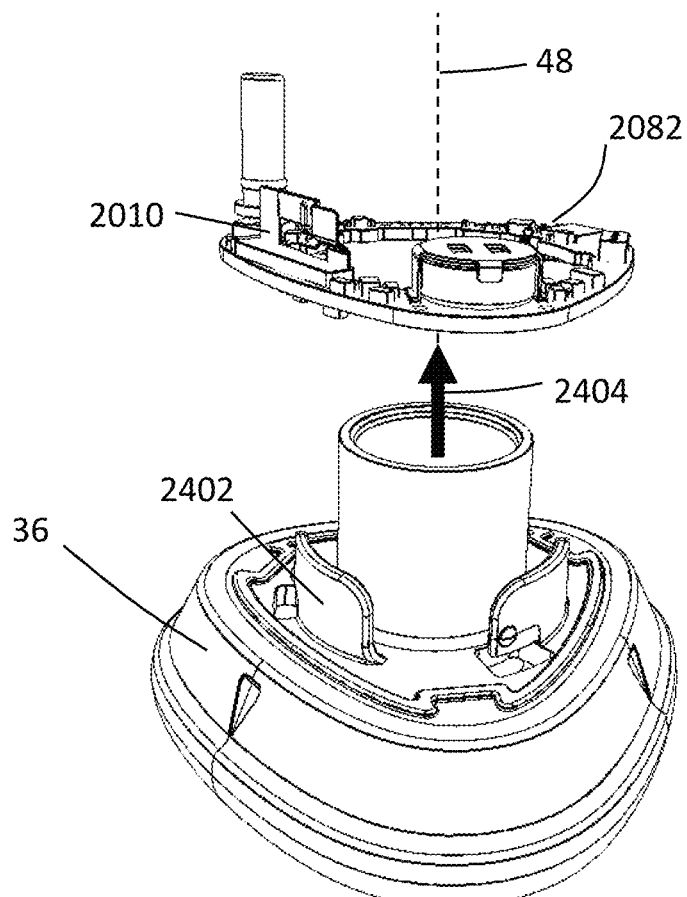
FIG. 24A is a perspective view showing the main PCB and the basecap removal sensor in relation to a removal end cap when the end cap is detached from the injection device, according to the third set of embodiments.
Figure 24B:
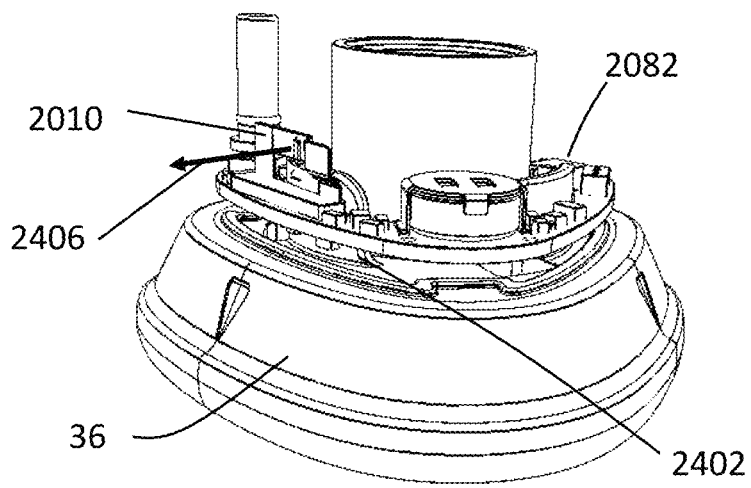
FIG. 24B is a perspective view showing the main PCB and the basecap removal sensor in relation to the removal end cap when the end cap is attached to the injection device, according to the third set of embodiments.

FIG. 24A shows PCB 2082 and basecap removal sensor 2010 in relation to an end cap 36 when end cap 36 is detached from the rest of device 20. For clarity, the housing 38 surrounding and supporting PCB 2082 has been removed. When sensor 2010 is mounted on PCB 2082, the angled tab 2308 points inwardly towards longitudinal axis 48. End cap 36 comprises an internal tab 2402. End cap 36 may be attached to housing 38 by moving end cap 36 in the direction of arrow 2404. FIG. 24B shows PCB 2082 and end cap 36 when end cap 36 is attached. When end cap 36 is attached, internal tab 2402 extends upward through the opening 2003 in PCB 2082 and pushes against angled tab 2308. This pushes angled tab 2308, and the horizontal lever 2310 on which angled tab 2308 is mounted, radially outward in the direction of arrow 2406.

Figure 25B:
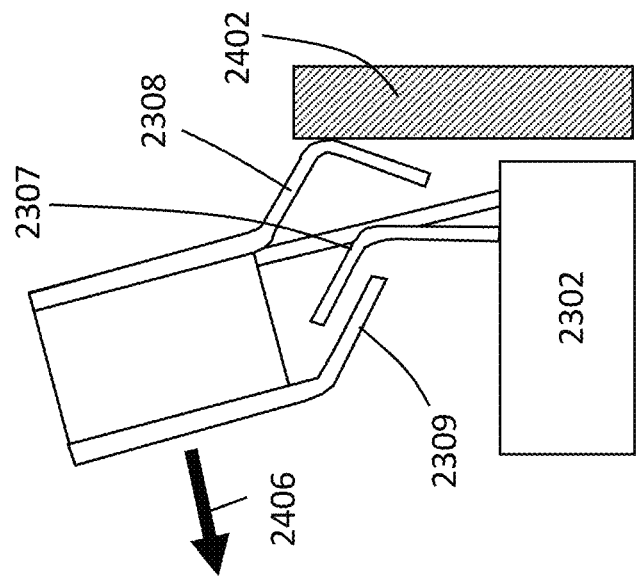
FIG. 25B is a side view showing the basecap removal sensor when the end cap is attached to the injection device, according to the third set of embodiments.
Figure 25A:
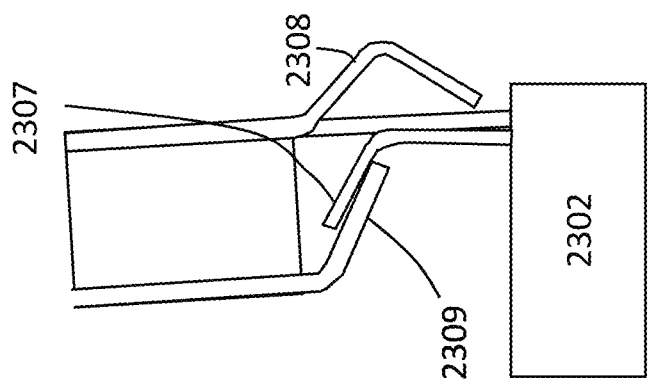
FIG. 25A is a side view showing the basecap removal sensor when the end cap is detached from the injection device, according to the third set of embodiments.

FIGS. 25A and 25B shows basecap removal sensor 2010 when the sensor is viewed from the direction of axis 2312 in FIGS. 23A and 23B. FIG. 25A shows basecap removal sensor 2010 when the sensor is in its neutral state, e.g., when the end cap 36 is detached and therefore internal tab 2402 is not in contact with any portion of sensor 2010. When the sensor 2010 is in this neutral state, first contact surface 2309 is biased in contact with second contact surface 2307 by horizontal lever 2310. The contact between first contact surface 2309 and second contact surface 2307 completes an electrical circuit between first arm 2304 and second arm 2306. When processing circuit 2008 detects that this electrical circuit has been formed, the processing circuit 2008 may determine that the end cap 36 is detached.

FIG. 25B shows basecap removal sensor 2010 when the end cap 36 is attached. When end cap 36 is attached, internal tab 2402 is in contact with and pushes against angled tab 2308 of sensor 2010. This pushing force displaces angled tab 2308, as well as the horizontal lever 2310 on which angled tab 2308 is mounted, outwardly in the direction of arrow 2406. This forces first contact surface 2309 to move relative to the stationary second contact surface 2307, out of contact with second contact surface 2307, thereby breaking the electrical circuit between first arm 2304 and second arm 2306. When processing circuit 2008 detects that this electrical circuit has been broken, the processing circuit 2008 may determine that the end cap 36 is attached.

Fifth, instead of using electrodes that detect skin contact by measuring electrical resistance (as in the first and second set of embodiments), main PCB 2082 instead uses two capacitive pads 2022 and 2023 to detect skin contact. Pads 2022, 2023 are shown as discrete planar structures disposed along the distal surface of the PCB. Capacitive pads 2022 and 2023 may be configured to detect proximity of human tissue by such tissue's effect on an electrical field created by the sensor, e.g., by measuring the effect of such human tissue on the capacitance of an electrical circuit being monitored or measured by the sensor. Capacitance sensors do not require a metallic, electrical terminal that directly contacts skin tissue, and so may be partially or completely sealed behind a protective, non-conducting cover (e.g., made of plastic). This may increase the durability of the capacitance sensor by decreasing seepage of moisture or foreign substances into sensitive electrical components. Capacitance sensors may also reduce the danger of electrostatic discharge damaging sensitive electrical components within the device, since capacitance sensors do not require exposed metallic contacts. Capacitive pads 2022 and 2023 may each individually detect contact with skin tissue, such that processing circuit 2008 may determine when one pad detects contact but the other does not. Although FIGS. 21B and 22B depict only two capacitive pads 2022 and 2023, other embodiments in the third set of embodiments may have less or more capacitive pads. For instance, main PCB 2082 may include only a single capacitive pad, or it may have three, four, five, six, or more capacitive pads.

Sixth, main PCB 2082 in this third set of embodiments comprises an accelerometer 2012 that detects shocks or accelerations caused by initiation of a dispensing event in which syringe assembly 22 is driven by drive mechanism 24 from the storage position to the injection position. Accelerometer 2012 may also detect shocks or accelerations caused by a retraction movement upon completion of the dispensing event in which syringe assembly 22 is driven by the retraction mechanism 26 from the injection position to the retracted position. Accelerometer 2012 may send an output signal to processing circuit 2008 via one or more electrical connections to allow processing circuit to analyze the output signal.

Figure 26:
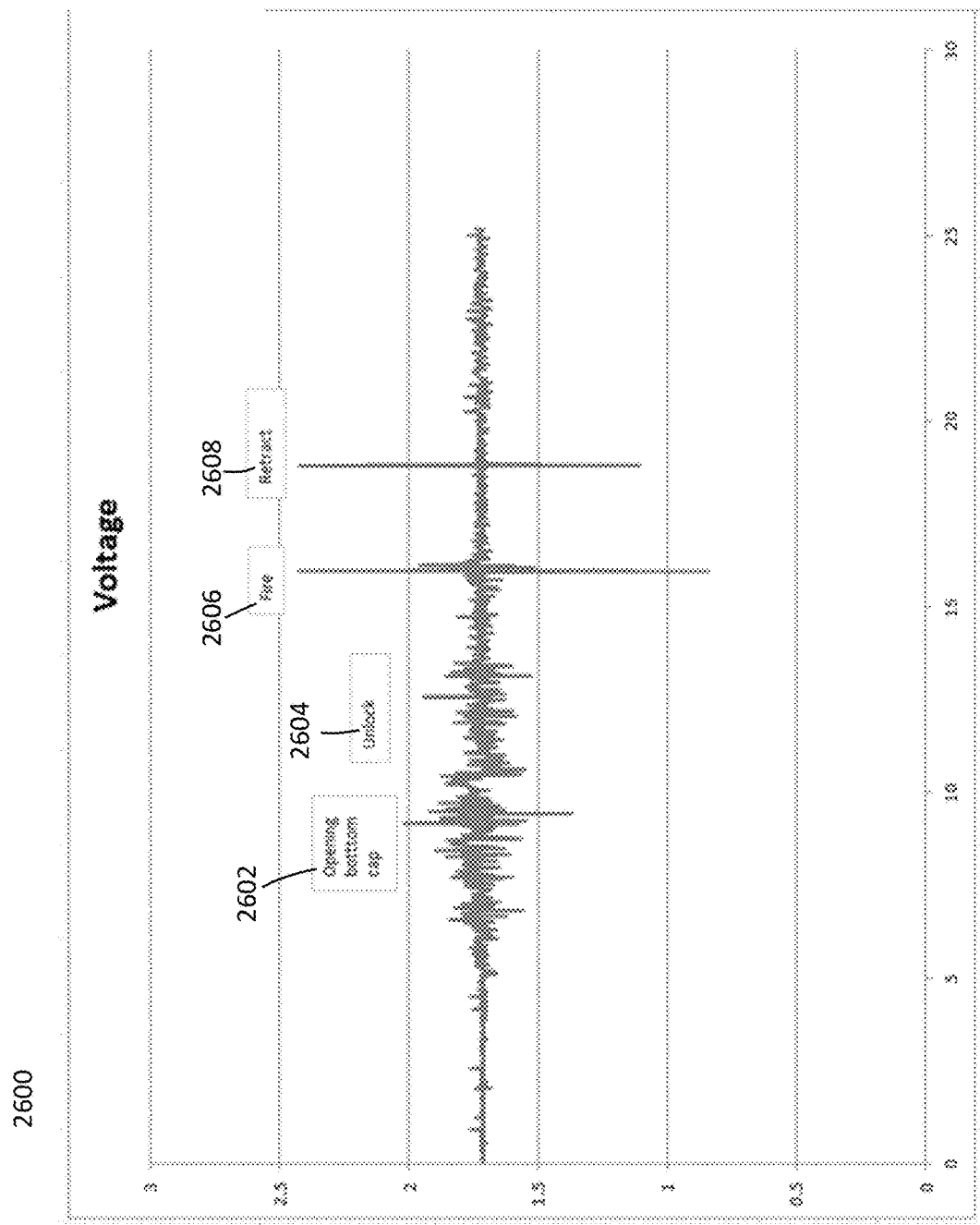
FIG. 26 is a graph showing an exemplary signal output from an accelerometer disposed on the injection device, according to the third set of embodiments.

FIG. 26 depicts a graph showing an exemplary signal output from accelerometer 2012, according to the third set of embodiments. The vertical Y-axis of graph 2600 shows the magnitude of the signal in volts. The x-axis of graph 2600 depicts the passage in time, e.g., in units of seconds. In this example, the signal from accelerometer 2012 is centered around a voltage of approximately 1.75 V. This signal of 1.75 may represent the constant downward acceleration of gravity. Deviations around this constant value indicate accelerations or shocks (other than gravity) imparted to or experienced by device 20 and which are detected by accelerometer 2012 mounted on main PCB 2082. For example, accelerations, vibrations, or shocks caused by removal of the basecap 36 (indicated by label 2062), or by unlocking of actuation button 52 (indicated by label 2064) may be detected by accelerometer 2012.

In some embodiments, processing circuit 2008 may analyze the signal output from accelerometer 2012 to determine a certain condition or state of the device 20, or to detect the occurrence of a certain event or action. For example, processing circuit 2008 may analyze the output signal to discern when the basecap 36 has been removed (e.g., as indicated by the signal at 2062), or when the actuation button 52 has been unlocked (e.g., as indicated by label 2064). Processing circuit 2008 may also be configured to determine when a dispensing event is initiated or completed based on signals from accelerometer 2012, either alone or in conjunction with signals from one or more skin contact sensors.

When a dispensing event is initiated, drive mechanism 24 is activated to drive the syringe assembly 22 from the storage position to the injection position. This driving motion imparts one or more accelerations that may be detected in the signal output from accelerometer 2012. For example, the pushing force imparted by drive mechanism 24 as it drives syringe assembly 22 from the storage position in the proximal direction may cause accelerometer 2012 to detect an acceleration in the distal direction along longitudinal axis 48. When syringe assembly 22 hits its stopping position at its injection position at the end of this driving motion, the sudden stop of syringe assembly 22 may cause accelerometer 2012 to detect an acceleration in the proximal direction along longitudinal axis 48. Either this proximal or distal acceleration (or both) may cause accelerometer 2012 to output a first acceleration spike (indicated by label 2606) that may be detected by processing circuit 2008. This first acceleration spike may be indicative of initiation of a dispensing event.

Similarly, when a dispensing event has been completed, the retraction mechanism 26 is activated to drive the syringe assembly 22 from the injection position to the retracted position. This driving motion imparts one or more accelerations that may also be detected in the signal output from accelerometer 2012. For example, the pushing force imparted by retraction mechanism 26 as it drives syringe assembly 22 from the injection position in the distal direction may cause accelerometer 2012 to detect an acceleration in the proximal direction along longitudinal axis 48. When syringe assembly reaches the retracted position, the sudden stop of syringe assembly 22 may cause accelerometer 2012 to detect an acceleration in the distal direction along longitudinal axis 48. Either this proximal or distal acceleration (or both) may cause accelerometer 2012 to output a second acceleration spike (indicated by label 2068) that may be detected by processing circuit 2008. This second acceleration spike may be indicative of completion of the dispensing event. As used herein, an "acceleration spike" is defined as any artifact in an acceleration or vibration signal output by an accelerometer or vibration sensor (e.g., a piezo sensor) that is indicative of initiation and/or completion of a dispensing event.

Seventh, instead of using an IR sensor 120 mounted on a secondary PCB 84 to measure the temperature of the medication in barrel 30 (as depicted and described in FIGS. 8 and 9A), main PCB 2082 in this third set of embodiments utilizes a temperature sensor 2025 directly mounted on the main PCB 2082 to estimate the temperature of the medication. This temperature sensor may be communicatively or electrically coupled to processing circuit 2008, and outputs a temperature output signal that is received and analyzed by the processing circuit. In one example, the temperature sensor 2025 is mounted to the distal surface of PCB, and in some instances, disposed circumferentially spaced from the pads 2022, 2023. By using a temperature sensor 2025 mounted directly on main PCB 2082, and omitting the secondary PCB 84 entirely, the main PCB 2082 in this third set of embodiments decreases costs and complexity in manufacturing and assembly.

Temperature sensor 2025 may comprise any of a plurality of types of temperature sensors that may be mounted on a PCB, such as but not limited to a thermistor (e.g., a negative temperature coefficient (NTC) thermistor, or a resistance temperature detector (RTD)), a thermocouple, or a semiconductor-based temperature sensor. Temperature sensor 2025 may be configured and positioned to measure a temperature of a thermal ballast. The thermal ballast may comprise all or a portion of the silicon substrate of main PCB 2082 itself. Alternatively, the thermal ballast may comprise a suitable heat sink comprised of other materials (e.g. a polymer) that is mounted on main PCB 2082. The thermal ballast may be is in contact with, or surround all or a portion of, temperature sensor 2025.

The materials, size, shape, and position of the thermal ballast may be selected so that the thermal ballast has a thermal time constant ($\tau_{ballast}$) that approximates that of a thermal time constant of the medication in the barrel 30 ($\tau_{drug}$). As used in the specification and claims herein, the "thermal time constant ($\tau$)" of a body (such as of the thermal ballast, or of the medication within barrel 30) shall be understood to be the constant that satisfies Equation 1 below:

$$\frac{T(t) - T_\infty}{T_i - T_\infty} = e^{-\tau t} \qquad \text{Eq. 1}$$

Where:
T(t)=temperature of the body at time t;
$T_\infty$=ambient temperature of a medium (e.g., of atmosphere) surrounding the body; and
$T_i$=initial temperature of the body In other words, the thermal time constant $\tau$ of a body characterizes how quickly the body's temperature adjusts to match the ambient temperature of its environment—a high thermal constant means the body's temperature adjusts quickly, while a low thermal constant means the body's temperature adjusts slowly. Therefore, when the thermal ballast has a thermal time constant ($\tau_{ballast}$) that approximates that of a thermal time constant of the medication in barrel 30 ($\tau_{drug}$), the temperature of the thermal ballast may be assumed to increase or decrease to match the ambient temperature at approximately the same rate as the temperature of the medication. Since the thermal ballast may be mounted on main PCB 2082, the thermal ballast will generally be exposed to the same ambient temperature as the medication in barrel 30. Therefore, processing circuit 2008 may estimate the temperature of the medication in barrel 30 by measuring the temperature of the thermal ballast, and assuming that the temperature of the medication in barrel 30 is equal to the measured temperature. Thus, main PCB 2082 in this third set of embodiments may estimate the temperature of the medication in barrel 30 without having to position an infrared (IR) sensor or other type of temperature sensor right next to (or in physical contact with) barrel 30. This decreases costs and complexity in manufacturing and assembly, and also decreases the space and form factor requirements of device 20.

In some embodiments, the materials, size, shape, and/or position of the thermal ballast may be selected so that $\tau_{ballast}$ is within 10% of $\tau_{drug}$. In other embodiments, the materials, size, shape, and/or position of the thermal ballast may be selected so that $\tau_{ballast}$ is within 5% of $\tau_{drug}$. In some embodiments where the temperature of the drug needs to be determined to a high accuracy, the materials, size, shape, and/or position of the thermal ballast may be selected so that $\tau_{ballast}$ is within 2% of $\tau_{drug}$. In yet other embodiments, the materials, size, shape, and/or position of the thermal ballast may be selected so that the temperature of the ballast is always within a certain number of degrees (e.g., +/−2° C., or +/−5° C.) of the drug in barrel 30 when both the ballast and the drug are brought from a first, relatively cool storage temperature (e.g., between 36 and 46 degrees Fahrenheit, or 2 and 8 degrees Celsius) to a second, relatively warmer temperature (e.g., to room temperature, or between 65 and 75 degrees Fahrenheit, or 18 and 24 degrees Celsius).

Figure 27:
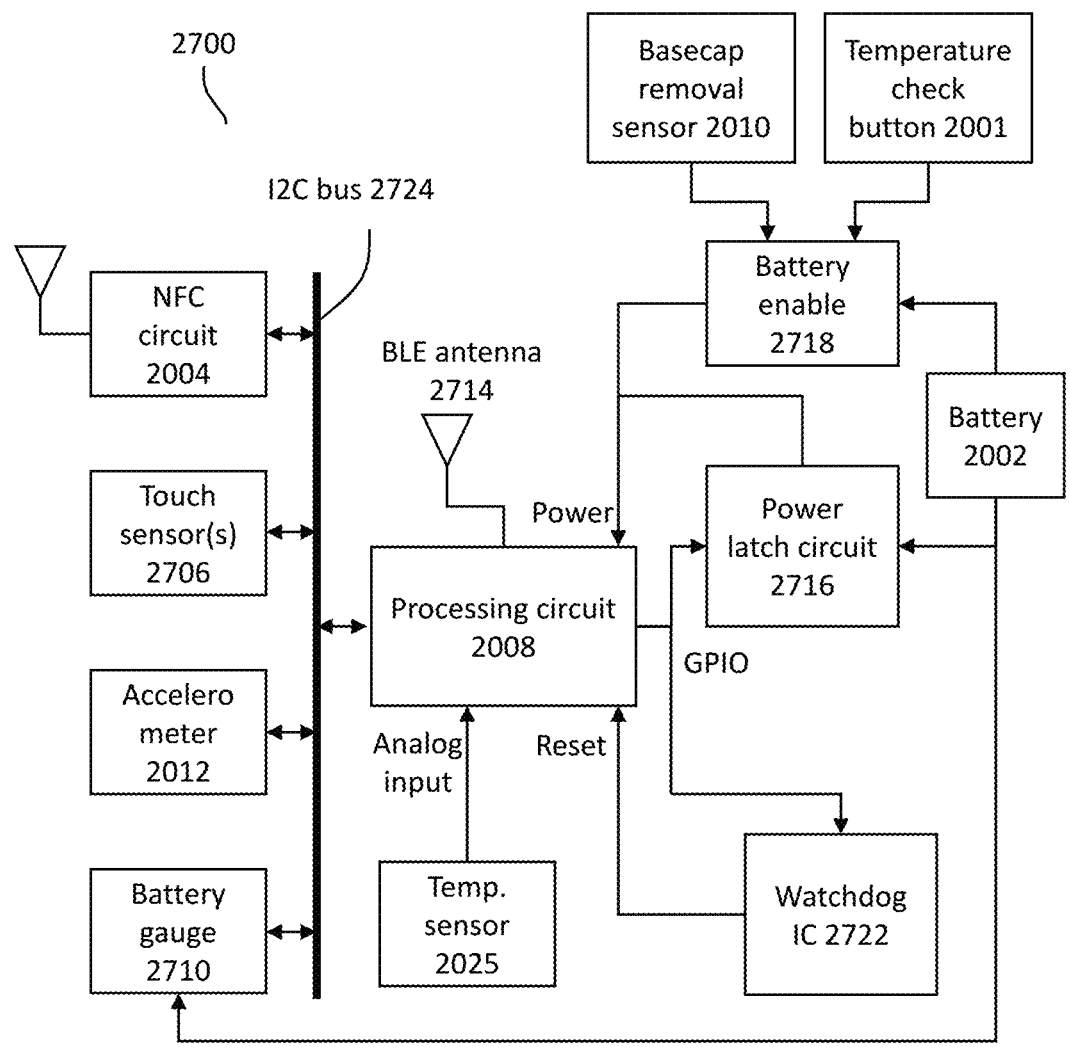
FIG. 27 is a system architecture view of electrical components within the injection device, according to the third set of embodiments.

FIG. 27 provides a system architecture view of the electrical components within device 20 according to the third set of embodiments of device 20. Some or all of these components may be mounted on main PCB 2082, previously depicted in FIGS. 21A, 21B, 22A, and 22B. As previously-discussed and depicted in the aforementioned figures, these electrical components may comprise a processing circuit 2008. In some embodiments, processing circuit 2008 may take the form of a Bluetooth Low Energy (BLE) System on Chip (SOC). Such a BLE SOC may comprise a chip including computational circuitry (e.g., a mini-processor or arithmetic logic unit (ALU)), on-board memory (e.g., non-transitory computer-readable media, such as volatile or non-volatile memory) used to store programming instructions executed by the computational circuitry, and a BLE antenna 2714. Processing circuit 2008 is configured to control and coordinate the functions of the electrical components depicted in FIG. 27.

According to the third set of embodiments, processing circuit 2008 may be powered in one of two ways: it may receive power from battery 2002 via a battery enable circuit 2718, or it may receive power from battery 2002 via a power latch circuit 2716. Battery enable circuit 2718 may be one or more physical circuits that routes power from battery 2002 to processing circuit 2008 when certain conditions are fulfilled, and cuts off power to processing circuit 2008 when those conditions are not fulfilled. In other words, battery enable circuit 2718 can both power on and power off processing circuit 2008 depending on sensed conditions. For example, in some embodiments, battery enable circuit 2718 may route power to processing circuit 2008 when either of two conditions are fulfilled: (i) the basecap removal sensor 2010 detects that basecap 36 has been removed, and/or (ii) the temperature check button 2001 mounted on main PCB 2082 has been pressed and is being held down by a user, or the temperature check button 2001 was pressed within a certain time period in the past, e.g., within the past 45 minutes. Battery enable circuit 2718 may also route power to processing circuit 2008 when both conditions are fulfilled. In some embodiments, battery enable circuit 2718 may consider only condition (i) or (ii), and not the other of condition (ii) or (i). Battery enable circuit 2718 may also be configured to consider other conditions in addition to or in place of the conditions discussed above, such as the device's orientation, sensed shock or acceleration, or temperature. If neither condition is fulfilled, battery enable circuit 2718 may be configured to cut off power to processing circuit 2008.

Power latch circuit 2716 may be one or more physical circuits that receives output signals from processing circuit 2008 via a General Purpose Input/Output (GPIO) pin. Power latch circuit 2716 may be configured to route power from battery 2002 to processing circuit 2008 when it receives a "power latch" signal from processing circuit 2008 via the GPIO pin. This power latch signal may be a simple voltage high or voltage low, or it may be a more complex coded signal comprising multiple voltage highs and/or voltage lows. Once power latch circuit 2716 receives the power latch signal, power latch circuit 2716 will "latch", meaning that it will continue to route power from battery 2002 to processing circuit 2008 regardless of whether power latch circuit 2716 continues to receive the power latch signal. In other words, once power latch circuit 2716 is latched, it will continue to supply power to processing circuit 2008 until the battery 2002 is exhausted (or a timer indicating an expected battery life of battery 2002 expires, thus indicating that battery 2002 is close to being exhausted). Processing circuit 2008 may be configured to send the power latch signal to power latch circuit 2716 under different circumstances, depending on the embodiment.

Although battery enable circuit 2718 and power latch circuit 2716 may take the form of one or more physical circuits that perform the functions described above, they may also take the form of software or firmware instructions stored on non-transitory computer-readable media (e.g., non-volatile memory) that, when executed by a processing circuit, perform the functions described above. For example, main PCB 2082 may mount a secondary, low-power processor that is separate and apart from processing circuit 2008, and which determines when to provide power to processing circuit 2008 from battery 2002.

Processing circuit 2008 may also be connected to an Inter-Integrated Circuit (I2C) bus 2724. I2C bus may in turn be communicatively coupled with multiple electrical components, including a NFC circuit 2004, one or more touch sensor(s) 2706, accelerometer 2012, and a battery gauge 2710.

NFC circuit 2004 may comprise an NFC antenna and on-board non-volatile memory, and may support both passive NFC communication and active NFC communication. Passive NFC communication occurs when NFC circuit 2004 communicates with an external device while NFC circuit 2004 is unpowered, wherein NFC circuit 2004 relies solely on power provided wirelessly by the external device. Active NFC communication occurs when NFC circuit 2004 communicates with an external device while NFC circuit 2004 is powered by an internal power source, e.g., battery 2002. In embodiments where NFC circuit 2004 supports active NFC communication, NFC circuit 2004 may be coupled with battery 2002. NFC circuit 2004 may also be configured to store data and/or programming instructions received via its NFC antenna onto its on-board non-volatile memory in a passive way, that is, without being powered by battery 2002.

Touch sensor(s) 2706 may take the form of capacitive pads 2022 and 2023, as previously-depicted and described in FIGS. 21B and 22B. However, touch sensor(s) 2706 may also take the form of any other type of sensors configured to detect contact with skin tissue, including the electrical resistance sensors 122, 123, and 124 previously-depicted and described in FIG. 9B, and/or the electrical resistance sensors 1722, 1723, and 1724 previously-depicted and described in FIG. 17B. In other words, touch sensor(s) 2706 are not limited to the touch sensors described in relation to the third set of embodiments, but may also include some or all of the skin-contact sensor features described in relation to the first and second set of embodiments.

Accelerometer 2012 may take the form of any circuitry configured to detect shocks, vibrations, and/or accelerations associated with the initiation and/or completion of a dispensing event, as previously-described. For example, accelerometer 2012 may take the form of an accelerometer configured to detect accelerations along one, two, or three axes, or it may take the form of a piezo vibration sensor.

Battery gauge 2710 may be physical circuitry, software, and/or firmware that monitors the remaining power stored in battery 2002 and reports this remaining power level to processing circuit 2008.

Processing circuit 2008 may also be coupled to other electrical components via channels other than the I2C bus 2724. For example, processing circuit 2008 may be coupled with the previously-described temperature sensor 2025 via an analog input pin. Processing circuit may also be coupled with a watchdog integrated circuit (IC) 2722 via a GPIO pin. Watchdog IC 2722 may be an integrated circuit with a continuously running counter. The integrated circuit may be configured to reset or restart processing circuit 2008 (e.g., by sending a "reset" signal, or interrupting power to processing circuit 2008) if the counter expires. The counter may be reset by a check-in signal from processing circuit 2008. Processing circuit 2008 in turn may be configured to periodically send a check-in signal to watchdog IC 2722. Thus configured, watchdog IC 2722 helps ensure that processing circuit 2008 does not get erroneously stuck in a programming loop. By periodically sending a check-in signal to watchdog IC 2722, processing circuit 2008 demonstrates that it is not stuck in an erroneous programming loop or some other fault condition. If watchdog IC 2722 does not receive a check-in signal from processing circuit 2008 by the time the counter expires, watchdog IC 2722 will send a "reset" signal (and/or cut power) to processing circuit 2008 to force processing circuit 2008 to restart itself.

Figure 28:
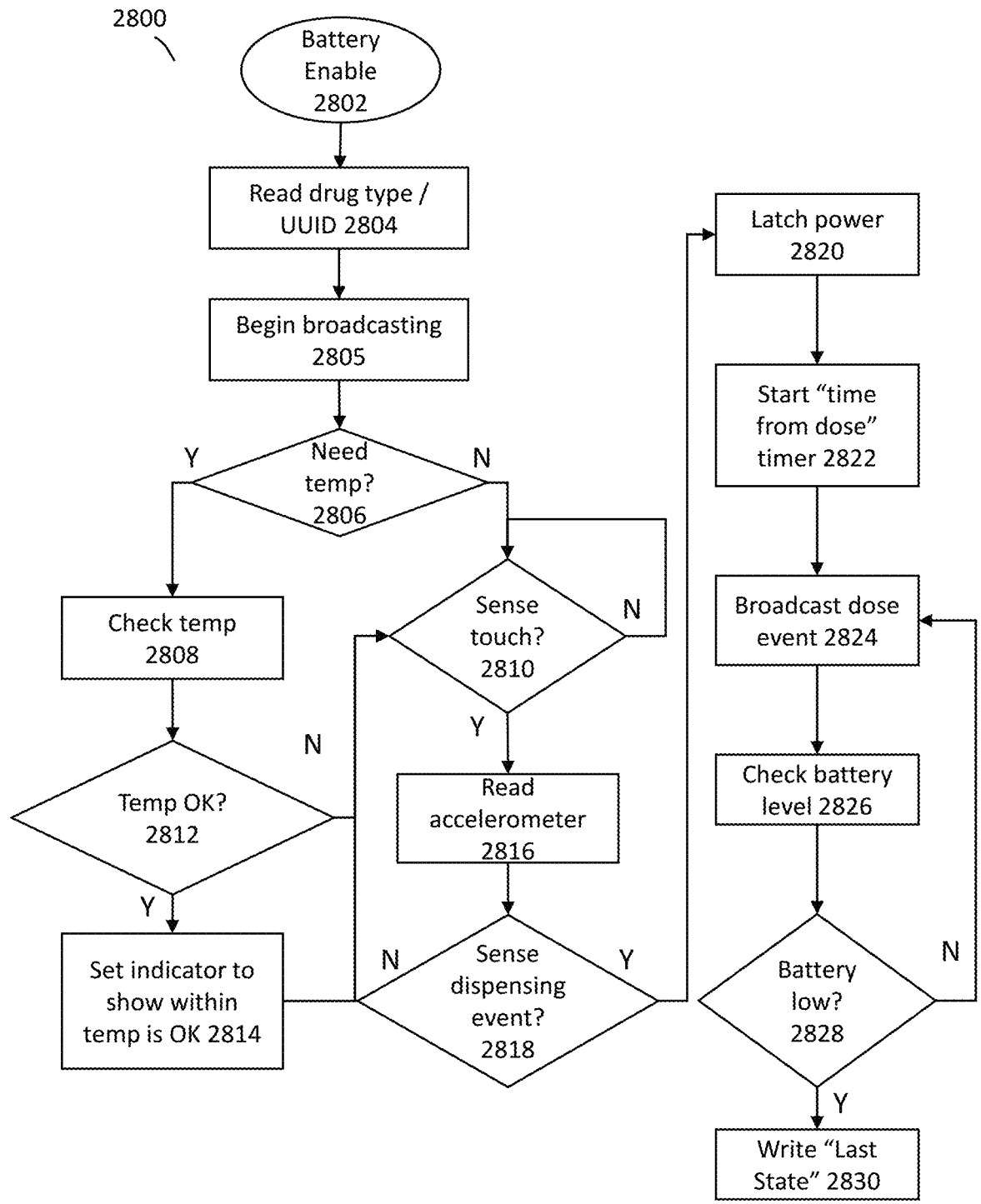
FIG. 28 is a flow-chart depicting an exemplary process implemented by a processing circuit on the injection device, according to the third set of embodiments.

FIG. 28 is a flow-chart showing an exemplary process 2800 implemented by processing circuit 2008 when it receives power, according to the third set of embodiments of device 20. In this exemplary embodiment, if processing circuit 2008 stops receiving power at any point, all progress through process 2800 is lost. Therefore, when processing circuit 2008 receives power again, it restarts at the beginning of process 2008, i.e., at step 2802.

Process 2800 begins at step 2802 when the battery enable circuit 2718 provides power to processing circuit 2008. As previously-discussed, this occurs when either (i) the basecap removal sensor 2010 detects that basecap 36 has been removed, and/or (ii) the temperature check button 2001 mounted on main PCB 2082 has been pressed within a certain time period (e.g., within the last 45 minutes), or is being held down by a user. After processing circuit 2008 starts receiving power, it proceeds to step 2804.

At step 2804, processing circuit 2008 reads a universal unique identifier (UUID) and/or a drug type from memory, e.g., non-volatile and non-transitory computer-readable media. This memory may be non-volatile memory coupled or integrated with processing circuit 2008, and which has been programmed during manufacturing or assembly of device 20. In some embodiments, this memory may be coupled or integrated with NFC circuit 2004.

The UUID may comprise a serial number or sequence of alphanumeric symbols. Depending on the embodiment, the UUID may be unique to a specific device 20, a specific manufacturing lot of device 20 (e.g., a batch of devices manufactured on a specific assembly line on a specific date), and/or to a specific device configuration. The UUID may also specify the type of medication contained within device 20. Alternatively, the memory may store a data field separate from the UUID that specifies the type of medication contained within device 20. In some embodiments, processing circuit 2008 may also read other data and/or programming instructions from the memory.

Some or all of this data (e.g., the UUID, drug type, programming instructions, and/or other data) may be stored on memory coupled or integrated with NFC circuit 2004 instead of processing circuit 2008 to simplify manufacturing and assembly processes. In some embodiments, depending on the configuration of device 20, programming memory coupled or integrated with processing circuit 2008 may require that processing circuit 2008 be powered up. This programming operation may consume precious power stored on battery 2002, thus reducing the useful battery life of the completed device. On the other hand, memory coupled or integrated with NFC circuit 2004 may be programmed with some or all of this data via passive NFC communication, without needing to draw any power from battery 2002. To save power therefore, instructions to be executed by the processing circuit 2008 may be programmed into NFC circuit 2004 via passive NFC communication during manufacturing. Then when processing circuit 2008 is powered up, it may be configured to read the stored data/instructions from the memory of NFC circuit 2004. After processing circuit 2008 reads the UUID, drug type, and/or any other data or programming instructions from memory, processing circuit 2008 proceeds to step 2805.

At step 2805, processing circuit 2008 begins periodically broadcasting, via BLE antenna 2714, wireless signals that communicate the injection device 20's status. These wireless signals may in some embodiments take the form of BLE advertising packets, though other types of wireless signals and wireless protocols may also be used. This wireless signal may be broadcast at certain periodic intervals, such as once every second, or once every five seconds, and may contain data regarding some or all of the following parameters or fields: (i) the device's UUID, (ii) an indication of the drug type, (iii) an indication of whether the basecap is still attached to the device, whether the basecap has been removed from the device, and/or whether the basecap has been removed and re-attached to the device, (iv) an amount of time that has elapsed since the basecap was first removed (e.g., in seconds), (v) a skin contact duration (e.g., an amount of time that the device has been in contact with skin), (vi) an indication of whether a dose has been initiated, and/or whether a dose has been initiated and completed, (vii) a detected dose start time, and/or an amount of time that has elapsed since an initiated dose was completed, (viii) a dose duration, which in some embodiments may be defined as the amount of time between the initiation and completion of a dose event, (ix) a temperature sensed by the temperature sensor 2025, (x) a device orientation as measured by the accelerometer, (xi) a temperature check count, e.g., a number of times that a user has pushed the temperature check button, (xii) an orientation of the device at the time of dose, (xiii) a detected fault or error condition relating to any or all of the temperature sensor, the accelerometer, the skin contact sensors, and/or the basecap removal sensor, (xiv) any data derived or calculated from one or more of the fields (i) through (xiii), and/or (xv) any other device or ambient conditions observed or measured by the device.

These wireless signals may be periodically broadcast by processing circuit 2008 throughout process 2800. At this point in step 2805, some or all of the fields included in the wireless signal may be null or blank until processing circuit 2008 begins receiving and processing data from device 20's onboard sensors. As processing circuit 2008 receives and processes signals from device 20's onboard sensors (e.g., basecap removal sensor 2010, touch sensor(s) 2706, accelerometer 2012, temp. sensor 2025, etc.), it will continually update the transmitted wireless signals to reflect the device's most current state. Processing circuit 2008 then transitions to step 2806.

At step 2806, processing circuit 2008 determines whether the drug stored in device 20 requires a temperature check based on the UUID, drug type, and/or other data and programming instructions. Certain types of drugs that may be administered through device 20 may require a temperature check, while other types of drugs may not require a temperature check. If the stored drug does not require a temperature check, processing circuit 2008 branches to step 2810. If the drug does require a temperature check, processing circuit 2008 branches to step 2808.

At step 2808, processing circuit 2008 checks the temperature measured by temperature sensor 2025. As previously-described, this temperature may be indicative of the temperature of the mediation stored in barrel 30. The sensed temperature is then included in the continual stream of wireless signals being periodically broadcast.

At step 2812, processing circuit compares the measured temperature against pre-set thresholds to determine if the measured temperature satisfies certain pre-defined and pre-stored ideal injection temperature parameters. For example, the measured temperature may satisfy ideal injection temperature parameters when the measured temperature is within an ideal temperature range for injection, e.g., between 65 and 75 degrees Fahrenheit, or 18 and 24 degrees Celsius. In other simpler embodiments, processing circuit may simply determine whether the measured temperature is above a certain minimum temperature threshold (e.g., above 65 degrees Fahrenheit or 18 degrees Celsius), without determining whether the measured temperature is below a certain maximum temperature threshold. If the measured temperature satisfies the ideal injection temperature parameters, processing circuit 2008 branches to step 2814 where it sets an indicator to inform the user of this determination. Such an indicator may comprise one or more LEDs, a light ring, a message on a display, or a panel that slides open to reveal a message or a color on the injection device body. After setting such an indicator, processing circuit 2008 branches to step 2810. If the measured temperature does not satisfy the ideal injection temperature parameters, processing circuit 2008 branches directly to step 2810 without setting the indicator.

At step 2810, the processing circuit 2008 checks to see if the touch sensor(s) 2706 detect contact with skin tissue. If the touch sensor(s) 2706 detect contact, processing circuit 2008 branches to step 2816. If the touch sensor(s) 2706 do not detect contact, the processing circuit 2008 continuously loops back to step 2810 until skin contact is detected. Once again, processing circuit 2008 automatically updates the wireless signals according to the output of touch sensor(s) 2706.

At step 2816, processing circuit 2008 reads the output of accelerometer 2012. In some embodiments of process 2800, processing circuit 2008 does not read or evaluate the output of accelerometer 2012 unless skin contact is detected. This may be accomplished by cutting off power to accelerometer 2012 unless skin contact is detected, such that accelerometer 2012 does not output any acceleration signal unless skin contact is detected. Alternatively, accelerometer 2012 may receive power and output an acceleration signal even when skin contact is not detected, and processing circuit 2008 may be configured to log the skin contact time and duration in memory, but otherwise take no action based on any output signal from accelerometer 2012 until skin contact is detected. By requiring that skin contact be detected before determining that a dispensing event has been detected, processing circuit 2008 mitigates the occurrence of false positives in which processing circuit 2008 records a dispensing event even if no dispensing event has occurred.

At step 2818, processing circuit 2008 determines whether a dispensing event has been initiated and completed based on the output of accelerometer 2012. This determination may be made in different ways, and exemplary logic for making this determination is explained in further detail below in FIGS. 29, 30, 31, and 32. If a completed dispensing event is not detected, processing circuit 2008 branches back to step 2810. If processing circuit 2008 determines that a dispensing event has been both initiated and completed at step 2818, processing circuit 2008 records the initiation and/or completion of the dispensing event in memory. Processing circuit 2008 may also communicate the initiation and/or completion of the dispensing event to a user by setting an indicator, such as one or more LEDs, light rings, or other visual and/or auditory indicators. Thereafter, processing circuit 2008 branches to step 2820.

At step 2820, processing circuit sends a signal to power latch circuit 2716, which causes power latch circuit 2716 to latch on. As previously-described, once power-latch circuit 2716 is latched on, it will continue to route power from battery 2002 to processing circuit 2008 until battery 2002 is exhausted. After power latch circuit 2716 is latched on, processing circuit 2008 continues to step 2822.

At step 2822, processing circuit 2008 starts a time-from-dose counter. This time-from-dose counter may be a counter internal or external to processing circuit 2008 that continuously counts upward at regular periodic intervals, e.g., every second, every 30 seconds, or every minute. In some embodiments, the time-from-dose counter may start counting only when processing circuit 2008 reaches step 2822 (or when power latch circuit 2716 is latched on at step 2820). In other embodiments, the time-from-dose timer may start counting from the moment processing circuit 2008 receives power (e.g., at the battery enable event 2802), and processing circuit 2008 records the current value of the time-from-dose counter at the time processing circuit 2008 reaches step 2822.

At step 2824, processing circuit 2008 updates the wireless signals being broadcast to indicate that a dispensing event has been successfully initiated and completed. As previously-discussed, the wireless signals may include a detected dose start time, and/or an amount of time that has elapsed since an initiated dose was completed. In embodiments where the time-from-dose counter starts counting when processing circuit 2008 reaches step 2822, the broadcasted signals may include the current value of the time-from-dose counter. In embodiments where the time-from-dose counter counts upward continuously from the moment processing circuit 2008 receives power, the broadcasted signals may include the difference between the current value of the time-from-dose counter, and the value of the time-from-dose counter at the time processing circuit reached step 2822.

The periodically broadcasted wireless signals may be received by an external device, such as a mobile device 1250. These wireless signals enable the external device to determine the type or configuration of device 20, the type of medication administered to the patient, the temperature of the medication at the time of administration (or whether or not the medication temperature satisfied ideal injection temperature parameters at the time of administration), and/ or the amount of time that has elapsed since the medication was administered. By subtracting the amount of time that has elapsed since the medication was administered from the current absolute time (e.g., as determined by a clock integrated or in communication with the external device), the external device may also determine an absolute time at which the medication was administered. For example, if the external device receives a wireless signal from a device 20 indicating that medication was administered one hour ago, and if the external device's clock indicates that it is currently 2 pm Eastern Standard Time on Dec. 21, 2018, the external device may determine that the medication was administered at 1 pm Eastern Standard Time on Dec. 21, 2018 by subtracting the elapsed time (1 hour) from the current absolute time.

After each broadcast, processing circuit 2008 monitors the remaining power level in battery 2002 via battery gauge 2710 (step 2826). Processing circuit 2008 then compares the remaining power level against a minimum low battery threshold (step 2828). If the remaining battery power level is greater than the low battery threshold, processing circuit 2008 branches back to step 2824, where it continues to broadcast the wireless signals. If the remaining battery power level is less than or equal to the low battery threshold, processing circuit 2008 may determine that it will soon lack the power to continue actively broadcasting the wireless signals. As a result, processing circuit 2008 branches to step 2830.

At step 2830, processing circuit 2008 writes its "last state" to NFC circuit 2004. This "last state" may comprise information indicating (i) that a dispensing event was initiated and completed, and (ii) the current value of the time-from-dose counter (e.g., X hours, minutes, or seconds) at the time the processing circuit reached step 2830. Since a NFC circuit 2004 may be interrogated even when it is completely unpowered by battery 2002, writing this "last state" to NFC circuit 2004 ensures that an external device will still be able to determine at least these two pieces of information by interrogating NFC circuit 2004. In other words, the external device will still be able to determine that device 20 (i) successfully dispensed its load of medication, and (ii) this medication was dispensed at least X hours, minutes, or seconds ago.

Process 2800 may be modified by re-arranging, deleting, adding, or re-configuring certain steps. For instance, in some embodiments, process 2800 may be configured to refrain from broadcasting wireless signals until after a successful dispensing event has been detected, i.e., not before reaching step 2824. By refraining from broadcasting wireless signals before a dispensing event has been detected, process 2800 may conserve battery power and also minimize signal interference or confusion in environments where other devices are also transmitting and receiving wireless signals. In some embodiments, process 2800 may not continually check battery level 2826, but may instead use a timer to determine when to write the "last state" to NFC circuit 2004 and to shut down. Such a timer may be configured to instruct processing circuit 2008 to write the "last state" and to shut down after a certain time period has passed since the processing circuit 2008 first powered on, or when the processing circuit 2008 first began transmitting wireless signals.

Figure 29:
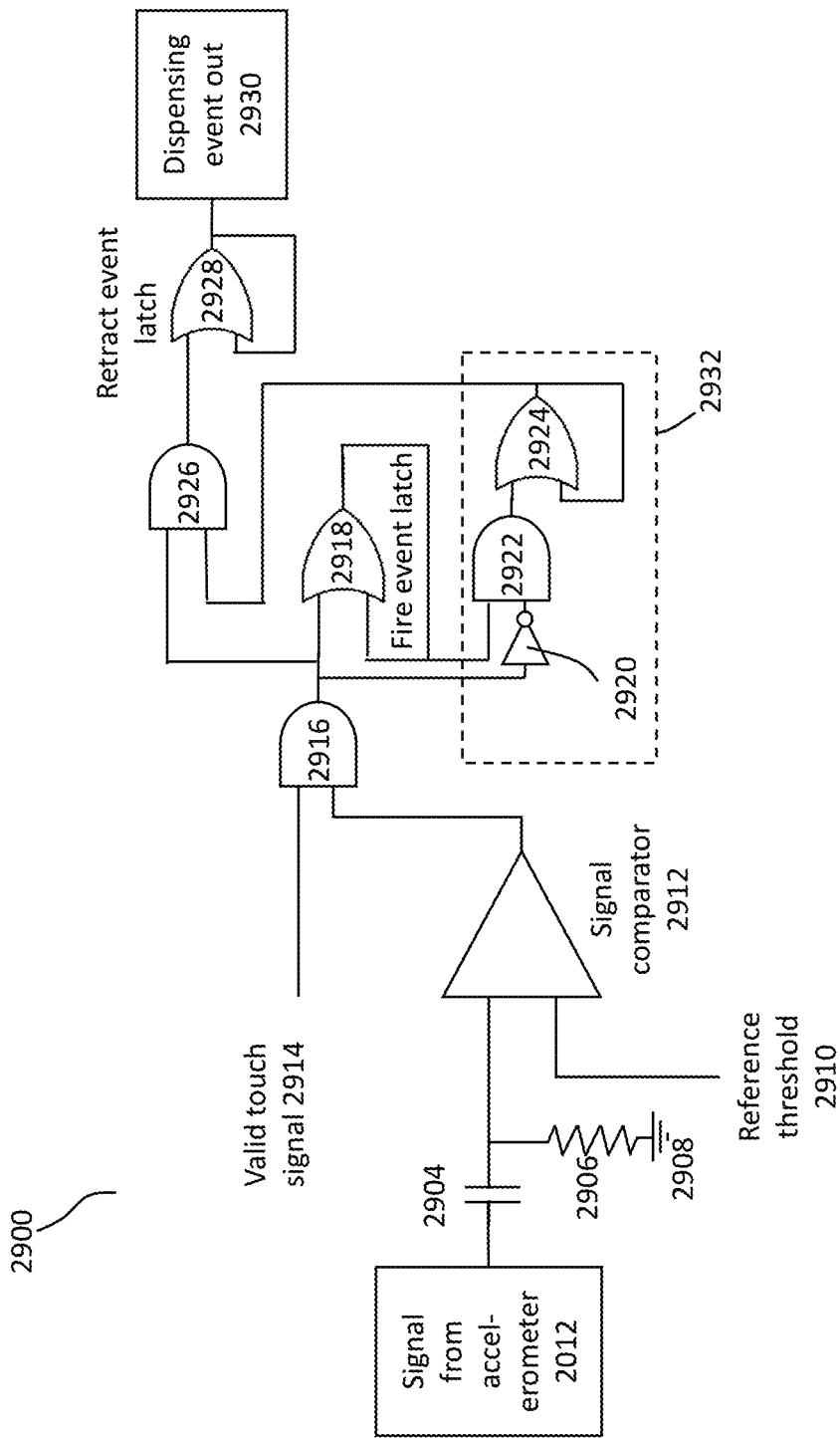
FIG. 29 is a circuit diagram showing exemplary logic for determining whether a dispensing event has been initiated and completed, according to the third set of embodiments.

FIG. 29 depicts an exemplary circuit diagram showing logic for determining whether a dispensing event has been initiated and completed (i.e., step 2818 in process 2800). Although this logic is depicted and described as a circuit diagram, it should be understood that this logic may be implemented as a hardware logic circuit, as software or firmware instructions executing on a processing circuit, or some combination of hardware, software and/or firmware.

As shown in FIG. 29, the output signal from the accelerometer 2012 is first passed through a high pass filter comprising a capacitor 2904 and a resistor 2906 connected to ground 2908. The high pass filter is configured to filter out low-frequency acceleration signals due to gravity, but passes through high-frequency signals from sharp shocks/accelerations indicative of the initiation or completion of a dispensing event. The output of the high pass filter is fed into a first input of signal comparator 2912. The second input of signal comparator 2912 is connected to a reference voltage threshold 2910. Signal comparator 2912 outputs an ON signal (e.g., voltage high) when the output of the low pass filter is greater than or equal to reference voltage threshold 2910—otherwise, signal comparator 2912 outputs an OFF signal (e.g., a voltage low). In other words, the output of signal comparator 2912 turns ON if an acceleration spike is detected, that is, if the high-pass-filtered signal from accelerometer 2012 is greater than or equal to reference voltage threshold 2910. Otherwise, signal comparator 2912 outputs an OFF signal.

The output of signal comparator 2912 is coupled to a first input of an AND gate 2916. The second input of AND gate 2916 is coupled a valid touch signal 2914. Valid touch signal 2914 may be turned ON or OFF based on the output of the touch sensor(s) 2706—an ON signal may indicate valid skin contact is detected, while an OFF signal may indicate that no valid skin contact is detected. Some embodiments of device 20 with multiple skin contact sensors may require that all skin contact sensors detect valid skin contact before turning valid touch signal 2914 ON. Alternatively, some embodiments of device 20 may require only that one of a plurality of skin contact sensors, or a specified number or a specified subset of the plurality of skin contact sensors, detect valid skin contact before turning valid touch signal 2914 ON. The output of AND gate 2916 is therefore ON only when two conditions are fulfilled: (i) an acceleration spike is detected (i.e., the output of signal comparator 2912 is ON) and (ii) a valid touch signal 2914 is detected. The occurrence of both condition (i) and (ii) at the same time indicates that a dispensing event has been initiated, in which syringe assembly 22 is driven by the drive mechanism 24 from the storage position to the injection position. By requiring both conditions (i) and (ii) to be fulfilled before determining that a dispensing event has been initiated, this logic mitigates instances of false positives, where a dispensing event is recorded when in fact none has occurred.

The output of AND gate 2916 is coupled to a first input of OR gate 2918 that functions as a fire event latch. The second input of OR gate 2918 is coupled to the output of OR gate 2918. The output of OR gate 2918 stays OFF until the output of AND gate 2916 outputs an ON signal. Thereafter, OR gate 2918 will remain ON indefinitely until it is reset (e.g., by cutting off power to OR gate 2918). If the output of AND gate 2916 turns OFF again after having turned ON, the output of OR gate 2918 will remain ON. OR gate 2918 is therefore called a fire event latch because it "latches" and stays on indefinitely after a fire event (e.g., initiation of a dispensing event) is detected.

The output of OR gate 2918 is coupled to a debounce circuit 2932. Debounce circuit 2932 outputs an OFF signal until two conditions are fulfilled: (i) the fire event latch outputs an ON signal, indicating that the initiation of a dispensing event has been detected, and (ii) the output of AND gate 2916 outputs an OFF signal. In other words, debounce circuit 2932 turns ON only after a first acceleration spike indicative of initiation of a dispensing event is detected, and said first acceleration spike has passed and is no longer detectible. Once both conditions have been fulfilled, debounce circuit will remain ON indefinitely until it is reset.

Debounce circuit 2932 comprises an inverter 2920, an AND gate 2922, and an OR gate 2924. The output of AND gate 2916 is inverted by inverter 2920 before it is passed to a first input of AND gate 2922. The output of the fire event latch (OR gate 2918) is passed to the second input of AND gate 2922. The output of AND gate 2922 will therefore only turn ON when (i) the fire event latch output is ON and (ii) the output of AND gate 2916 is OFF. The output of AND gate 2922 is coupled to a first input of OR gate 2924. The second input of OR gate 2924 is coupled to the output of OR gate 2924. Therefore, the output of OR gate 2924 is OFF until the output of AND gate 2922 turns ON. Thereafter, OR gate 2924 will remain ON indefinitely until it is reset, e.g., by cutting off power to OR gate 2924. If the output of AND gate 2922 turns OFF again after having turned ON, the output of OR gate 2924 will remain ON.

The output of the debounce circuit 2932 is coupled to a first input of AND gate 2926. The second input of AND gate 2926 is coupled to the output of AND gate 2916. Therefore, the output of AND gate 2926 will turn ON only when two conditions are fulfilled: (i) the debounce circuit 2932 is ON, indicating that a first acceleration spike indicative of initiation of a dispensing event has been detected, and said first acceleration spike has now passed, and (ii) the output of AND gate 2916 is ON, indicating that a second acceleration spike has been detected while valid skin contact is detected. This second acceleration spike is indicative of completion of the dispensing event, in which syringe assembly 22 is driven by retraction mechanism 26 from the injection position to the retracted position in a retraction movement. Once again, by requiring that valid skin contact be detected at the same time as an acceleration spike before recording a retraction movement, this logic mitigates instances of false positives, where a retraction event is recorded when in fact no retraction event has occurred.

The output of AND gate 2926 is coupled to a first input of OR gate 2928 that functions as a retract event latch. The second input of OR gate 2928 is coupled to the output of OR gate 2928. The output of OR gate 2928 therefore remains OFF until the output of AND gate 2926 turns ON, thus indicating that a second acceleration spike indicative of a retraction movement at the completion of the dispensing event has been detected. Once the output of AND gate 2926 turns ON, the OR gate 2928 is latched such that it remains ON indefinitely until it is reset by cutting off power to OR gate 2928 (even if the output of AND gate 2926 subsequently turns OFF). OR gate 2928 is therefore called a "retract event latch" because it latches on indefinitely after a retract event is detected, e.g., a retraction movement in which syringe assembly 22 is driven by retraction mechanism 26 from the injection position to the retracted position. The output of OR gate 2928 is coupled to a dispensing event out signal 2930.

In summary therefore, the dispensing event out signal 2930 turns ON and remains ON only when the following conditions are fulfilled: (i) a first acceleration spike is detected at the same time as a valid skin contact, thus indicating that a dispensing event has been initiated, (ii) said first acceleration spike has passed, and (iii) a second acceleration spike is detected at the same time as a valid skin contact, thus indicating that the dispensing event has been completed and a retraction movement has been detected. When all of these conditions (i)-(iii) are fulfilled, the dispensing event out signal 2930 latches ON, thus indicating that a dispensing event has been both initiated and completed. As discussed above in FIG. 28, once processing circuit 2008 determines that a dispensing event has been both initiated and completed, processing circuit 2008 may record initiation and/or completion of the dispensing event in memory, and also communicate completion of the dispensing event to a user.

FIG. 29 depicts one exemplary way of detecting acceleration spikes, which is to pass the accelerometer's output signal through a high-pass filter and then to compare the filtered signal to a reference voltage threshold—an acceleration spike is detected if the filtered signal is greater than the reference threshold. It should be understood, however, that other ways of detecting acceleration spikes may also be used, either in place of or in addition to the method depicted above in FIG. 29.

Figure 33:
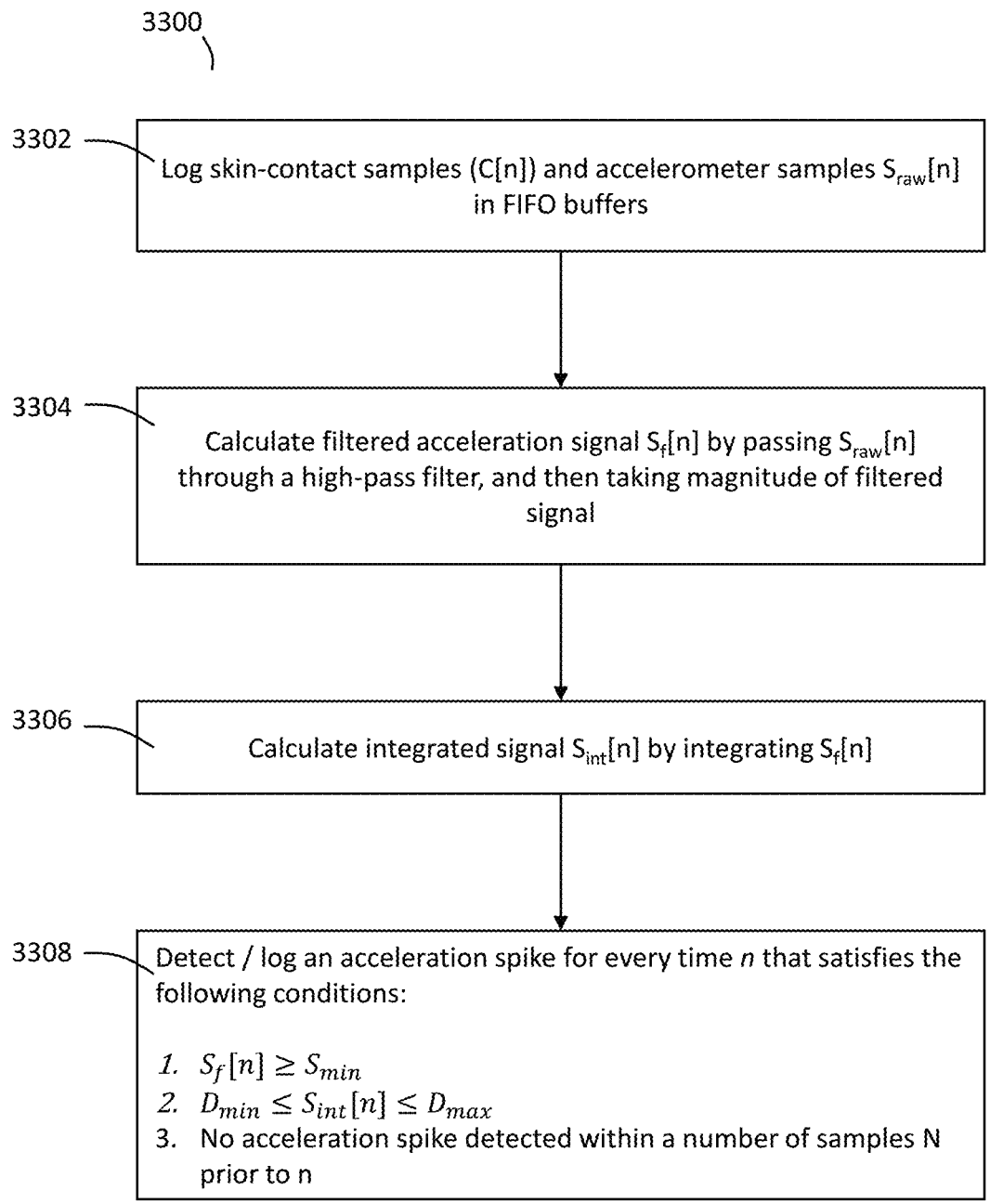
FIG. 33 is a flow-chart depicting an exemplary process for detecting acceleration spikes, according to the third set of embodiments.

Another exemplary process 3300 for detecting acceleration spikes is described and depicted in FIG. 33. At step 3302, processing circuit 2008 logs skin-contact samples, denoted C[n], in a First-In-First-Out (FIFO) buffer. Processing circuit 2008 also logs raw accelerometer samples output from accelerometer 2012, denoted $S_{raw}[n]$, in another FIFO buffer. In this exemplary process 3300, C[n] and $S_{raw}[n]$ are discrete, digital sampled signals. For example, C[n] may include data representing whether skin contact was detected each time touch sensor(s) 2706 was sampled. Depending on the embodiment, C[n] may include a separate sample for each sampling time for each sensor in touch sensor(s), a single sample representing whether any of the sensors detected skin contact, a single sample representing whether all or a subset of the sensors detected skin contact, or other data derived from or calculated the output of one or more of the touch sensor(s) 2706. C[n] may comprise a binary indication of whether contact was detected or not, or data indicative of the certainty of skin contact. $S_{raw}[n]$ may comprise the output signal from accelerometer 2012 at each time sample. The sampling rates for C[n] and $S_{raw}[n]$ may be different according to different embodiments. For example, C[n] may be sampled at a rate of 20 Hz, while $S_{raw}[n]$ may be sampled at a rate of 1600 Hz. As the FIFO buffers for C[n] and $S_{raw}[n]$ fill up, the oldest samples are deleted to make space for new samples.

At step 3304, processing circuit 2008 calculates a filtered acceleration signal $S_f[n]$ by passing $S_{raw}[n]$ through a filter, such as a high-pass or a band-pass filter, and then setting $S_f[n]$ equal to the magnitude of the filtered signal. In some embodiments, processing circuit 2008 may also further process the filtered signal to remove any acceleration detected due to the influence of gravity.

At step 3306, processing circuit calculates an integrated signal $S_{int}[n]$ by integrating $S_f[n]$. This integrated signal $S_{int}[n]$ may be calculated by summing a certain number of samples of $S_f[n]$ within a moving window either before, after, or both before and after time n. The integrated signal $S_{int}[n]$ may also optionally be scaled using a scaling factor that changes according to $S_f[n]$. One exemplary way of calculating $S_{int}[n]$ is described below in Equation 1:

$$S_{int}[n] = \begin{cases} (S_{max} - S_f[n]) \times \sum_{i=0}^{W}(S_f[n+i]), & \text{if } S_f[n] \geq S_{min} \\ 0, & \text{if } S_f[n] < S_{min} \end{cases} \quad \text{Eqn. 1}$$

According to Equation 1, if $S_f[n]$ is less than a certain minimum acceleration signal threshold $S_{min}$ (e.g., 3.5 Gs), then $S_{int}[n]$ shall be set to 0. However, if $S_f[n]$ is greater than $S_{min}$, then $S_{int}[n]$ shall be derived by first integrating (e.g., summing) the next W samples of $S_f[n]$ (e.g., $S_f[n]+S_f[n+1]+S_f[n+2]\ldots+S_f[n+W]$), and then multiplying the result of the integration by a scaling factor. The parameter W may be varied depending on the embodiment—as an example, W may be set to 150 samples.

The scaling factor may be used to allow processing circuit 2008 to adapt its sensitivity depending on how tightly the device 20 is being gripped by the user. The scaling factor may be calculated based on the magnitude of $S_f[n]$. For instance, in this embodiment, the scaling factor is calculated using the term $S_{max}-S_f[n]$, where $S_{max}$ is a constant. $S_{max}$ may, in some embodiments, be set to equal the maximum measurable acceleration signal by accelerometer 2012 (e.g., 8 Gs). The scaling factor helps processing circuit 2008 adapt its sensitivity to sensed acceleration in different circumstances. For instance, when device 20 is being gripped tightly by a user, the detected acceleration signals may be heavily damped—in such a circumstance, the scaling factor will be larger. When device 20 is being gripped loosely, the detected acceleration may be less heavily damped—in such a circumstance, the scaling factor will be smaller. Other ways of calculating the scaling factor are also possible. In general, any method of calculating the scaling factor where an increase in $S_f[n]$ leads to a smaller scaling factor (and vice versa) may be used.

At step 3308, processing circuit 2008 detects or logs an acceleration spike for every time n that satisfies the following conditions:

(1) $S_f[n] \geq S_{min}$
(2) $D_{min} \leq S_{int}[n] \leq D_{max}$
(3) No acceleration spike is detected within a number of samples N prior to n.

The purpose of condition (1) is to ensure that an acceleration spike is only detected at a time when the filtered acceleration signal $S_f[n]$ is greater than a minimum threshold (e.g., 3.5 Gs).

The purpose of condition (2) is to ensure that the integrated signal $S_{int}[n]$ is between a certain minimum threshold $D_{min}$ (e.g., 2.5) and a certain maximum threshold $D_{max}$ (e.g., 8). The values 2.5 and 8 are exemplary only and may be changed depending on the embodiment. If $S_{int}[n]$ is too small (i.e., less than $D_{min}$), the acceleration detected at S[n] is unlikely to correspond to an acceleration spike because it is too transient and/or not powerful enough to be caused by initiation and/or completion of a dispensing event. If $S_{int}[n]$ is too large (i.e., larger than $D_{max}$), the acceleration detected at S[n] is also unlikely to correspond to an acceleration spike because the device is being subject to acceleration forces that are too powerful or too sustained to be caused by initiation and/or completion of a dispensing event. Such powerful and/or sustained accelerations may be caused instead by, for example, a user dropping the device 20 onto a hard surface, or the device 20 being jostled during handling or transportation.

The purpose of condition (3) is to ensure that once an acceleration spike is detected, processing circuit 2008 stops looking for another acceleration spike for at least N samples. For example, processing circuit 2008 may be configured to stop looking for acceleration spikes for one second after detecting a first acceleration spike. This mitigates the occurrence of false positives, where noise or vibrations from a single firing or retraction event leads to detection of multiple acceleration spikes.

Process 3300 is exemplary only, and may be modified in different ways. For example, step 3304 may be omitted such that the integrated signal $S_{int}[n]$ is calculated directly from $S_{raw}[n]$ instead of $S_f[n]$. Step 3306 may be modified by calculating $S_{int}[n]$ without using a scaling factor, or using a scaling factor different than the one in Equation 1. Step 3306 may also be modified by calculating $S_{int}[n]$ for all values of n, and not only those for which $S_f[n]$ is greater than $S_{min}$. Some embodiments may utilize only a maximum threshold $D_{max}$ and no minimum threshold $D_{min}$ when screening $S_{int}[n]$ in condition 2; other embodiments may utilize only a minimum threshold $D_{min}$ and no maximum threshold $D_{max}$. Furthermore, $S_{int}[n]$ may also be calculated by integrating or summing values of $S_f[n]$ that precede the time n, in addition to or in place of integrating or summing values of $S_f[n]$ that follow the time n.

Process 3300 may also be modified such that $S_{int}[n]$ is calculated by integrating (and optionally scaling) $S_f[n]$ in step 3306 only when the currently received value of $S_f[n]$ represents a recent peak. A currently received sample of $S_f[n]$ represents a recent peak when it is the highest sample received within a recent number N of samples (e.g., N could be set to 1,000 accelerometer samples). This requirement that $S_{int}[n]$ be calculated only if $S_f[n]$ is a recent peak may be imposed in addition to or in place of the previously-described conditions for calculating $S_{int}[n]$, e.g., that $S_f[n]$ be greater than or equal to $S_{min}$. By requiring that $S_{int}[n]$ be calculated only when a recent peak value for $S_f[n]$ is received, process 3300 may mitigate the occurrence of false positives where aftershocks or after-vibrations from dropping or striking the device are mistaken as acceleration spikes indicative of initiation and/or completion of a dispensing event. In other words, samples for $S_f[n]$ that do not represent recent peak values, and therefore may be indicative of aftershocks or fading vibrations from dropping or striking the device, are rendered ineligible for consideration as potential acceleration spikes indicative of initiation and/or completion of a dispensing event. In some embodiments, step 3306 may be modified further still such that the number N of samples could be extended if further samples of $S_f[n]$ are received that are greater than $S_{min}$ but less than the recent peak. This means that instead of strictly considering only the last N samples when computing the recent peak, process 3300 may consider a larger number of recent samples if the last few samples were greater than $S_{min}$.

Other methods for detecting acceleration spikes may also be used. For instance, such acceleration spikes may be detected by analyzing the frequency content of the signal output by accelerometer 2012, e.g., by processing the output signal using a Fast Fourier Transform (FFT). If the frequency content of the accelerometer output signal above a certain frequency threshold, or within a certain frequency range, exceeds a pre-set threshold, processing circuit 2008 may determine that an acceleration spike has been detected. Yet another way to detect acceleration spikes may be to differentiate the accelerometer output signal. If the differential of the output signal has a magnitude greater than a certain threshold, processing circuit may determine that an acceleration spike has been detected. In general, any process or algorithm for detecting an acceleration spike indicative of a sharp shock or vibration experienced by device 20 may be used by processing circuit 2008. Any of these processes or algorithms for detecting an acceleration spike may be used in the processes depicted and described in FIGS. 30, 31, and 32.

Figure 30:
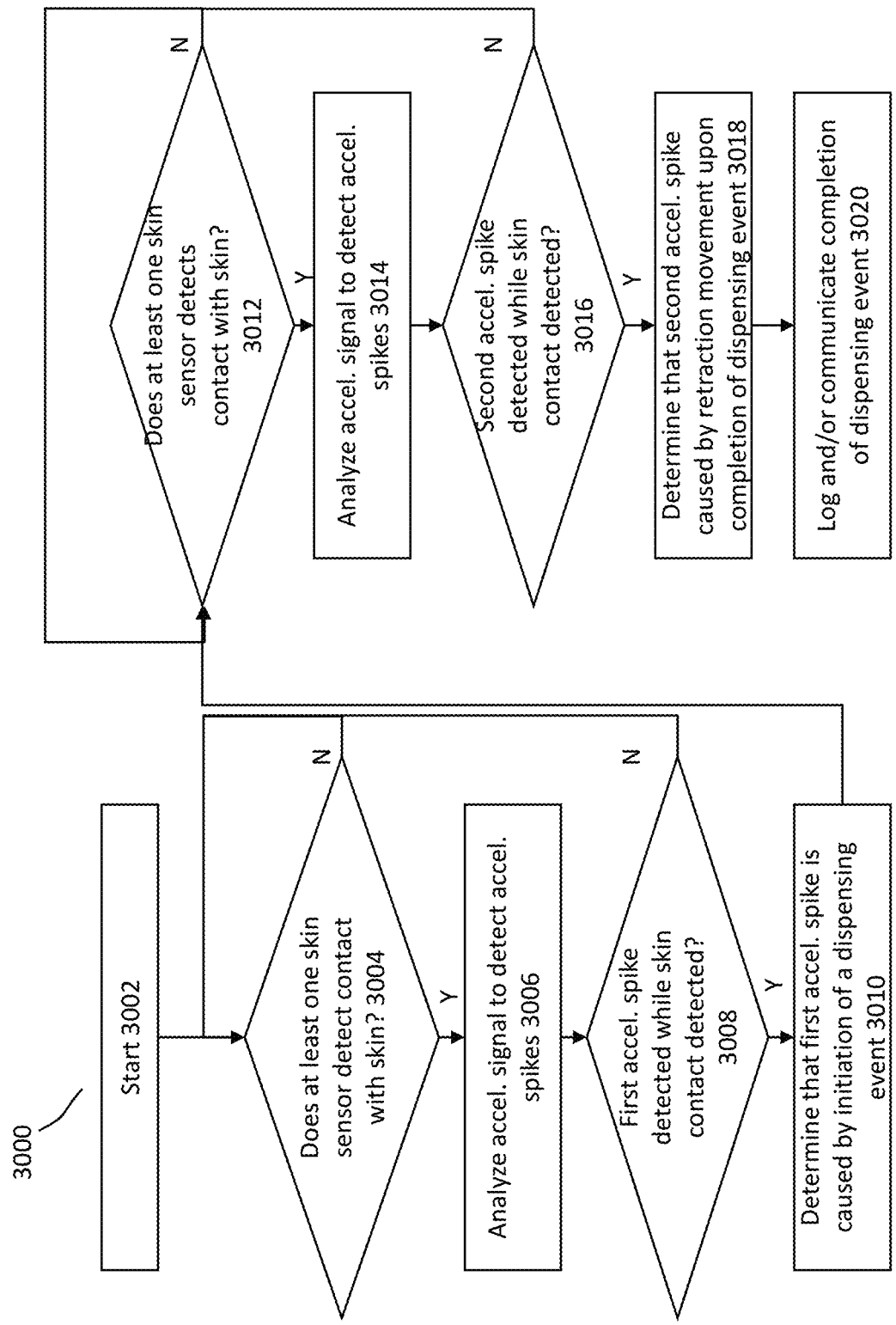
FIG. 30 is a flow-chart depicting an exemplary process for detecting the initiation and completion of a dispensing event, according to the third set of embodiments.

FIG. 30 is a flow-chart showing another exemplary process 3000 that may be implemented by processing circuit 2008 to detect the initiation and completion of a dispensing event (e.g., step 2818 in process 2800), according to the third set of embodiments. Process 3000 may be similar to the logic illustrated in FIG. 29, but may also be different in certain respects.

After starting at step 3002, processing circuit 2008 branches to step 3004 where it evaluates whether at least one skin contact sensor (e.g., at least one, a specified number, a specified subset, or all of touch sensor(s) 2706) detects contact with skin. If yes, processing circuit 2008 branches to step 3006, where processing circuit reads or analyzes the acceleration signal output by accelerometer 2012 to detect acceleration spikes. If not, processing circuit 2008 continually loops back to step 3004 until skin contact is detected. Processing circuit 2008 does not read or analyze any signal output by accelerometer 2012 until skin contact is detected, thus mitigating false positives. Once again, this may be accomplished by cutting off power to accelerometer 2012 such that it does not output any signal unless skin contact is detected. Alternatively, accelerometer 2012 may receive power and output an acceleration signal to processing circuit 2008 even when skin contact is not detected, but processing circuit 2008 may be configured to not proceed to step 3006 unless skin contact is detected.

At step 3006, processing circuit 2008 reads or analyzes the acceleration signal output by accelerometer 2012 to detect acceleration spikes. This may be done using any of the processes or methods for detecting acceleration spikes described previously. After analyzing the accelerometer output signal, processing circuit 2008 may branch to step 3008.

At step 3008, processing circuit 2008 determines whether a first acceleration spike was detected while skin contact was detected. If not, processing circuit 2008 branches back to step 3004. If yes, processing circuit branches to step 3010, where processing circuit 2008 determines that the first acceleration spike was likely caused by initiation of a dispensing event. Processing circuit 2008 therefore records the initiation of the dispensing event by setting an indicator in memory or by setting a logic circuit and proceeds to step 3012.

At step 3012, processing circuit 2008 again evaluates whether at least one skin contact sensor (e.g., at least one, a specified number, a specified subset, or all of touch sensor(s) 2706) detects contact with skin. If yes, processing circuit 2008 branches to step 3014. If not, processing circuit 2008 continually loops back to step 3012 until skin contact is detected. Once again, processing circuit 2008 does not read or evaluate any signal output from accelerometer 2012 until skin contact is detected.

At step 3014, processing circuit again reads or analyzes the acceleration signal output by accelerometer 2012 to detect acceleration spikes. This analysis may be conducted using any of the methods discussed previously.

At step 3016, processing circuit 2008 determines whether a second acceleration spike was detected while skin contact was detected. If not, processing circuit 2008 branches back to step 3012. If yes, processing circuit 2008 branches to step 3018, where processing circuit 2008 determines that the second acceleration spike was likely caused by a retraction movement at the completion of the dispensing event. Processing circuit 2008 therefore records the completion of the dispensing event and proceeds to step 3020.

At step 3020, processing circuit 2008 logs and/or communicates the initiation and completion of the dispensing event. This may be done by recording the dispensing event in memory, and/or broadcasting wireless signals announcing the completion of the dispensing event, as described previously. Alternatively or in addition, processing circuit 2008 may indicate that the dispensing event has been completed by lighting or extinguishing one or more LEDs, emitting a sound, or via any other visual, haptic, or auditory indicator to the user.

Figure 31:
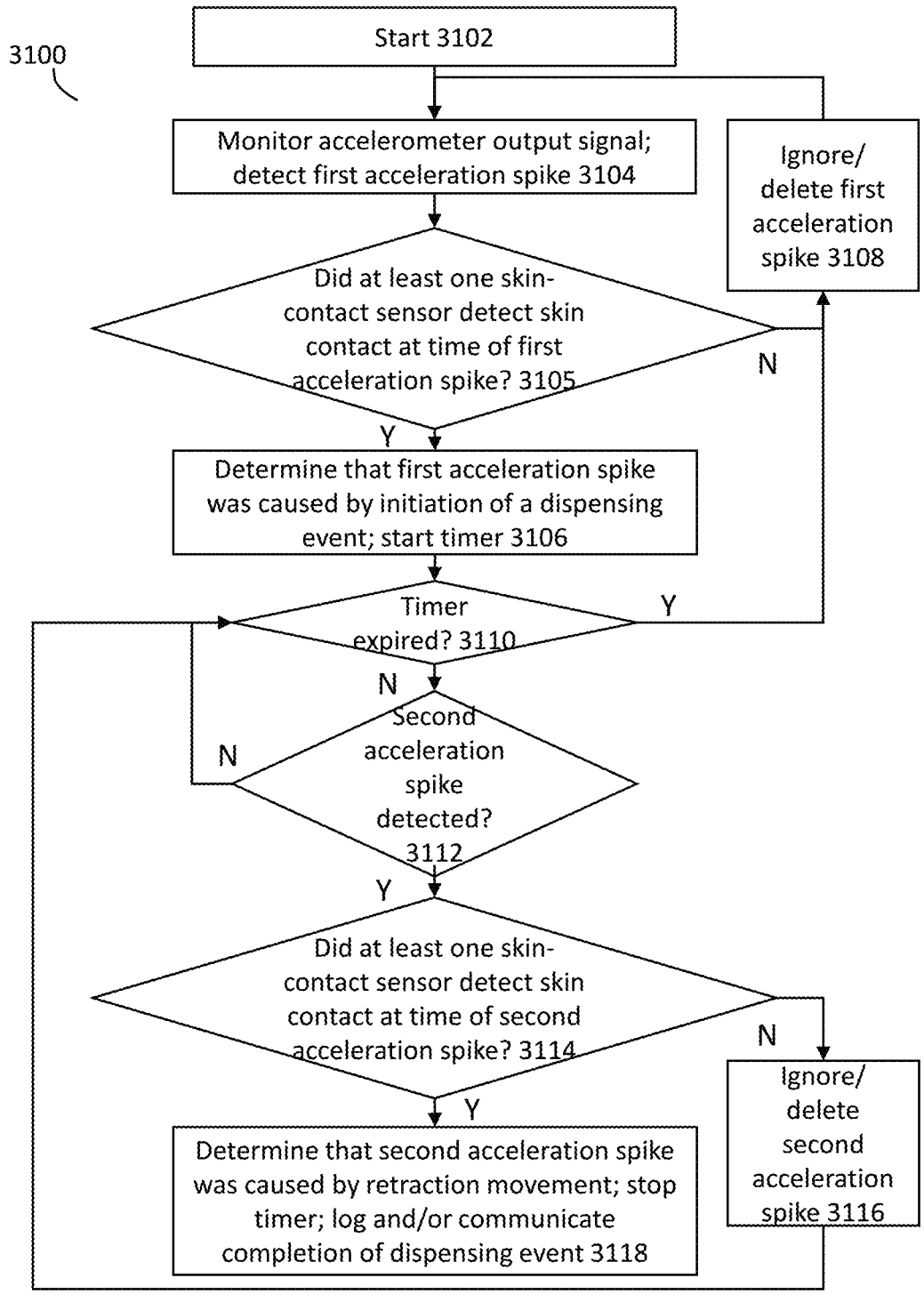
FIG. 31 is a flow-chart depicting another exemplary process for detecting the initiation and completion of a dispensing event, according to the third set of embodiments.

FIG. 31 is a flow-chart showing another exemplary process 3100 that may be implemented by processing circuit 2008 to detect the initiation and completion of a dispensing event (e.g., step 2818 in process 2800), according to the third set of embodiments. Process 3100 may be similar to the logic illustrated in FIGS. 29 and 30, but may also be different in certain respects. In particular, process 3100 uses a timer to ensure that a second acceleration spike is detected within a pre-set time after a first acceleration spike is detected before a dispensing event is determined to be completed. If no second acceleration spike is detected within the pre-set time, the processing circuit 2008 ignores or deletes the first acceleration spike. Process 3100 also reverses the order of operations discussed in FIGS. 29 and 30: rather than continuously monitoring for a skin contact from at least one touch sensor(s) 2706, and reading/evaluating the signal from accelerometer 2012 only if skin contact is detected, process 3100 instead continuously reads/evaluates the signal from accelerometer 2012 for an acceleration spike, and only reads/evaluates the signal(s) from the at least one touch sensor(s) 2706 if an acceleration spike is detected.

After starting at step 3102, processing circuit 2008 branches to step 3104 where it continuously or periodically reads, monitors, and/or evaluates the signal output from accelerometer 2012, regardless of whether any skin contact was detected. This differs from the logic described above in FIG. 30, where the processing circuit does not read, monitor, and/or evaluate any signal from accelerometer 2012 until skin contact is detected. The processing circuit 2008 may analyze the signal from accelerometer 2012 for acceleration spikes using any of the techniques discussed previously. Once a first acceleration spike is detected, processing circuit 2008 proceeds to step 3105. Processing circuit 2008 may also optionally log the occurrence of this first acceleration spike in memory.

At step 3105, processing circuit 2008 determines whether at least one skin-contact sensor (e.g., at least one, a specified number, a specified subset, or all of touch sensor(s) 2706) detected skin contact at the time the first acceleration spike was detected. If not, processing circuit 2008 branches to step 3108 where it ignores the first acceleration spike, or deletes the memory record logging the occurrence of the first acceleration spike, and then branches back to step 3104. If yes, processing circuit 2008 branches to step 3106.

At step 3106, processing circuit 2008 determines that the first acceleration spike was caused by initiation of a dispensing event, in which syringe assembly 22 is driven by the drive mechanism 24 from the storage position to the injection position. Processing circuit 2008 also starts a timer that counts down from a pre-set duration, e.g., a specified number of seconds. After starting the timer, processing circuit 2008 proceeds to step 3110.

At step 3110, processing circuit 2008 determines whether the timer has expired. If yes, processing circuit 2008 branches to step 3108. If not, processing circuit 2008 proceeds to step 3112.

At step 3112, processing circuit 2008 continuously or periodically reads, monitors, and/or evaluates the signal output from accelerometer 2012 for a second acceleration spike, regardless of whether any skin contact was detected. If no second acceleration spike is detected, processing circuit 2008 branches back to step 3110 where it evaluates whether the timer has expired. If a second acceleration spike is detected, processing circuit 2008 branches to step 3114. Processing circuit 2008 may also optionally log the occurrence of this second acceleration spike in memory. Processing circuit 2008 thus continually loops back-and-forth between steps 3110 and 3112 until either the timer expires (in which case processing circuit 2008 branches to step 3108) or a second acceleration spike is detected (in which case processing circuit 2008 branches to step 3114).

At step 3114, processing circuit 2008 determines whether at least one skin-contact sensor (e.g., at least one, a specified number, a specified subset, or all of touch sensor(s) 2706) detected skin contact at the time the second acceleration spike was detected. If not, processing circuit 2008 branches to step 3116 where it ignores the second acceleration spike, or deletes the memory record logging the occurrence of the second acceleration spike, and then branches back to step 3110. If yes, processing circuit 2008 branches to step 3118.

At step 3118, processing circuit 2008 determines that the second acceleration spike was caused by a retraction movement at the completion of the dispensing event. Processing circuit 2008 then stops the timer, logs the initiation and completion of the dispensing event in memory, and/or communicates the initiation and/or completion of the dispensing event to an external device or to a user.

Figure 32:
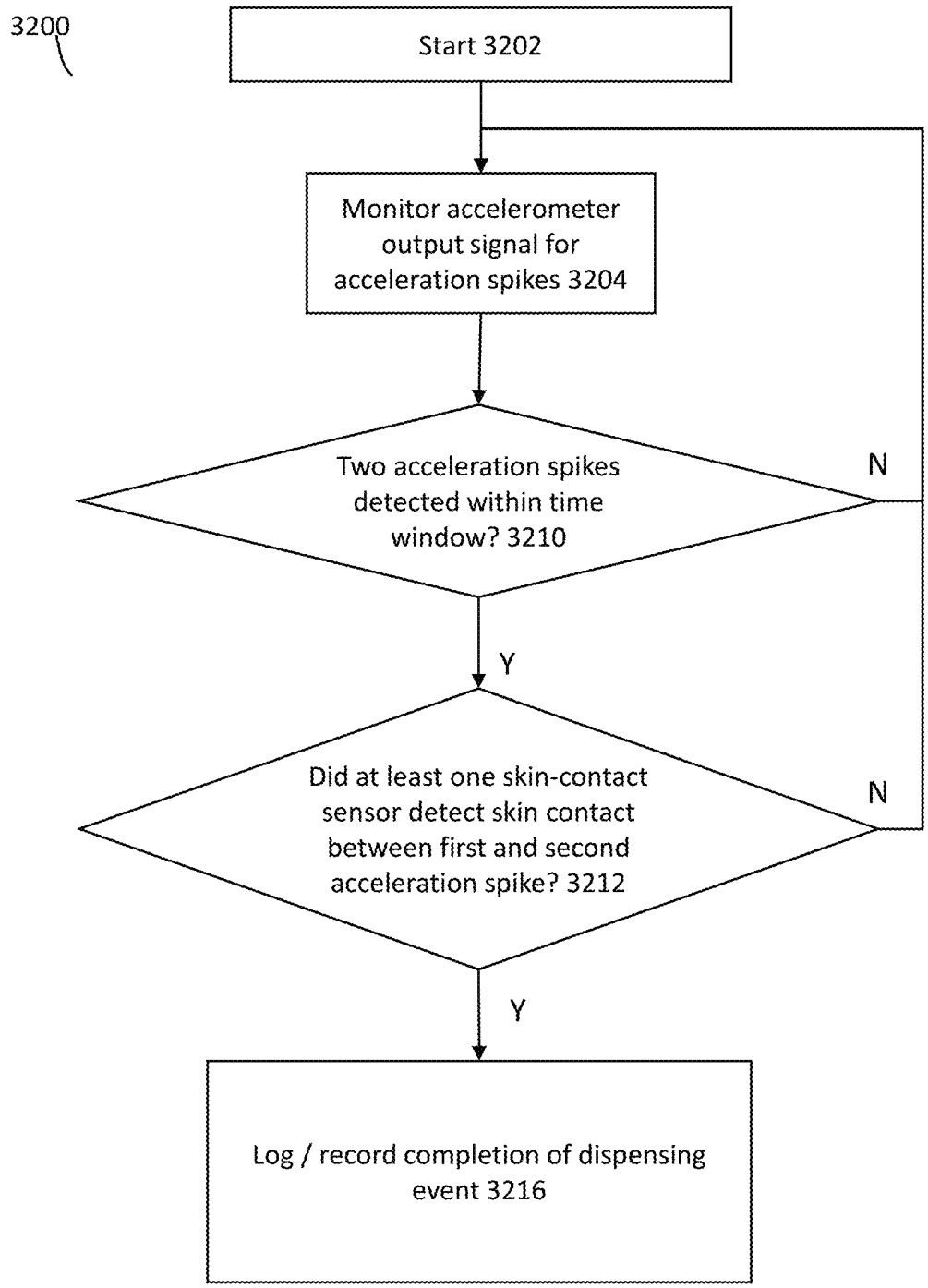
FIG. 32 is a flow-chart depicting another yet exemplary process for detecting the initiation and completion of a dispensing event, according to the third set of embodiments.

FIG. 32 is a flow-chart showing yet another exemplary process 3200 that may be implemented by processing circuit 2008 to detect the initiation and completion of a dispensing event (e.g., step 2818 in process 2800), according to the third set of embodiments. Process 3200 may be similar to the logic illustrated in FIGS. 29, 30, and 31, but may also be different in certain respects. In particular, process 3200 imposes a requirement that two acceleration spikes fit within a certain time window before determining that a dispensing event has been initiated and completed. Process 3200 also requires that at least one skin-contact sensor detect skin contact during the time period between the first and second acceleration spike before determining that a dispensing event has been successfully initiated and completed.

After starting at step 3202, processing circuit 2008 proceeds to step 3204, where it continuously reads, monitors, and/or evaluates the signal output from accelerometer 2012 for acceleration spikes. The processing circuit 2008 may analyze the signal from accelerometer 2012 to detect acceleration spikes using any of the techniques discussed previously.

At step 3206, processing circuit 2008 determines whether two acceleration spikes were detected that fit within a specified time window. If so, processing circuit branches to step 3212—if not, processing circuit 2008 branches back to step 3204. For example, processing circuit 2008 may branch to step 3212 only if two acceleration spikes were detected that occurred no less than a minimum time threshold $T_{min}$ (e.g., 1 second) apart. Alternatively, or in addition, processing circuit 2008 may branch to step 3212 only if two acceleration spikes were detected that occurred no more than a maximum time threshold $T_{max}$ (e.g., between 5 and 10 seconds) apart in time. In some embodiments, the time window may comprise a maximum time threshold $T_{max}$ only and no minimum time threshold; said another way, the minimum time threshold $T_{min}$ may be set to 0 seconds.

At step 3212, processing circuit 2008 determines whether at least one skin-contact sensor (e.g., at least one, a specified number, a specified subset, or all of touch sensor(s) 2706) detected skin contact during the time period between the first and second acceleration spike. Some illustrative criteria for evaluating skin contact are listed below:

(1) Skin contact detected during entire period between the first and second acceleration spike.
(2) Skin contact detected at some point, however briefly, between the first and second acceleration spike.

(3) Skin contact detected for a specified duration at some point between the first and second acceleration spike, e.g., between 1-3 seconds, or between 50-100% of the time period between the first and second acceleration spike.
(4) Skin contact detected, however briefly, only at the time of the first acceleration spike.
(5) Skin contact detected for a specified duration at the time of the first acceleration spike
(6) Skin contact detected, however briefly, only at the time of the second acceleration spike
(7) Skin contact detected for a specified duration leading up to the second acceleration spike Depending on the embodiment, processing circuit 2008 may evaluate any detected skin contact against any one or more of the criteria (1)-(7) listed above. For example, processing circuit 2008 may maintain a log or buffer in memory of the times and/or duration of recently sensed skin contacts, and then consult this log at step 3212 to determine whether there was skin contact that satisfies the applicable criteria. If the processing circuit detects skin contact that satisfies the applicable criteria, processing circuit 2008 branches to step 3216. If the applicable criteria are not satisfied, processing circuit 2008 branches to step 3204.

At step 3216, processing circuit 2008 determines that the first acceleration spike was caused by initiation of a dispensing event, and that the second acceleration spike was caused by a retraction movement at the completion of the dispensing event. Processing circuit 2008 then logs the initiation and completion of the dispensing event in memory, and/or communicates the initiation and/or completion of the dispensing event to an external device or to a user.

Each of processes 3000 (FIG. 30), 3100 (FIG. 31), and 3200 (FIG. 32) have been described thus far as being implemented by processing circuit 2008 within device 20. In some embodiments, however, some or all of the steps in each of these processes may be performed by, or in concert with, a processing circuit at an external device separate from device 20, such as processor 1252 at an external device 1250 (see FIG. 12). For example, some or all of the steps in each of processes 3000, 3100, and 3200 may be performed by a processor within a mobile device (e.g., a smartphone or portable computer) or a server that receives skin contact data and accelerometer data from device 20. Such skin contact and accelerometer data may be derived from measurements or signals output from the skin contact sensors 2706 and/or the accelerometer 2012, and may be received via a wireless communication link between device 20 and the external device, or via a network communication link (e.g., through the Internet or a cellular network). The external device may then log completion of the dispensing event in memory or in a report, notify and/or communicate the dispensing event to a user, or perform other actions or steps based on completion of the dispensing event. The steps performed by the external device may be performed in real-time, e.g., as the data is being measured by device 20, or may be performed some time (e.g., hours, days, or years) after the skin-contact and accelerometer data is measured and recorded by device 20.

Although the foregoing description of the third set of embodiments of device 20 describes differences between this third set of embodiments and the previously-described first and second set of embodiments, it should be understood that the third set of embodiments may also include features present in either the first or the second set of embodiments, as well as other features. For example, certain embodiments in this third set of embodiments may include the secondary PCB 84 of the first set of embodiments, including some or all of the sensors previously-described as being mounted thereon. Certain embodiments in this third set of embodiments may also include the proximally extending arms 1710*a*, 1710*b* of the second set of embodiments.

Figure 34:
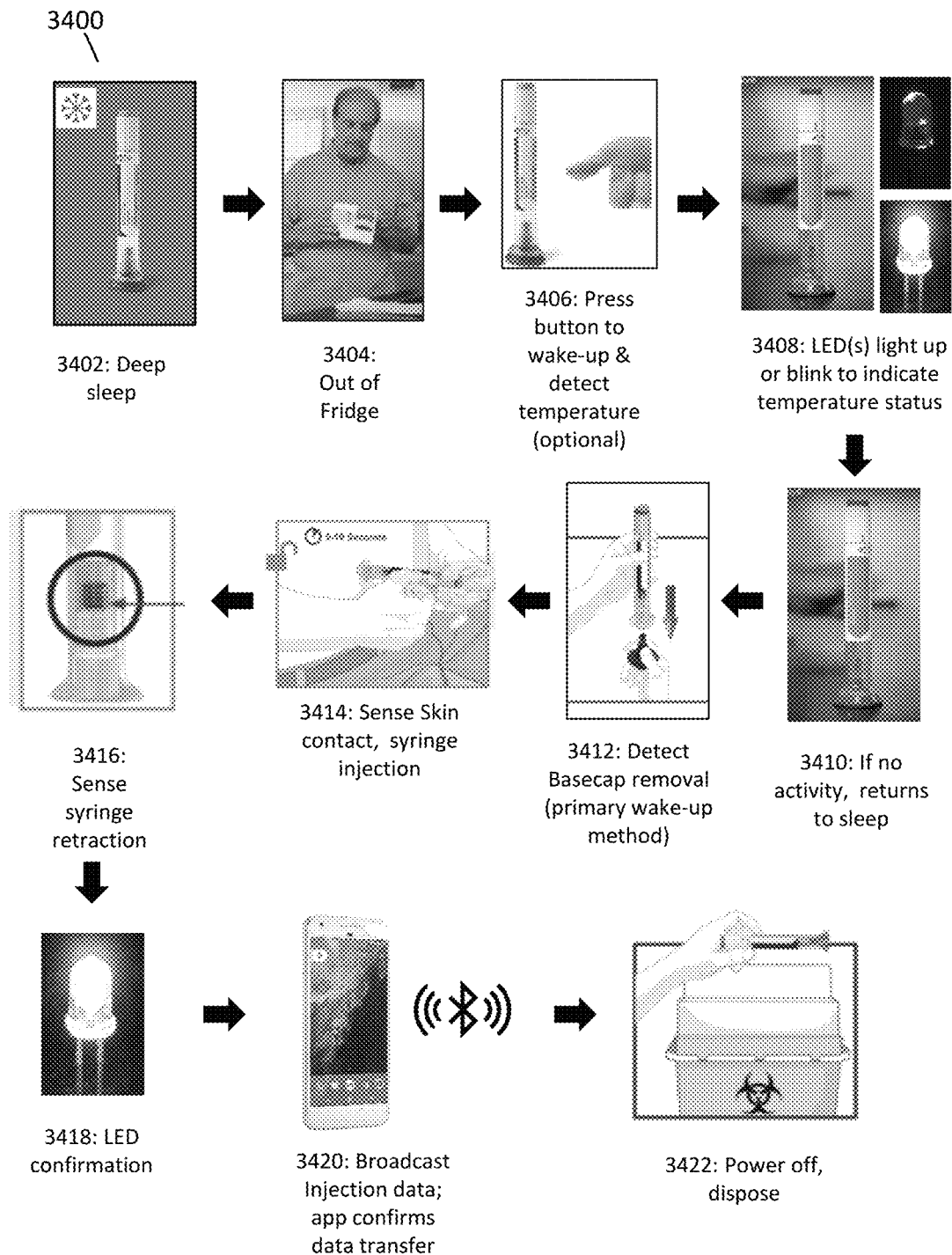
FIG. 34 depicts an exemplary sequence of user steps for using the injection device, according to any of the first, second, or third set of embodiments.

FIG. 34 shows an exemplary sequence 3400 of user steps for using medication injection device 20. This exemplary sequence 3400 may apply to any of the first, second, or third sets of embodiments of device 20 described herein. The device 20 may begin at step 3402, where the device is kept at a colder storage temperature (e.g., between 36 and 46 degrees Fahrenheit, or 2 and 8 degrees Celsius) within a storage environment (e.g., a refrigerator) to protect the medication stored within from spoliation.

At step 3404, a user takes device 20 out of the storage environment.

At step 3406, the user may optionally press a temperature check button to cause the processing circuit on device 20 to wake up and detect its temperature. For devices belonging to the first set of embodiments, this may be done by pressing a button to cause processing circuit 108 to wake up and read IR sensor 120. For devices belonging to the third set of embodiments, this may be done by pressing temperature check button 2001 and causing processing circuit 2008 to read the temperature sensor 2025.

At step 3408, one or more LEDs mounted on device 20 may light up or blink to indicate temperature status, thus indicating to the user whether the medication stored within device 20 is at or within an ideal temperature range for administration (e.g., at room temperature, or between 65 and 75 degrees Fahrenheit, or 18 and 24 degrees Celsius). For drugs that do not require a temperature check, steps 3406 and 3408 may be skipped.

At step 3410, the device 20 may go back to sleep in order to conserve battery power if no further activity is detected. Device 20 may go to sleep by powering down some or all of its electrical components, or operating some of its components in a low-power mode. For instance, in some embodiments, device 20 goes to sleep by cutting off power to its processing circuit. In some cases, power may be cut off from the processing circuit the moment the user releases the temperature check button. In other cases, power is cut off from the processing circuit within a certain pre-set period of time after the user releases the temperature check button (e.g., a number of seconds or minutes). Other electrical components, e.g., LEDs and/or sensors, may also be powered off to conserve power.

At step 3412, the device 20 detects when the user removes basecap 36. For devices belonging to the third set of embodiments, device 20 may detect when basecap 36 has been removed using basecap removal sensor 2010. This action causes device 20 to wake up again, e.g., by powering up its processing circuit.

At step 3414, the user presses device 20 against his or her body (e.g., his or her abdomen) and activates the device by unlocking and depressing actuation button 52 on the distal end of device 20. Unlocking and depressing actuation button 52 causes drive mechanism 24 to drive syringe assembly 22 from the storage position to the injection position. For devices in the third set of embodiments, device 20 senses contact with the user's skin as well as the acceleration spike associated with movement of syringe assembly 22. As discussed previously, these two sensed parameters may be interpreted by device 20 to be indicative of initiation of a dispensing event.

At step 3416, the retraction mechanism 26 drives syringe assembly 22 from the injection position to the retracted position at the end of the dispensing event. For devices in the third set of embodiments, device 20 senses contact with the user's skin as well as the acceleration spike associated with the retraction movement of syringe assembly 22. As discussed previously, these two sensed parameters may be interpreted by device 20 to be indicative of completion of a dispensing event.

At step 3418, device 20 lights up one or more LEDs mounted on the device's body to indicate to the user that the dispensing event has been successfully initiated and completed.

At step 3420, device 20 repeatedly broadcasts injection data. This data may be received by an external device (e.g., a mobile device 1250), and indicates that a dispensing event has been successfully initiated and completed, the amount of time that has passed since the dispensing event was completed, the type and/or configuration of device 20, the type of medication administered, or any other data or parameters sensed and/or stored by device 20. An application running on the external device may optionally confirm receipt of the data to device 20 by sending an acknowledgment message.

At step 3422, device 20 may be disposed of in any appropriate fashion, e.g., in a sharps container as depicted.

While this invention has been described as having an exemplary design, the embodiments of the present disclosure may be further modified within the spirit and scope of this disclosure. This application is therefore intended to cover any variations, uses, or adaptations of the disclosed embodiments using its general principles.

What is claimed is:

1. An injection device assembly comprising:
a housing;
a syringe assembly at least partially disposed within the housing;
a drive mechanism configured to drive the syringe assembly from a storage position to an injection position;
one or more skin-contact sensors, each sensor being configured to detect contact with skin tissue;
an accelerometer disposed within the housing and configured to output a signal representative of sensed acceleration; and
a processing circuit operably coupled with the one or more skin-contact sensors and the accelerometer configured to:
analyze the signal output by the accelerometer to detect acceleration spikes, and
determine that a first acceleration spike detected in the signal output by the accelerometer is caused by initiation of a dispensing event in which the syringe assembly is driven by the drive mechanism from the storage position to the injection position only when at least one of the one or more skin-contact sensors detect contact with skin tissue at a time when the first acceleration spike was detected.

2. The injection device assembly of claim 1, wherein the processing circuit is configured to analyze the signal output by the accelerometer to detect acceleration spikes when at least one of the one or more skin-contact sensors detect contact with skin tissue.

3. The injection device assembly of claim 1, wherein the accelerometer outputs the signal representative of sensed acceleration when at least one of the one or more skin-contact sensors detect contact with skin tissue.

4. The injection device assembly of claim 1, wherein:
the housing defines a proximal opening;
the one or more skin-contact sensors are each disposed adjacent to the proximal opening; and
the syringe assembly comprises a barrel to hold a medication, a slidable piston movable relative to the barrel to dispense the medication from the barrel, and an injection needle extending from the barrel, wherein the needle projects proximally out of the proximal opening when the syringe assembly is in the injection position.

5. The injection device assembly of claim 1, wherein the processing circuit is configured to determine that the first acceleration spike is caused by initiation of the dispensing event when all of the one or more skin-contact sensors detect contact with skin tissue at the time when the first acceleration spike was detected.

6. The injection device assembly of claim 1, further comprising a retraction mechanism configured to drive the syringe assembly from the injection position to a retracted position, wherein the processing circuit is further configured to determine that a second acceleration spike detected by the accelerometer subsequent to the first acceleration spike is caused by a retraction movement upon completion of the dispensing event in which the syringe assembly is driven by the retraction mechanism from the injection position to the retracted position when at least one of the one or more skin-contact sensors detect contact with skin tissue at a time when the second acceleration spike was detected.

7. The injection device assembly of claim 6, wherein the processing circuit is configured to determine that the second acceleration spike is caused by the retraction movement when all of the one or more skin-contact sensors detect contact with skin tissue at the time when the second acceleration spike was detected.

8. The injection device assembly of claim 6, further comprising a memory operably coupled with the processing circuit, wherein the processing circuit is configured to record completion of the dispensing event in the memory.

9. The injection device assembly of claim 6, wherein the processing circuit is configured to communicate completion of the dispensing event to a user via at least one of a wireless communication to an external device and one or more light-emitting diodes mounted on the injection device assembly.

10. The injection device assembly of claim 1, further comprising a medication.

11. A method for determining initiation of a dispensing event, the method comprising:
providing an injection device assembly, the assembly comprising:
a housing,
a syringe assembly at least partially disposed within the housing,
a drive mechanism configured to drive the syringe assembly from a storage position to an injection position,
one or more skin-contact sensors, each sensor being configured to detect contact with skin tissue, and
an accelerometer disposed within the device assembly and configured to output a signal representative of sensed acceleration;
determining, by at least one processing circuit, whether at least one of the one or more skin-contact sensors detect contact with skin tissue;
analyzing, by the at least one processing circuit, the signal output by the accelerometer to detect a first acceleration spike;
determining, by the at least one processing circuit, that the first acceleration spike is caused by initiation of a dispensing event in which the syringe assembly is driven by the drive mechanism from the storage position to the injection position only when at least one of the one or more skin-contact sensors detect contact with skin tissue at a time when the first acceleration spike was detected.

12. The method of claim 11, wherein the at least one processing circuit analyzes the signal output by the accelerometer to detect the first acceleration spike when at least one of the one or more skin-contact sensors detect contact with skin tissue at the time when the first acceleration spike was detected.

13. The method of claim 11, wherein the accelerometer outputs the signal representative of sensed acceleration when at least one of the one or more skin-contact sensors detect contact with skin tissue.

14. The method of claim 11, wherein:
the housing defines a proximal opening;
the one or more skin-contact sensors are each disposed adjacent to the proximal opening; and
the syringe assembly comprises a barrel to hold a medication, a slidable piston movable relative to the barrel to dispense the medication from the barrel, and an injection needle extending from the barrel, wherein the needle projects proximally out of the proximal opening when the syringe assembly is in the injection position.

15. The method of claim 11, wherein the at least one processing circuit determines that the first acceleration spike is caused by initiation of the dispensing event when all of the one or more skin-contact sensors detect contact with skin tissue at the time when the first acceleration spike was detected.

16. The method of claim 11, wherein
the injection device assembly further comprises a retraction mechanism configured to drive the syringe assembly from the injection position to a retracted position; and
the method further comprises:
analyzing, by the at least one processing circuit, the signal output by the accelerometer to detect a second acceleration spike subsequent to the first acceleration spike, and
determining, by the at least one processing circuit, that the second acceleration spike is caused by a retraction movement upon completion of the dispensing event in which the syringe assembly is driven by the retraction mechanism from the injection position to the retracted position when at least one of the one or more skin-contact sensors detect contact with skin tissue at a time when the second acceleration spike was detected.

17. The method of claim 16, wherein the at least one processing circuit determines that the second acceleration spike is caused by the retraction movement when all of the one or more skin-contact sensors detect contact with skin tissue at the time when the second acceleration spike was detected.

18. The method of claim 16, wherein the injection device assembly further comprises a memory, and the method further comprises recording completion of the dispensing event in the memory.

19. The method of claim 16, wherein the method further comprises communicating completion of the dispensing event to a user via at least one of a wireless communication to an external device and one or more light-emitting diodes mounted on the injection device assembly.

20. An injection device assembly comprising:
a housing;
a syringe assembly at least partially disposed within the housing;
a drive mechanism configured to drive the syringe assembly from a storage position to an injection position to dispense medication;
one or more skin-contact sensors, each sensor being configured to detect contact with skin tissue;
an accelerometer disposed within the housing and configured to output a signal representative of sensed acceleration; and
a processing circuit operably coupled with the one or more skin-contact sensors and the accelerometer configured to:
analyze the signal output by the accelerometer to detect a first acceleration spike and a second acceleration spike subsequent to the first acceleration spike,
determine that a dispensing event has been completed when a set of one or more conditions are satisfied, wherein the set of conditions comprises the following condition: at least one of the one or more skin-contact sensors detect contact with skin tissue at least once during a time period beginning with the first acceleration spike and ending with the second acceleration spike, and
determine that the dispensing event has not been completed when at least one condition in the set of conditions is not satisfied,
wherein the processing circuit is configured to analyze the signal output by the accelerometer to detect acceleration spikes by:
calculating an integrated signal by integrating at least a portion of the signal, and
detecting the first acceleration spike or the second acceleration spike when the integrated signal is less than a maximum signal threshold.

21. The injection device assembly of claim 20, wherein the injection device assembly further comprises a retraction mechanism configured to retract the syringe assembly from the injection position to a retracted position when the dispensing event has been completed.

22. The injection device assembly of claim 20, wherein the set of conditions further comprise a condition that requires at least one of the one or more skin-contact sensors detect contact with skin tissue at all times during the time period.

23. The injection device assembly of claim 20, wherein the set of conditions further comprise a condition that requires at least one of the one or more skin-contact sensors detect contact with skin tissue for at least 50% of the time period.

24. The injection device assembly of claim 20, wherein the set of conditions further comprise a condition that the time period be no longer than a maximum time threshold.

25. The injection device assembly of claim 20, wherein the set of conditions further comprise a condition that the time period be no shorter than a minimum time threshold.

26. The injection device assembly of claim 20, wherein the processing circuit is configured to analyze the signal output by the accelerometer to detect acceleration spikes by:
passing the signal output by the accelerometer through a filter to generate a filtered signal.

27. The injection device assembly of claim 26, wherein the processing circuit is configured to detect an acceleration spike when the integrated signal is greater than a minimum signal threshold.

28. The injection device assembly of claim 20, wherein the processing circuit is configured to detect an acceleration spike when the integrated signal is greater than a minimum signal threshold.

29. The injection device assembly of claim 20, wherein the processing circuit is further configured to communicate completion of the dispensing event to a user via at least one of a wireless communication to another device and one or more light-emitting diodes mounted on the injection device assembly.

30. The injection device assembly of claim 20, further comprising a medication.

31. A method for determining completion of a dispensing event, the method comprising:
providing an injection device assembly, the assembly comprising:
a housing,
a syringe assembly at least partially disposed within the housing,
a drive mechanism configured to drive the syringe assembly from a storage position to an injection position to dispense medication,
one or more skin-contact sensors, each sensor being configured to detect contact with skin tissue, and
an accelerometer disposed within the device assembly and configured to output a signal representative of sensed acceleration;
analyzing the signal output by the accelerometer to detect a first acceleration spike and a second acceleration spike subsequent to the first acceleration spike; and
determining whether a dispensing event has been completed by:
determining that the dispensing event has been completed when a set of one or more conditions are satisfied, wherein the set of conditions comprise the following condition: at least one of the one or more skin-contact sensors detect contact with skin tissue at least once during a time period beginning with the first acceleration spike and ending with the second acceleration spike, and
determining that the dispensing event has not been completed when at least one condition in the set of conditions is not satisfied,
wherein analyzing the signal output by the accelerometer comprises:
calculating an integrated signal by integrating at least a portion of the signal output by the accelerometer, and
detecting an acceleration spike when the integrated signal is less than a maximum signal threshold.

32. The method of claim 31, wherein the assembly further comprises a retraction mechanism configured to retract the syringe assembly from the injection position to a retracted position when the dispensing event has been completed.

33. The method of claim 31, wherein analyzing the signal output by the accelerometer and determining whether the dispensing event has been completed are performed by a processing circuit disposed within the injection device assembly.

34. The method of claim 31, further comprising sending data derived from the signal output by the accelerometer and data derived from the one or more skin-contact sensors to a processing circuit at an external device separate from the injection device assembly, wherein analyzing the signal output by the accelerometer and determining whether the dispensing event has been completed are performed by the processing circuit at the external device.

35. The method of claim 31, wherein the set of conditions further comprise a condition that requires at least one of the one or more skin-contact sensors detect contact with skin tissue at all times during the time period.

36. The method of claim 31, wherein the set of conditions further comprise a condition that requires at least one of the one or more skin-contact sensors detect contact with skin tissue for at least 50% of the time period.

37. The method of claim 31, wherein the set of conditions further comprise a condition that the time period be no longer than a maximum time threshold.

38. The method of claim 31, wherein the set of conditions further comprise a condition that the time period be no shorter than a minimum time threshold.

39. The method of claim 31, wherein analyzing the signal output by the accelerometer comprises:
passing the signal output by the accelerometer through a filter to generate a filtered signal.

40. The method of claim 39, wherein the first acceleration spike or the second acceleration spike is detected when the integrated signal is greater than a minimum signal threshold.

41. The method of claim 31, wherein the first acceleration spike or the second acceleration spike is detected when the integrated signal is greater than a minimum signal threshold.

42. The method of claim 31, further comprising communicating completion of the dispensing event to a user via at least one of a wireless communication to another device and one or more light-emitting diodes mounted on the injection device assembly.

* * * * *